US011912760B2

(12) United States Patent
Byun et al.

(10) Patent No.: US 11,912,760 B2
(45) Date of Patent: Feb. 27, 2024

(54) DOPPEL-TARGETING ANTIBODIES

(71) Applicant: PHAROSGEN CO., LTD, Seoul (KR)

(72) Inventors: Youngro Byun, Seoul (KR); Ha Kyeong Lee, Seoul (KR); So Young Choi, Sejong-si (KR); So Ra Park, Cheongju-si (KR); Se Ra Lee, Sejong-si (KR); Seung Il Baek, Seongnam-si (KR)

(73) Assignee: PHAROSGEN CO., LTD, Seoul (KR)

( * ) Notice: Subject to any disclaimer, the term of this patent is extended or adjusted under 35 U.S.C. 154(b) by 0 days.

(21) Appl. No.: 17/350,763

(22) Filed: Jun. 17, 2021

(65) Prior Publication Data

US 2022/0267422 A1 Aug. 25, 2022

(30) Foreign Application Priority Data

Feb. 15, 2021 (KR) ........................ 10-2021-0019883

(51) Int. Cl.

| | |
|---|---|
| ***A61K 39/395*** | (2006.01) |
| ***A61K 39/00*** | (2006.01) |
| ***G01N 33/53*** | (2006.01) |
| ***A61K 49/00*** | (2006.01) |
| ***C07K 16/46*** | (2006.01) |
| ***C07K 16/00*** | (2006.01) |
| ***C07K 16/18*** | (2006.01) |
| ***G01N 33/68*** | (2006.01) |
| ***A61P 35/00*** | (2006.01) |

(52) U.S. Cl.

CPC .............. *C07K 16/18* (2013.01); *A61P 35/00* (2018.01); *G01N 33/68* (2013.01); *A61K 2039/505* (2013.01); *C07K 2317/14* (2013.01); *C07K 2317/24* (2013.01); *C07K 2317/76* (2013.01); *C07K 2317/92* (2013.01)

(58) Field of Classification Search

None

See application file for complete search history.

(56) References Cited

U.S. PATENT DOCUMENTS 10,202,459 B2 * 2/2019 Byun .................. C12N 15/113
10,501,549 B2 * 12/2019 Byun .................... A61K 47/55

OTHER PUBLICATIONS

Al-Hilal et al. Prion-like protein "Doppel" is a selective therapeutic target for tumoral angiogenesis. Cancer Res (2016) 76 (14_ Supplement): 3277 (Year: 2016).*

Al-Hilal TA, Chung SW, Choi JU, Alam F, Park J, Kim SW, Kim SY, Ahsan F, Kim IS, Byun Y. Targeting prion-like protein doppel selectively suppresses tumor angiogenesis. J Clin Invest. Apr. 1, 2016;126(4):1251-66. (Year: 2016).*

Zhang et al. Abstract 5147: The prion-like protein doppel as a seurm biomarker for epithelial ovarian cancer. Cancer Res (2022) 82 (12_Supplement): 5147. (Year: 2022).*

Choi et al. Targeting angiogenic growth factors using therapeutic glycosaminoglycans on doppel-expressing endothelial cells for blocking angiogenic signaling in cancer. Biomaterials 283 (2022) 121423. (Year: 2022).*

* cited by examiner

*Primary Examiner* — Maher M Haddad

(74) *Attorney, Agent, or Firm* — Foley & Lardner LLP

(57) ABSTRACT

Described herein are doppel-targeting molecules (e.g., antibodies) useful for inhibiting pathological angiogenesis and treating diseases and conditions associated with pathological angiogenesis, such as tumors, cancers, atherosclerosis, tuberculosis, asthma, pulmonary arterial hypertension (PAH), neoplasms and neoplasm-related conditions, and for detecting doppel expression in a subject. Related compositions and methods also are described.

27 Claims, 31 Drawing Sheets

Specification includes a Sequence Listing.

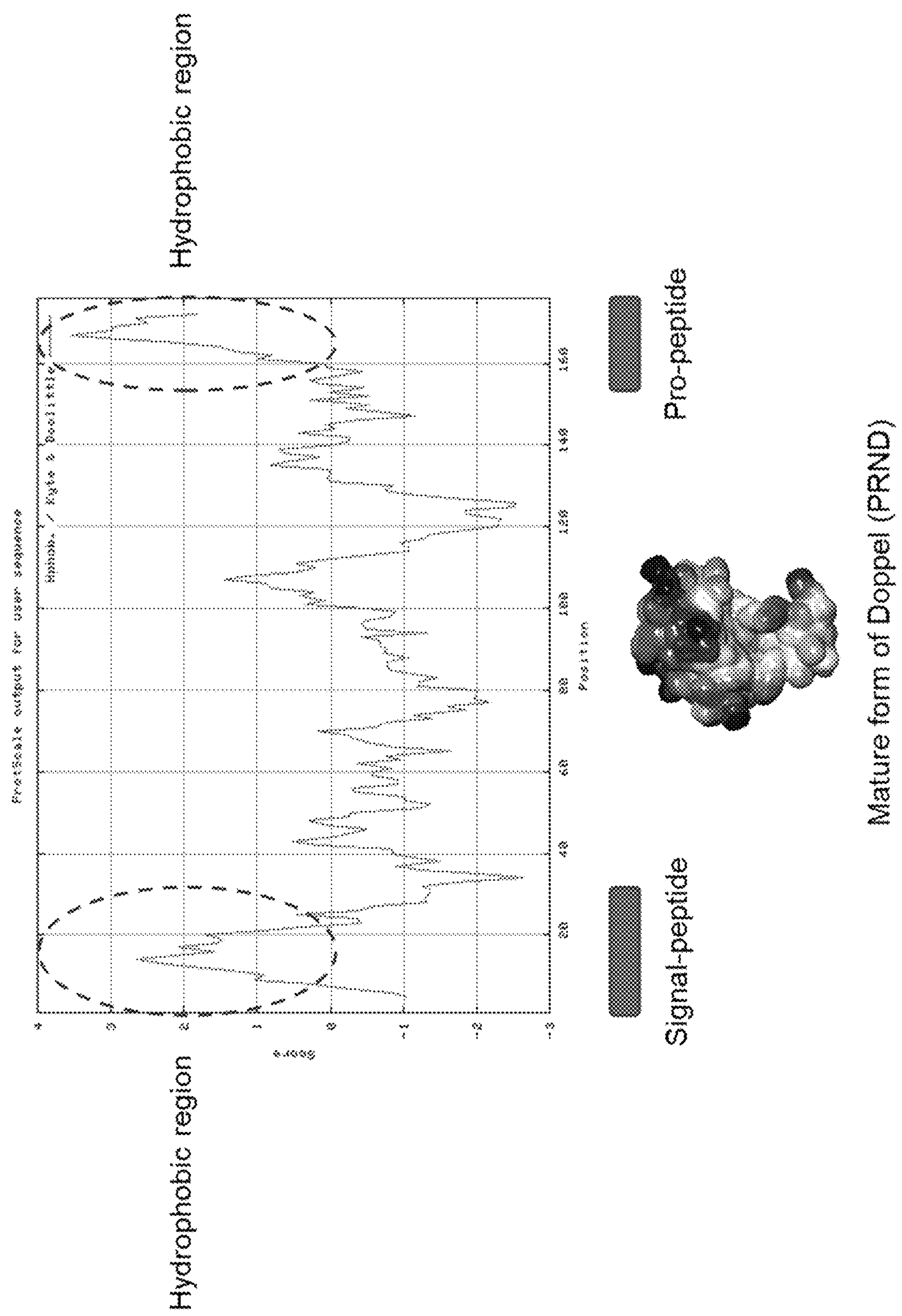
FIG.2 NMR structure of human PRND fragment 24-125

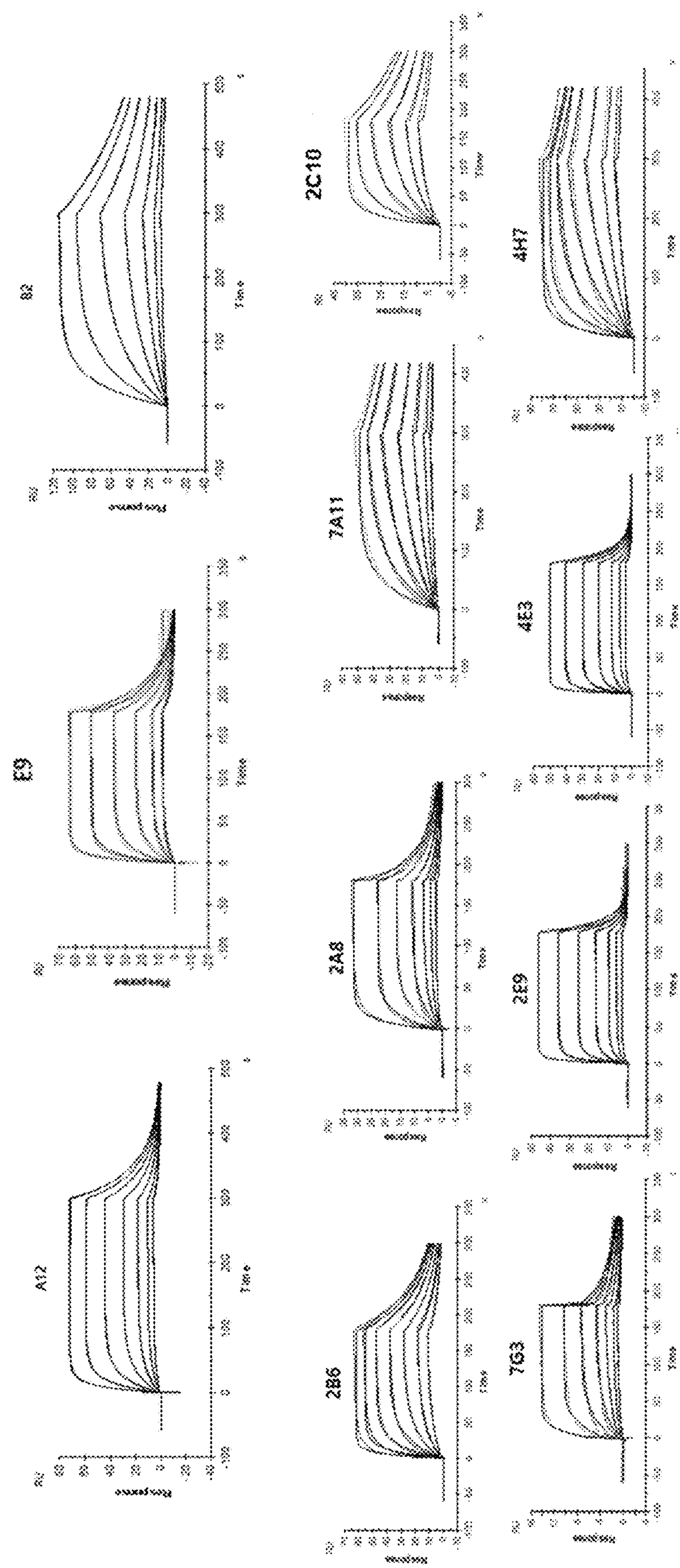
FIG.4 SPR sensor grams of anti-Doppel monoclonal antibodies.

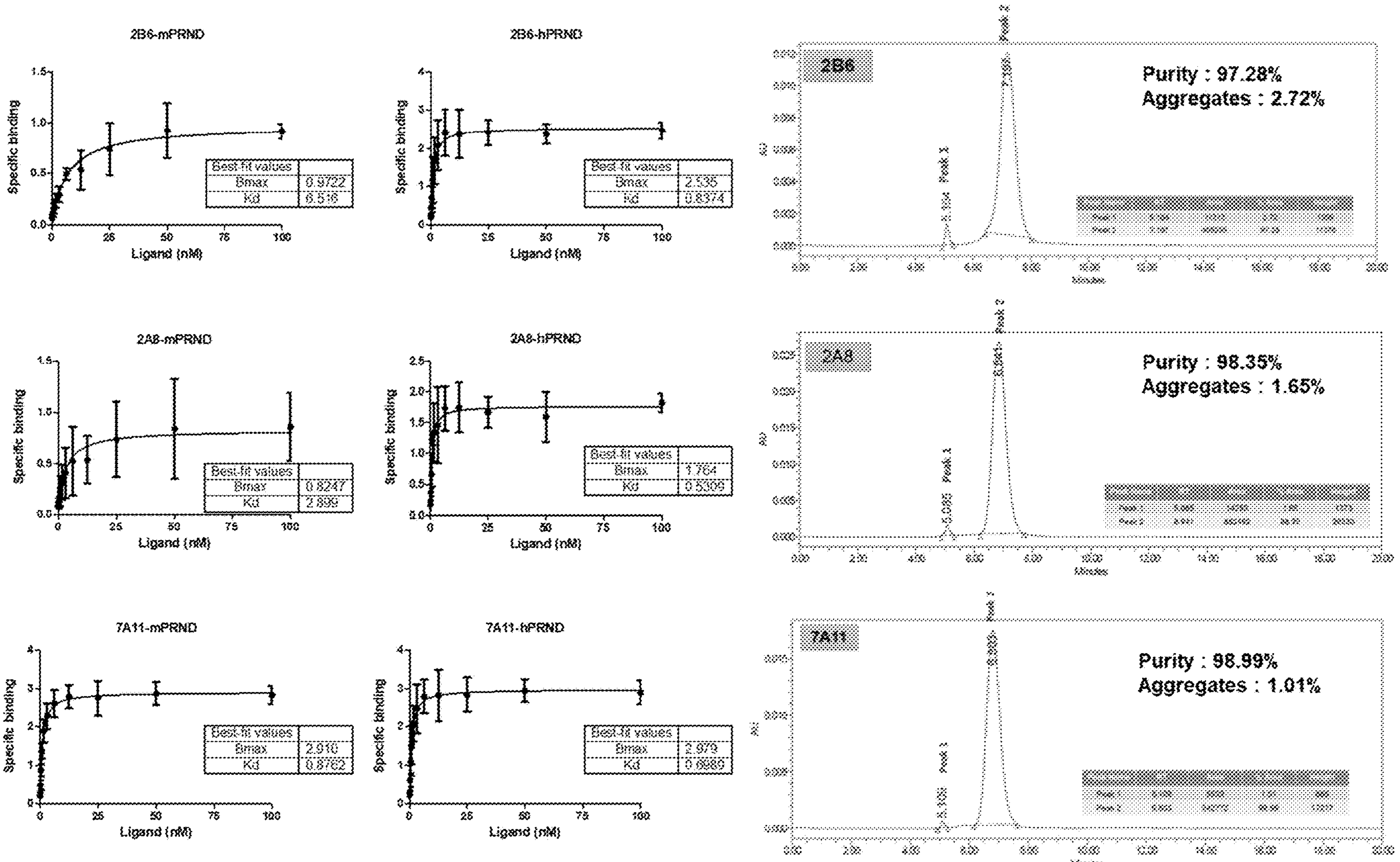
FIG.5 Evaluating binding affinity of 2B6, 2A8 and 7A11 against mPRND, hPRND using ELISA and SEC analysis.

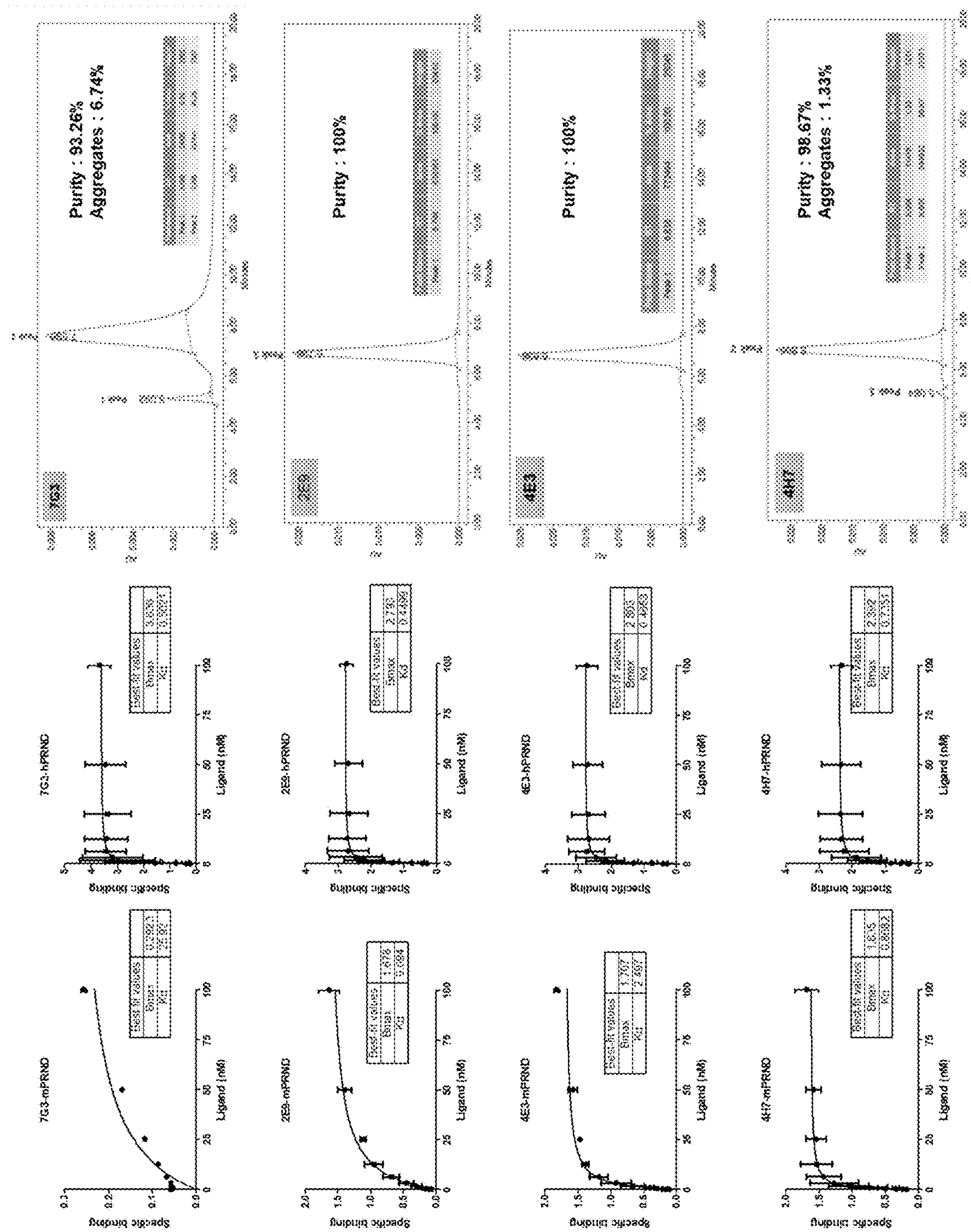
FIG. 6 Evaluating binding affinity of 7G3, 2E9, 4E3, 4H7 against mPRND, hPRND using ELISA and SEC analysis.

| | Sample Name | Subset Name | Count |
|---|---|---|---|
| | C02 B11.fcs | Single Cells | 6715 |
| | C01 E9.fcs | Single Cells | 6708 |
| | C03 H4.fcs | Single Cells | 6871 |
| | B04 Sino.fcs | Single Cells | 6804 |
| | A02 Anti-human sec.fcs | Single Cells | 6915 |

FIG. 15B

| Parameter | Units | Estimate | Standard Error | CV% |
|---|---|---|---|---|
| AUC | h*µg/mL | 4605.28 | 1052.427 | 22.85261 |
| Alpha | 1/h | 0.141356 | 0.040425 | 28.59786 |
| Beta | 1/h | 0.009839 | 0.004737 | 48.14735 |
| Alpha_$t_{1/2}$ | h | 4.903562 | 1.401747 | 28.5863 |
| Beta_$t_{1/2}$ | h | 70.44555 (2.93 days) | 33.8893 | 48.10708 |
| Cmax | µg/mL | 134.8722 | 7.615595 | 5.646528 |
| CL | mg/(h*µg/mL)/kg | 0.002171 | 0.000497 | 22.87546 |
| MRT | h | 87.64956 | 40.8034 | 46.55289 |
| Vss | mg/(µg/mL)/kg | 0.190324 | 0.051751 | 27.19098 |

FIG. 15C

| Parameter | Units | Estimate | Standard Error | CV% |
|---|---|---|---|---|
| AUC | h*µg/mL | 59911.41 | 21117.15 | 35.24729 |
| Alpha | 1/h | 0.308859 | 0.080141 | 25.94751 |
| Beta | 1/h | 0.002141 | 0.000896 | 41.84993 |
| Alpha_$t_{1/2}$ | h | 2.244219 | 0.582029 | 25.93457 |
| Beta_$t_{1/2}$ | h | 323.8126 (13.49 days) | 135.3734 | 41.80608 |
| Cmax | µg/mL | 298.2406 | 18.37809 | 6.162168 |
| CL | mg/(h*µg/mL)/kg | 0.166913 | 0.058891 | 35.28253 |
| AUMC | h*h*µg/mL | 27731263 | 21361568 | 77.03064 |
| MRT | h | 462.8711 | 194.3144 | 41.98023 |
| Vss | mg/(µg/mL)/kg | 77.25926 | 6.471917 | 8.376883 |

DOPPEL-TARGETING ANTIBODIES

CROSS-REFERENCE TO RELATED APPLICATIONS

This application claims priority under 35 U.S.C. § 119 to Korean Application No. 10-2021-0019883 filed on Feb. 15, 2021, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jul. 28, 2021, is named 128650-0102_SL.txt and is 133,463 bytes in size.

TECHNICAL FIELD

Described herein are doppel-targeting molecules, including antibodies and fragments thereof, useful for inhibiting pathological angiogenesis and treating diseases and conditions associated with pathological angiogenesis, such as tumors, cancers, atherosclerosis, tuberculosis, asthma, pulmonary arterial hypertension (PAH), neoplasms and neoplasm-related conditions, and for detecting doppel expression in a subject. Related compositions and methods also are described.

DESCRIPTION OF RELATED ART

One modality of cancer treatment involves inhibiting tumor angiogenesis. Current angiogenic inhibitors such as anti-VEGF monoclonal antibodies, TKR inhibitors, and others can also interfere with the physiological angiogenic condition. Thus, there remains a need for alternative agents effective for inhibiting pathological angiogenesis and treating diseases and conditions associated with pathological angiogenesis that have more selective activity.

SUMMARY

The present disclosure provides and includes doppel-targeting molecules that bind to doppel, and related compositions and methods. A doppel-targeting molecule as disclosed herein may be an antibody, including a mouse antibody, a human antibody, a monoclonal antibody, a chimeric antibody, a humanized antibody or a fully-human antibody.

In accordance with some embodiments, the present disclosure provides and includes doppel-targeting molecules that bind to doppel, wherein the doppel targeting molecule comprises a heavy chain variable region and a light chain variable region, wherein:

(a) the heavy chain variable region comprises a CDRH1 comprising the amino acid sequence of SEQ ID NO: 58; a CDRH2 comprising the amino acid sequence of SEQ ID NO: 59; and a CDRH3 comprising the amino acid sequence of SEQ ID NO: 60; and the light chain variable region comprises a CDRL1 comprising the amino acid sequence of SEQ ID NO: 1; a CDRL2 comprising the amino acid sequence of SEQ ID NO: 2; and a CDRL3 comprising the amino acid sequence of SEQ ID NO: 3;

(b) the heavy chain variable region comprises a CDRH1 comprising the amino acid sequence of SEQ ID NO: 61; a CDRH2 comprising the amino acid sequence of SEQ ID NO: 62; and a CDRH3 comprising the amino acid sequence of SEQ ID NO: 63; and the light chain variable region comprises a CDRL1 comprising the amino acid sequence of SEQ ID NO: 4; a CDRL2 comprising the amino acid sequence of SEQ ID NO: 5; and a CDRL3 comprising the amino acid sequence of SEQ ID NO: 6;

(c) the heavy chain variable region comprises a CDRH1 comprising the amino acid sequence of SEQ ID NO: 64; a CDRH2 comprising the amino acid sequence of SEQ ID NO: 65; and a CDRH3 comprising the amino acid sequence of SEQ ID NO: 66; and the light chain variable region comprises a CDRL1 comprising the amino acid sequence of SEQ ID NO: 7; a CDRL2 comprising the amino acid sequence of SEQ ID NO: 8; and a CDRL3 comprising the amino acid sequence of SEQ ID NO: 9;

(d) the heavy chain variable region comprises a CDRH1 comprising the amino acid sequence of SEQ ID NO: 67; a CDRH2 comprising the amino acid sequence of SEQ ID NO: 68; and a CDRH3 comprising the amino acid sequence of SEQ ID NO: 69; and the light chain variable region comprises a CDRL1 comprising the amino acid sequence of SEQ ID NO: 10; a CDRL2 comprising the amino acid sequence of SEQ ID NO: 11; and a CDRL3 comprising the amino acid sequence of SEQ ID NO: 12;

(e) the heavy chain variable region comprises a CDRH1 comprising the amino acid sequence of SEQ ID NO: 70; a CDRH2 comprising the amino acid sequence of SEQ ID NO: 71; and a CDRH3 comprising the amino acid sequence of SEQ ID NO: 72; and the light chain variable region comprising a CDRL1 comprising the amino acid sequence of SEQ ID NO: 13; a CDRL2 comprising the amino acid sequence of SEQ ID NO: 14; and a CDRL3 comprising the amino acid sequence of SEQ ID NO: 15;

(f) the heavy chain variable region comprises a CDRH1 comprising the amino acid sequence of SEQ ID NO: 73; a CDRH2 comprising the amino acid sequence of SEQ ID NO: 74; and a CDRH3 comprising the amino acid sequence of SEQ ID NO: 75; and the light chain variable region comprises a CDRL1 comprising the amino acid sequence of SEQ ID NO: 16; a CDRL2 comprising the amino acid sequence of SEQ ID NO: 17; and a CDRL3 comprising the amino acid sequence of SEQ ID NO: 18;

(g) the heavy chain variable region comprises a CDRH1 comprising the amino acid sequence of SEQ ID NO: 76; a CDRH2 comprising the amino acid sequence of SEQ ID NO: 77; and a CDRH3 comprising the amino acid sequence of SEQ ID NO: 78; and the light chain variable region comprises a CDRL1 comprising the amino acid sequence of SEQ ID NO: 19; a CDRL2 comprising the amino acid sequence of SEQ ID NO: 20; and a CDRL3 comprising the amino acid sequence of SEQ ID NO: 21;

(h) the heavy chain variable region comprises a CDRH1 comprising the amino acid sequence of SEQ ID NO: 79; a CDRH2 comprising the amino acid sequence of SEQ ID NO: 80; and a CDRH3 comprising the amino acid sequence of SEQ ID NO: 81; and the light chain variable region comprises a CDRL1 comprising the amino acid sequence of SEQ ID NO: 22; a CDRL2 comprising the amino acid sequence of SEQ ID NO: 23; and a CDRL3 comprising the amino acid sequence of SEQ ID NO: 24;

(i) the heavy chain variable region comprises a CDRH1 comprising the amino acid sequence of SEQ ID NO: 82; a CDRH2 comprising the amino acid sequence of SEQ ID NO: 83; and a CDRH3 comprising the amino acid sequence of SEQ ID NO: 84; and the light chain variable region comprises a CDRL1 comprising the amino acid sequence of SEQ ID NO: 25; a CDRL2 comprising the amino acid sequence of SEQ ID NO: 26; and a CDRL3 comprising the amino acid sequence of SEQ ID NO: 27;

(j) the heavy chain variable region comprises a CDRH1 comprising the amino acid sequence of SEQ ID NO: 85; a CDRH2 comprising the amino acid sequence of SEQ ID NO: 86; and a CDRH3 comprising the amino acid sequence of SEQ ID NO: 87; and the light chain variable region comprises a CDRL1 comprising the amino acid sequence of SEQ ID NO: 28; a CDRL2 comprising the amino acid sequence of SEQ ID NO: 29; and a CDRL3 comprising the amino acid sequence of SEQ ID NO: 30;

(k) the heavy chain variable region comprises a CDRH1 comprising the amino acid sequence of SEQ ID NO: 88; a CDRH2 comprising the amino acid sequence of SEQ ID NO: 89; and a CDRH3 comprising the amino acid sequence of SEQ ID NO: 90; and the light chain variable region comprises a CDRL1 comprising the amino acid sequence of SEQ ID NO: 31; a CDRL2 comprising the amino acid sequence of SEQ ID NO: 32; and a CDRL3 comprising the amino acid sequence of SEQ ID NO: 33;

(l) the heavy chain variable region comprises a CDRH1 comprising the amino acid sequence of SEQ ID NO: 91; a CDRH2 comprising the amino acid sequence of SEQ ID NO: 92; and a CDRH3 comprising the amino acid sequence of SEQ ID NO: 93; and the light chain variable region comprises a CDRL1 comprising the amino acid sequence of SEQ ID NO: 34; a CDRL2 comprising the amino acid sequence of SEQ ID NO: 35; and a CDRL3 comprising the amino acid sequence of SEQ ID NO: 36;

(m) the heavy chain variable region comprises a CDRH1 comprising the amino acid sequence of SEQ ID NO: 94; a CDRH2 comprising the amino acid sequence of SEQ ID NO: 95; and a CDRH3 comprising the amino acid sequence of SEQ ID NO: 96; and the light chain variable region comprises a CDRL1 comprising the amino acid sequence of SEQ ID NO: 37; a CDRL2 comprising the amino acid sequence of SEQ ID NO: 38; and a CDRL3 comprising the amino acid sequence of SEQ ID NO: 39;

(n) the heavy chain variable region comprises a CDRH1 comprising the amino acid sequence of SEQ ID NO: 97; a CDRH2 comprising the amino acid sequence of SEQ ID NO: 98; and a CDRH3 comprising the amino acid sequence of SEQ ID NO: 99; and the light chain variable region comprises a CDRL1 comprising the amino acid sequence of SEQ ID NO: 40; a CDRL2 comprising the amino acid sequence of SEQ ID NO: 41; and a CDRL3 comprising the amino acid sequence of SEQ ID NO: 42;

(o) the heavy chain variable region comprises a CDRH1 comprising the amino acid sequence of SEQ ID NO: 100; a CDRH2 comprising the amino acid sequence of SEQ ID NO: 101; and a CDRH3 comprising the amino acid sequence of SEQ ID NO: 102; and the light chain variable region comprises a CDRL1 comprising the amino acid sequence of SEQ ID NO: 43; a CDRL2 comprising the amino acid sequence of SEQ ID NO: 44; and a CDRL3 comprising the amino acid sequence of SEQ ID NO: 45;

(p) the heavy chain variable region comprises a CDRH1 comprising the amino acid sequence of SEQ ID NO: 103; a CDRH2 comprising the amino acid sequence of SEQ ID NO: 104; and a CDRH3 comprising the amino acid sequence of SEQ ID NO: 105; and the light chain variable region comprises a CDRL1 comprising the amino acid sequence of SEQ ID NO: 46; a CDRL2 comprising the amino acid sequence of SEQ ID NO: 47; and a CDRL3 comprising the amino acid sequence of SEQ ID NO: 48;

(q) the heavy chain variable region comprises a CDRH1 comprising the amino acid sequence of SEQ ID NO: 106; a CDRH2 comprising the amino acid sequence of SEQ ID NO: 107; and a CDRH3 comprising the amino acid sequence of SEQ ID NO: 108; and the light chain variable region comprises a CDRL1 comprising the amino acid sequence of SEQ ID NO: 49; a CDRL2 comprising the amino acid sequence of SEQ ID NO: 50; and a CDRL3 comprising the amino acid sequence of SEQ ID NO: 51;

(r) the heavy chain variable region comprises a CDRH1 comprising the amino acid sequence of SEQ ID NO: 109; a CDRH2 comprising the amino acid sequence of SEQ ID NO: 110; and a CDRH3 comprising the amino acid sequence of SEQ ID NO: 111; and the light chain variable region comprises a CDRL1 comprising the amino acid sequence of SEQ ID NO: 52; a CDRL2 comprising the amino acid sequence of SEQ ID NO: 53; and a CDRL3 comprising the amino acid sequence of SEQ ID NO: 54; or (s) the heavy chain variable region comprises a CDRH1 comprising the amino acid sequence of SEQ ID NO: 112; a CDRH2 comprising the amino acid sequence of SEQ ID NO: 113; and a CDRH3 comprising the amino acid sequence of SEQ ID NO: 114; and the light chain variable region comprises a CDRL1 comprising the amino acid sequence of SEQ ID NO: 55; a CDRL2 comprising the amino acid sequence of SEQ ID NO: 56; and a CDRL3 comprising the amino acid sequence of SEQ ID NO: 57.

The present disclosure also provides and includes, a doppel-targeting molecule that binds to doppel, wherein the doppel targeting molecule comprises a heavy chain variable region and a light chain variable region, wherein:

(a) the heavy chain variable regions comprises the amino acid sequence of SEQ ID NO: 134 and the light chain variable region comprises the amino acid sequence of SEQ ID NO: 115;

(b) the heavy chain variable regions comprises the amino acid sequence of SEQ ID NO: 135 and the light chain variable region comprises the amino acid sequence of SEQ ID NO: 116;

(c) the heavy chain variable regions comprises the amino acid sequence of SEQ ID NO: 136 and the light chain variable region comprises the amino acid sequence of SEQ ID NO: 117;

(d) the heavy chain variable regions comprises the amino acid sequence of SEQ ID NO: 137 and the light chain variable region comprises the amino acid sequence of SEQ ID NO: 118;

(e) the heavy chain variable regions comprises the amino acid sequence of SEQ ID NO: 138 and the light chain variable region comprises the amino acid sequence of SEQ ID NO: 119;

(f) the heavy chain variable regions comprises the amino acid sequence of SEQ ID NO: 139 and the light chain variable region comprises the amino acid sequence of SEQ ID NO: 120;

(g) the heavy chain variable regions comprises the amino acid sequence of SEQ ID NO: 140 and the light chain variable region comprises the amino acid sequence of SEQ ID NO: 121;

(h) the heavy chain variable regions comprises the amino acid sequence of SEQ ID NO: 141 and the light chain variable region comprises the amino acid sequence of SEQ ID NO: 122;

(i) the heavy chain variable regions comprises the amino acid sequence of SEQ ID NO: 142 and the light chain variable region comprises the amino acid sequence of SEQ ID NO: 123;

(j) the heavy chain variable regions comprises the amino acid sequence of SEQ ID NO: 143 and the light chain variable region comprises the amino acid sequence of SEQ ID NO: 124;

(k) the heavy chain variable regions comprises the amino acid sequence of SEQ ID NO: 144 and the light chain variable region comprises the amino acid sequence of SEQ ID NO: 125;

(l) the heavy chain variable regions comprises the amino acid sequence of SEQ ID NO: 145 and the light chain variable region comprises the amino acid sequence of SEQ ID NO: 126;

(m) the heavy chain variable regions comprises the amino acid sequence of SEQ ID NO: 146 and the light chain variable region comprises the amino acid sequence of SEQ ID NO: 127;

(n) the heavy chain variable regions comprises the amino acid sequence of SEQ ID NO: 147 and the light chain variable region comprises the amino acid sequence of SEQ ID NO: 128;

(o) the heavy chain variable regions comprises the amino acid sequence of SEQ ID NO: 148 and the light chain variable region comprises the amino acid sequence of SEQ ID NO: 129;

(p) the heavy chain variable regions comprises the amino acid sequence of SEQ ID NO: 149 and the light chain variable region comprises the amino acid sequence of SEQ ID NO: 130;

(q) the heavy chain variable regions comprises the amino acid sequence of SEQ ID NO: 150 and the light chain variable region comprises the amino acid sequence of SEQ ID NO: 131;

(r) the heavy chain variable regions comprises the amino acid sequence of SEQ ID NO: 151 and the light chain variable region comprises the amino acid sequence of SEQ ID NO: 132; or (s) the heavy chain variable regions comprises the amino acid sequence of SEQ ID NO: 152 and the light chain variable region comprises the amino acid sequence of SEQ ID NO: 133.

The present disclosure also provides and includes, a doppel-targeting molecule that binds to doppel, wherein the doppel-targeting molecule is selected from:

(a) a doppel-binding murine antibody produced by a hybridoma cell line clone selected from:

(i) Hybridoma cell line clone 2B6, deposited on Sep. 29, 2020 with Korean Cell Line Research Foundation as hPrnd #2B6 under Accession Number KCLRF-BP-00490;

(ii) Hybridoma cell line clone 2A8, deposited on Sep. 29, 2020 with Korean Cell Line Research Foundation as mPrnd #2A8 under Accession Number KCLRF-BP-00489;

(iii) Hybridoma cell line clone 7A11, deposited on Oct. 19, 2020 with Korean Cell Line Research Foundation as hPrnd #7A11 under Accession Number KCLRF-BP-00498;

(iv) Hybridoma cell line clone 7G3, deposited on Oct. 19, 2020 with Korean Cell Line Research Foundation as hPrnd #7G3 under Accession Number KCLRF-BP-00500;

(v) Hybridoma cell line clone 2E9, deposited on Sep. 29, 2020 with Korean Cell Line Research Foundation as hPrnd #2E9 under Accession Number KCLRF-BP-00493;

(vi) Hybridoma cell line clone 4E3, deposited on Oct. 19, 2020 with Korean Cell Line Research Foundation as hPrnd #4E3 under Accession Number KCLRF-BP-00495;

(vii) Hybridoma cell line clone 4H7, deposited on Oct. 19, 2020 with Korean Cell Line Research Foundation as hPrnd #4H7 under Accession Number KCLRF-BP-00496;

(viii) Hybridoma cell line clone 2C10, deposited on Sep. 29, 2020 with Korean Cell Line Research Foundation as hPrnd #2C10 under Accession Number KCLRF-BP-00491;

(ix) Hybridoma cell line clone 2C12, deposited on Sep. 29, 2020 with Korean Cell Line Research Foundation as hPrnd #2C12 under Accession Number KCLRF-BP-00492;

(x) Hybridoma cell line clone 5D3, deposited on Oct. 19, 2020 with Korean Cell Line Research Foundation as hPrnd #5D3 under Accession Number KCLRF-BP-00497;

(xi) Hybridoma cell line clone 4D5, deposited on Oct. 19, 2020 with Korean Cell Line Research Foundation as hPrnd #4D5 under Accession Number KCLRF-BP-00494;

(xii) Hybridoma cell line clone 7D7, deposited on Oct. 19, 2020 with Korean Cell Line Research Foundation as hPrnd #7D7 under Accession Number KCLRF-BP-00499, and doppel-binding fragments of any thereof.

The present disclosure also provides and includes, a doppel-targeting molecule that binds to doppel, wherein the doppel-targeting molecule is selected from:

(b) a doppel-binding human monoclonal antibody selected from:

(xiii) Human monoclonal antibody A12 disclosed herein;

(xiv) Human monoclonal antibody B2 disclosed herein;

(xv) Human monoclonal antibody E9 disclosed herein;

(xvi) Human monoclonal antibody 3D5 disclosed herein;

(xvii) Human monoclonal antibody 3D1 disclosed herein;

(xviii) Human monoclonal antibody 4D1 disclosed herein;

(xix) Human monoclonal antibody 3H9 disclosed herein, and doppel-binding fragments of any thereof.

The present disclosure also provides and includes, a doppel-targeting molecule that binds to doppel, wherein the doppel-targeting molecule is a chimeric antibody, wherein the chimeric antibody comprises a variable heavy chain region and variable light chain region from a mouse antibody as disclosed herein (e.g., any of 2B6, 2A8, 7A11, 7G3, 2E9, 4E3, 4H7, 2C10, 2C12, 5D3, 4D5 and 7D7) and a constant heavy chain region and constant light chain region from a human IgG1 antibody.

The present disclosure also provides and includes, a doppel-targeting molecule that binds to doppel, wherein the doppel-targeting molecule is a humanized antibody, wherein the humanized antibody comprises the CDR regions of a mouse antibody as disclosed herein (e.g., any of 2B6, 2A8, 7A11, 7G3, 2E9, 4E3, 4H7, 2C10, 2C12, 5D3, 4D5 and 7D7) and variable heavy chain, variable light chain, constant heavy chain, and constant light chain regions from a human antibody, such as a human IgG1 antibody.

In some embodiments, the doppel-targeting molecule is:

(c) a doppel-binding chimeric antibody selected from:

(xx) a chimeric antibody having a light chain sequence comprising the amino acid sequence of SEQ ID NO: 155 and a heavy chain sequence comprising the amino acid sequence of SEQ ID NO: 157, optionally wherein the chimeric antibody is chimeric antibody 7G3 as described herein;

(xxi) a chimeric antibody having a light chain sequence comprising the amino acid sequence of SEQ ID NO: 159 and a heavy chain sequence comprising the amino acid sequence of SEQ ID NO: 161, optionally wherein the chimeric antibody is chimeric antibody 2B6 as described herein;

and doppel-binding fragments of any thereof.

In some embodiments, the doppel-targeting molecule is:

(d) a doppel-binding humanized antibody selected from:

(xxii) a humanized antibody having a light chain sequence comprising the amino acid sequence of SEQ ID NO: 163 and a heavy chain sequence comprising the amino acid sequence of SEQ ID NO: 165, optionally wherein the humanized antibody is humanized antibody 7G3 as described herein;

(xxiii) a humanized antibody having a light chain sequence comprising the amino acid sequence of SEQ ID NO: 167 and a heavy chain sequence comprising the amino acid sequence of SEQ ID NO: 169, optionally wherein the humanized antibody is humanized antibody 2B6 as described herein;

and doppel-binding fragments of any thereof.

A doppel-targeting molecule as disclosed herein may be labeled with or includes a detectable label.

The doppel-targeting molecules disclosed herein may interfere with the interaction of doppel and a tyrosine kinase receptor selected from VEGFR2, VEGFR1, VEGFR3, bFGFR, and PDGFR.

This disclosure also provides and includes a pharmaceutical composition comprising a doppel-targeting molecule as disclosed herein and a pharmaceutically acceptable carrier or diluent. The composition may be formulated for a route of administration selected from oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, and topical administration. In some embodiments, the doppel-targeting molecule is an anti-doppel antibody or a doppel-binding fragment thereof and is formulated for intravenous injection. In some embodiments, a pharmaceutical composition as disclosed herein comprises a monoclonal antibody and a pharmaceutically acceptable carrier or diluent.

This disclosure also provides and includes an in vitro method of detecting doppel expression in a subject, comprising (i) contacting a doppel-targeting molecule according to claim 1 with a physiological sample obtained from the subject, and (ii) detecting any binding between the doppel-targeting molecule and any doppel present in the sample. The subject may suffer from or be at risk of developing one or more of a tumor or a disease or condition selected from one or more of cancer, atherosclerosis, tuberculosis, asthma, pulmonary arterial hypertension (PAH), a neoplasm, and a neoplasm-related condition.

This disclosure provides and includes a method of inhibiting pathological angiogenesis in a subject in need thereof, comprising administering to the subject an effective amount of a doppel-targeting molecule as disclosed herein. The effective amount may be effective to inhibit angiogenesis. The doppel-targeting molecule may be administered by a route selected from oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, and topical administration. In some embodiments, the doppel-targeting molecule is administered by intravenous injection.

The subject may suffer from or be at risk of developing a tumor; the effective amount may be effective to inhibit tumorigenesis and/or to decrease tumor vasculature. The subject may suffer from or be at risk of developing a disease or condition selected from one or more of cancer, atherosclerosis, tuberculosis, asthma, pulmonary arterial hypertension (PAH), a neoplasm, and a neoplasm-related condition; the effective amount may be effective to decrease pathological vasculature associated with the cancer, atherosclerosis, tuberculosis, asthma, pulmonary arterial hypertension (PAH), neoplasm, or neoplasm-related condition, respectively. The neoplasm or neoplasm-related condition may be selected from breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and Meigs' syndrome.

This disclosure also provides and includes an in vivo method of detecting doppel expression in a subject, comprising (i) administering to the subject a doppel-targeting molecule and (ii) detecting any binding between the doppel-targeting molecule and any doppel expressed in the subject. The subject may suffer from or be at risk of developing one or more of a tumor and a disease or condition selected from one or more of cancer, atherosclerosis, tuberculosis, asthma, and pulmonary arterial hypertension (PAH), a neoplasm, and a neoplasm-related condition.

In accordance with any methods disclosed herein the subject may be a human.

BRIEF DESCRIPTION OF DRAWINGS

FIG. 2 shows the NMR analysis of human PRND fragment 24-125

FIG. 4 shows SPR sensor grams of anti-doppel monoclonal antibodies disclosed herein.

FIG. 5 shows an evaluation of binding affinity of monoclonal antibodies 2B6, 2A8 and 7A11 against mPRND and hPRND using ELISA and SEC analysis.

FIG. 6 shows an evaluation of binding affinity of monoclonal antibodies 7G3, 2E9, 4E3, and 4H7 against mPRND and hPRND using ELISA and SEC analysis.

FIG. 15A-15C show pharmacokinetic profiles and parameters for 7G3 and Avastin. Plasma concentration of each antibody is shown in FIG. 15A. Pharmacokinetic parameters of 7G3 is shown in FIG. 15B. Pharmacokinetic parameters of Avastin is shown in FIG. 15C.

Technical Problem

Figure 1A:
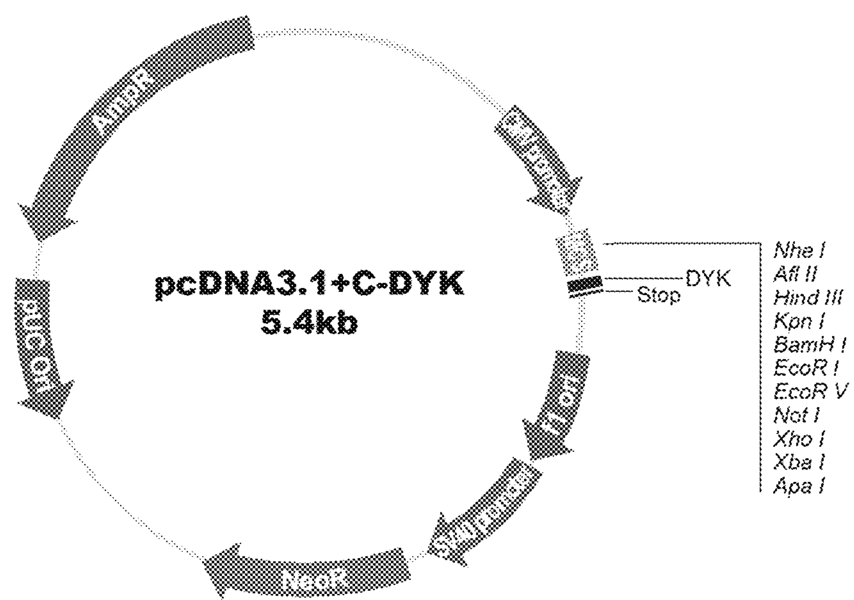
FIG. 1A-1B show the production and characterization of hPRND and mPRND in mammalian cells. pcDNA for transfecting doppel is shown (FIG. 1A). Expression of doppel protein (hPRND and mPRND) was shown by western blot (FIG. 1B).
Figure 1B:
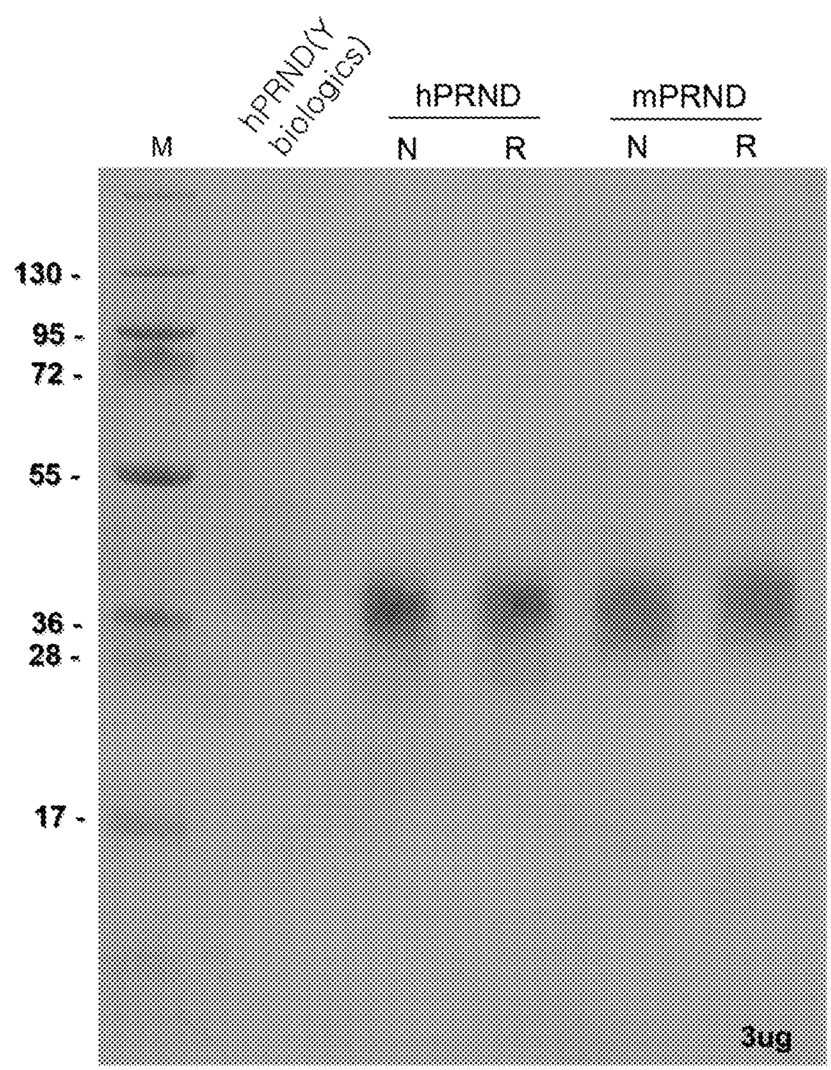

The prion like protein doppel is selectively expressed on tumor cells as well as on endothelial cells under pathological conditions, such as cancer, atherosclerosis, tuberculosis, asthma, and pulmonary arterial hypertension (PAH). Although the role of doppel in the development of these diseases is not fully understood, the doppel protein has been identified as a potential target for treating these diseases. As doppel is actively involved in angiogenic signals, targeting doppel can be a promising way to selectively inhibit pathological angiogenesis. Furthermore, as doppel is also expressed on tumor cells, doppel can be a potential target for applications in various fields, such as for tumor-specific biomarkers, direct therapeutic targets, etc.

Solution to Problem

Described herein are doppel-targeting molecules, including, but not limited to, antibodies and fragments thereof, useful, for example, in treating a disease or a condition such as cancer, atherosclerosis, tuberculosis, asthma, or pulmonary arterial hypertension (PAH) in a subject in need thereof, or for treating a neoplasm or neoplasm-related condition in a subject in need thereof, or for detecting doppel expression in a subject. The doppel-targeting molecules described herein also are useful for detecting doppel expression in a subject, using in vitro or in vivo methodologies.

Doppel-targeting molecules described herein include murine monoclonal antibodies produced by the following clones:

(i) Hybridoma cell line clone 2B6, deposited on Sep. 29, 2020 with Korean Cell Line Research Foundation as hPrnd #2B6 under Accession Number KCLRF-BP-00490;

(ii) Hybridoma cell line clone 2A8, deposited on Sep. 29, 2020 with Korean Cell Line Research Foundation as mPrnd #2A8 under Accession Number KCLRF-BP-00489;

(iii) Hybridoma cell line clone 7A11, deposited on Oct. 19, 2020 with Korean Cell Line Research Foundation as hPrnd #7A11 under Accession Number KCLRF-BP-00498;

(iv) Hybridoma cell line clone 7G3, deposited on Oct. 19, 2020 with Korean Cell Line Research Foundation as hPrnd #7G3 under Accession Number KCLRF-BP-00500;

(v) Hybridoma cell line clone 2E9, deposited on Sep. 29, 2020 with Korean Cell Line Research Foundation as hPrnd #2E9 under Accession Number KCLRF-BP-00493;

(vi) Hybridoma cell line clone 4E3, deposited on Oct. 19, 2020 with Korean Cell Line Research Foundation as hPrnd #4E3 under Accession Number KCLRF-BP-00495;

(vii) Hybridoma cell line clone 4H7, deposited on Oct. 19, 2020 with Korean Cell Line Research Foundation as hPrnd #4H7 under Accession Number KCLRF-BP-00496;

(viii) Hybridoma cell line clone 2C10, deposited on Sep. 29, 2020 with Korean Cell Line Research Foundation as hPrnd #2C10 under Accession Number KCLRF-BP-00491;

(ix) Hybridoma cell line clone 2C12, deposited on Sep. 29, 2020 with Korean Cell Line Research Foundation as hPrnd #2C12 under Accession Number KCLRF-BP-00492;

(x) Hybridoma cell line clone 5D3, deposited on Oct. 19, 2020 with Korean Cell Line Research Foundation as hPrnd #5D3 under Accession Number KCLRF-BP-00497;

(xi) Hybridoma cell line clone 4D5, deposited on Oct. 19, 2020 with Korean Cell Line Research Foundation as hPrnd #4D5 under Accession Number KCLRF-BP-00494; and (xii) Hybridoma cell line clone 7D7, deposited on Oct. 19, 2020 with Korean Cell Line Research Foundation as hPrnd #7D7 under Accession Number KCLRF-BP-00499.

Doppel-targeting molecules described herein also include the following human monoclonal antibodies, which have the heavy and light chain variable region amino acid sequences disclosed herein below:

(xiii) Human monoclonal antibody A12;

(xiv) Human monoclonal antibody B2;

(xv) Human monoclonal antibody E9;

(xvi) Human monoclonal antibody 3D5;

(xvii) Human monoclonal antibody 3D1;

(xviii) Human monoclonal antibody 4D1; and (xix) Human monoclonal antibody 3H9.

Doppel-targeting molecules described herein also include chimeric antibodies, including humanized antibodies, including chimeric/humanized antibodies. In some embodiments, the chimeric antibodies, humanized antibodies, or the chimeric/humanized antibodies have a variable heavy chain region and a variable light chain region from a mouse antibody as disclosed herein (e.g., any of 2B6, 2A8, 7A11, 7G3, 2E9, 4E3, 4H7, 2C10, 2C12, 5D3, 4D5 and 7D7) and a constant heavy chain region and constant light chain region from a human antibody, such as a human IgG1 antibody. In some embodiments, the chimeric antibodies, humanized antibodies, or the chimeric/humanized antibodies have the CDR regions of a mouse antibody as disclosed herein (e.g., any of 2B6, 2A8, 7A11, 7G3, 2E9, 4E3, 4H7, 2C10, 2C12, 5D3, 4D5 and 7D7) and the variable heavy chain, variable light chain, constant heavy chain, and constant light chain regions from a human antibody, such as a human IgG1 antibody. In specific embodiments, a chimeric/humanized antibody as disclosed herein comprises a heavy chain region selected from the human heavy chain gene IGHV1-46, IGHJ4, or VH3-66. In further specific embodiments, a chimeric/humanized antibody as disclosed herein comprises a light chain region selected from the human light chain gene IGKV3D-1 or IGKV3D-39.

In further specific embodiments, a chimeric/humanized doppel-targeting molecule as described herein is selected from the chimeric and humanized antibodies described in the examples below:

(xx) chimeric antibody 7G3;

(xxi) chimeric antibody 2B6;

(xxii) humanized antibody 7G3; and (xxiii) humanized antibody 2B6.

Doppel-binding molecules related to any of the foregoing also are included in the doppel-targeting molecules described herein, such as derivatives of the doppel-binding antibodies above and doppel-binding fragments thereof, such as molecules having the heavy chain variable region and light chain variable region amino acid sequences set forth below.

Also provided are compositions comprising a doppel-binding molecule as described herein and a pharmaceutically acceptable carrier or diluent. Any doppel-targeting molecules described herein can be used to treat a subject in need thereof, wherein the subject can be a human. The subject may suffer from or be at a risk of tumor, and/or a disease or condition selected from one or more of cancer, atherosclerosis, tuberculosis, asthma, and pulmonary arterial hypertension (PAH) or neoplasm or neoplasm-related condition, such as those discussed below.

The doppel-targeting molecules described herein, such as anti-doppel antibodies and doppel-binding fragments thereof, can be used or administered in amounts effective to interfere with the interaction of doppel with tyrosine kinase receptors such as VEGFR2, VEGFR1, VEGFR3, bFGFR, and PDGFR, or to interfere with doppel targeting of tumor cells. An "effective amount" as used herein refers to a dose effective for targeting tumor cells for diagnostic purposes or therapeutic purposes, and may be effective for one or more of inhibiting angiogenesis, tumorigenesis, decreasing pathological vasculatures related to cancer, atherosclerosis, tuberculosis, asthma, and pulmonary arterial hypertension (PAH), respectively.

Any doppel-targeting molecules described herein can be used for detecting doppel expression in a subject, or in a physiological sample obtained from a subject. The subject may be a human subject, and may be in any pathological state described above.

Also provided are the hybridoma cell lines producing doppel-binding antibodies described below.

DETAILED DESCRIPTION OF EMBODIMENTS

The inventors discovered that doppel is over-expressed on tumor cells and pathological endothelial cells only under pathological angiogenic conditions. Also, an interaction between doppel and tyrosine kinase receptors such as VEGFR, FGFR1, etc., can facilitate the angiogenic process. Thus, doppel-targeting molecules, such as antibodies and fragments thereof, which can interfere with the interaction between them can used as anti-angiogenic agents. These molecules may selectively inhibit the pathological angiogenesis associated with cancer, asthma, tuberculosis, atherosclerosis, pulmonary arterial hypertension (PAH), and neoplasms and neoplasm-related conditions.

For cancer treatment, doppel-targeting molecules, such as antibodies and fragments thereof, may target both tumor endothelial cells (TEC) and tumor cells. Doppel-targeting molecules, such as antibodies and fragments thereof, can be used as diagnostic agents, direct therapeutic agents, drug carriers, etc. Doppel targeting molecules, such as antibodies and fragments thereof, and pharmaceutical compositions comprising them may inhibit the tumor growth by inhibiting tumor angiogenesis by disturbing the interaction between doppel and tyrosine kinase receptors. Tumor endothelial cells (TEC) may be a more effective target for doppel-targeting molecules rather cancer cells themselves, as doppel is over-expressed on pathological endothelial cells and endothelial cells are more accessible to circulating pharmaceutical agents. Thus, targeting endothelial cells offers numerous advantages because doppel expression offers a more predictable and effective result than targeting cancer cells more generally. Thus, doppel-targeting molecules offer an alternative way to promote therapeutic efficacy while reducing unwanted side effects. Moreover, because doppel may be an important biomarker, determining the expression of doppel on, e.g., tumor cells, could be useful for diagnosis, and for predicting or assessing the efficacy of doppel-targeting molecules. Thus, the doppel-targeting molecules described herein can target doppel molecules expressed on pathological endothelial cells or tumor cells for therapeutic and diagnostic purposes.

Definitions

Technical and scientific terms used herein have the meanings commonly understood by one of ordinary skill in the art to which the present invention pertains, unless otherwise defined.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language ("e.g." or "such as") herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the phrases "effective amount" mean that amount that provides the specific effect for which the molecule, agent, or composition is administered. It is emphasized that an effective amount will not always be effective in treating the target condition in a given subject, even though such amount is deemed to be an effective amount by those of skill in the art. Those skilled in the art guided by the present disclosure can determine and adjust such amounts in accordance with standard practices as needed to treat a specific subject and/or condition.

As used herein, the term "angiogenesis" refers to the generation of new blood vessels. As used herein, the term "tumorigenesis" refers to the growth of a tumor. As used herein, the term "pathological angiogenesis" refers to angiogenesis associated with a cancer, tumor, or other disease or condition, such as a disease or condition associated with increased vasculature, and is distinct from physiological angiogenesis, such as occurs during growth, wound healing, and the formation of granulation tissue.

As used herein, the term "angiogenic factor" includes molecules that promote angiogenesis, such as VEGFs, FGFs, PDGFB, EGF, LPA, HGF, PD-ECF, IL-8, angiogenm, TNF-alpha, TGF-beta, TGF-alpha, proliferin, and PLGF.

As used herein, the term "tyrosine kinase receptor" refers to a class of cell surface receptors with an extracellular domain that binds a ligand and an intracellular domain that phosphorylates tyrosine amino acids. Most tyrosine kinase receptors have high-affinity for a particular growth factor, cytokine, or hormone. Tyrosine kinase receptors can be classified into families based on structural similarities, e.g. the EGF receptor family, the insulin receptor family, the PDGF receptor (PDGFR) family, the FGF receptor (FGFR) family, the VEGF receptor (VEGFR) family, the HGF receptor family, the Trk receptor family, the Eph receptor family, the LTK receptor family, the TIE receptor family, the ROR receptor family, the DDR receptor family, the RET receptor family, the KLG receptor family, the RYK receptor family, and the MuSK receptor family. Non-limiting examples of tyrosine kinase receptors relevant to the methods described herein include VEGFR2, VEGFR1, VEGFR3, bFGFR, and PDGFR.

The term "VEGF receptor" or "VEGFR" as used herein refers to a cellular receptor for VEGF, ordinarily a cell-surface receptor found on vascular endothelial cells, as well as variants thereof which retain the ability to bind VEGF. One example of a VEGF receptor is the fms-like tyrosine kinase (fit) (also known as VEGFR1), a transmembrane receptor in the tyrosine kinase family. The fit receptor comprises an extracellular domain, a transmembrane domain, and an intracellular domain with tyrosine kinase activity. The extracellular domain is involved in the binding of VEGF, whereas the intracellular domain is involved in the signal transduction. Another example of a VEGF receptor is the flk-1 receptor (also referred to as KDR or VEGFR2). VEGFR2 exhibits strong tyrosine kinase receptor activity and plays an important role in angiogenesis.

Doppel is a prion-like protein encoded by a gene, PRND, which is located near the PRNP (Prion protein coding gene) locus. For references, see, Golaniska et al., *Folia Neuropathol,* 42 (Supp. A) 47-54 (2004). Doppel expression is conserved through evolution from humans to mice, which indicates that doppel expression may play an essential function under certain physiological conditions. See, Behrens et al, *EMBO J.* 21:3652 (2002). Full-length human doppel is a 179 amino acid residue protein (UniProtKB_Q9UKY0; NCBI Ref._NP_036541.2) with a molecular weight of 14 kDa for the non-glycosylated form.

The doppel antigen used to develop the doppel-targeting molecules described herein is a glycosylated form with a molecular weight of approximately 42 kDa. Doppel protein can be in monomeric or dimeric form. Unless otherwise stated, as used herein "doppel" refers to any doppel protein, including doppel protein of mouse or human origin, including doppel protein in glycosylated or unglycosylated form, including doppel in monomeric or dimeric form.

As noted above, doppel can be expressed on the surface of endothelial cells under pathological angiogenic condition such as asthma, tuberculosis, atherosclerosis, pulmonary arterial hypertension (PAH), neoplasms, and neoplasm-related conditions. Thus, doppel-targeting molecules descried herein can be used to diagnose or treat patients with, e.g., asthma, tuberculosis, atherosclerosis, pulmonary arterial hypertension (PAH), neoplasms, and neoplasm-related conditions, by suppressing angiogenesis.

In some embodiments, the doppel-targeting molecule is an anti-doppel antibody, or related species, such as a doppel-binding antibody fragment, including, but not limited to, an antibody fragment or peptide that binds to doppel and thereby inhibits the interaction of doppel with a tyrosine kinase receptor, such as one or more of VEGFR2, VEGFR1, VEGFR3, bFGFR, and PDGFR. In specific embodiments, the doppel-targeting molecule binds to doppel and thereby inhibits the interaction of doppel with VEGFR2.

The doppel-targeting molecule may be any antibody or antibody-like molecule, including, but not limited to, a polyclonal antibody or a monoclonal antibody, or a derivative of an antibody, such as a single chain antibody, a chimeric antibody, a humanized antibody (or other species-ized antibody modified for use in another target species), a veneered antibody. The antibody may be glycosylated or glaycosylated, or have a modified glycosylation pattern.

Antibodies and antibody-like molecules suitable for use in the methods described herein can be prepared using methodology known in the art based on the guidance provided herein. Exemplary methods are illustrated in the Examples below.

For example, antibodies can be raised in a host (such as a mammalian host) using an antigen comprising either human or mouse doppel protein or a fragment thereof, such as an N-terminal or globular domain thereof, and screened for their ability to bind to doppel and inhibit its interaction with a tyrosine kinase receptor (e.g. VEGFR2). For example, polyclonal antibodies against doppel may be prepared by collecting blood from a mammal immunized with doppel and examined for the increase of desired antibodies in the serum, and by separating serum from the blood by any conventional method. For example, serum containing the polyclonal antibodies or a fraction containing the polyclonal antibodies may be isolated.

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of their respective CDRs. Thus once a set of CDR sequences (i.e., the sequence of the three CDRs for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

The term "monoclonal antibody" as used herein refers to an antibody obtained by a single clone of B-lymphocytes or by a cell into which the light and heavy chain genes of a single antibody have ben transfected. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single determinant on the antigen. Monoclonal antibodies for use in the methods described herein can be produced by methods known to those of skill in the art, for instance, immune cells can be collected from an antigen-immunized mammal and checked for an increased level of desired antibodies in the serum, and subjected to cell fusion. Immune cells used for cell fusion are typically obtained from spleen. Other suitable parental cells to be fused with the above immunocytes include, for example, myeloma cells of mammalians, such as myeloma cells having an acquired property for the selection of fused cells by drugs. The above-described immunocyte and myeloma cells can be fused according to known methods, for example, the method of Milstein et al., *Methods Enzymol.* 73:3-46 (1981)). Resulting hybridomas obtained by cell fusion may be selected by cultivating in a standard selection medium, such as HAT medium (hypoxanthine, aminopterin and thymidine containing medium). The cell culture is typically continued in the HAT medium for several days to several weeks, the time being sufficient to allow all other cells, with the exception of the desired hybridoma (non-fused cells), to die. Then, a standard limiting dilution can be performed to screen and clone a hybridoma cell producing the desired antibody.

In addition to the above methods, in which a non-human animal is immunized with an antigen for preparing hybridoma, human lymphocytes such as those infected by EB virus may be immunized with an antigen, antigen-expressing cells, or their lysates in vitro. Then, the immunized lymphocytes are fused with human-derived myeloma cells that are capable of indefinitely dividing, such as U266, to yield a hybridoma producing a desired human antibody that is able to bind to the antigen can be obtained. See, e.g. Unexamined Published Japanese Patent Application No. (JP-A) Sho 63-17688.

The obtained hybridomas can be transplanted into the abdominal cavity of a mouse and the ascites extracted. The obtained monoclonal antibodies can be purified by, for example, ammonium sulfate precipitation, a protein A or protein G column, DEAE ion exchange chromatography, or an affinity column to which the protein of the present invention is coupled.

"Humanized" forms of non-human (e.g., murine) antibodies can be obtained as chimeric antibodies, which contain minimal sequences derived from non-human immunoglobulin. In general, a humanized antibody will comprise at least one or two variable domains in which variable regions are derived from non-human immunoglobulin and framework regions (FR) correspond to a human immunoglobulin sequence. Thus, in some embodiments, the anti-doppel antibody comprises a human antibody framework region. Such antibodies can be prepared by know techniques. A humanized antibody optionally may contain at least a portion of an immunoglobulin constant region (Fc), typically that of a human immunoglobulin. See, e.g., Jones et al., *Nature* 321:522-525 (1986); Reichmann et al., *Nature* 332: 323-329 (1988); *Presta, Curr. Op. Struct. Biol.* 2:593-596 (1992).

As another method to obtain antibodies useful in the methods described herein, transgenic animals with human antibody genes may be immunized with the doppel protein, doppel protein-expressing cells, or their lysates. Resulting antibody-producing cells can be collected and fused with myeloma cells to obtain hybridoma, from which human antibodies against doppel can be prepared. Alternatively, an immune cell, such as an immunized lymphocyte, producing antibodies may be immortalized by an oncogene and used for preparing monoclonal antibodies.

Monoclonal antibodies against doppel can be also prepared using recombinant genetic engineering techniques.

See, e.g., Borrebaeck C. A. K. and Larrick J. W., Therapeutic Monoclonal Antibodies (MacMillan Publishers Ltd. (1990)). For example, a DNA encoding an antibody against doppel may be cloned from an immune cell, such as a hybridoma or an immunized lymphocyte producing the antibody, inserted into an appropriate vector, and introduced into host cells to prepare a recombinant doppel antibody.

As noted above, in accordance with any of these embodiments, the doppel-targeting molecule may be an antibody fragment that binds to doppel. As used herein, the term "antibody fragment" includes any doppel-binding fragment of an antibody or antibody-like molecule, including, but not limited to, $F_{ab}$ fragments, $F_{ab'}$ fragments, $F(_{ab}>)_2$ fragments, and smaller fragments, diabodies, etc. An antibody "fragment" may be prepared from a full-length antibody, or may be synthesized as a "fragment" for example, using recombinant techniques.

An antibody fragment useful as a doppel-targeting molecule may comprise a portion of a full-length antibody, such as its antigen-binding domain or variable region domain. Examples of suitable antibody fragments include Fab, F(ab') 2, Fv, or single chain Fv (scFv), in which Fv fragments from the heavy and light chains are ligated by an appropriate linker. (See, e.g., Huston et al., *Proc. Natl. Acad. Sci. U.S.A.* 85:5879-5883 (1988)); diabodies; linear antibodies; single-chain antibody molecules; and multispecific antibodies formed from antibody fragments.

A doppel-binding antibody fragment may be generated by treating a doppel-binding antibody with an enzyme, such as papain or pepsin. Alternatively, a gene encoding a doppel-binding antibody fragment may be constructed, inserted into an expression vector, and expressed in an appropriate host cell (see, e.g., Co et al., *J. Immunol.* 152:2968-2976 (1994); Better and Horwitz, *Methods Enzymol.* 178:476-496 (1989); Pluckthun and Skerra, *Methods Enzymol.* 178:497-515 (1989); Lamoyi, *Methods Enzymol.* 121:652-663 (1986); Rousseaux et al., *Methods Enzymol.* 121:663-669 (1986); Bird and Walker, *Trends Biotechnol.* 9:132-137 (1991)).

As used herein, the term "diabodies" refers to small antibody fragments with two antigen-binding sites, which fragments comprise a heavy chain variable domain (VH) connected to a light chain variable domain (VL) in the same polypeptide chain (VH-VL) by a linker. The linker is too short to allow pairing between the two domains on the same chain, so that the domains are forced to pair with complementary domains of another chain and create two antigen-binding sites. Diabodies are described more fully in, for example, EP 404 097; WO 93/11161; and Hollinger et al., *Proc. Natl. Acad. Sci. USA* 90:6444-6448 (1993).

As illustrated in the examples, antibodies and antibody fragments can be screened for doppel-binding activity using conventional techniques in view of the guidance provided herein. For example, measurement of absorbance, enzyme-linked immunosorbent assay (ELISA), enzyme immunoassay (EIA), radioimmunoassay (RIA), western blot assay, and/or immunofluorescence may be used to measure doppel-binding activity. For example, for ELISA, a known anti-doppel antibody can be immobilized on a plate, doppel applied to the plate, and then a sample containing a test antibody, such as culture supernatant of antibody-producing cells or purified antibodies, can be applied. Then, a secondary antibody that recognizes the primary antibody and is labeled with an enzyme, such as alkaline phosphatase, is applied, and the plate is incubated. Next, after washing, an enzyme substrate, such as nitrophenyl phosphate, is added to the plate and the absorbance is measured to evaluate the antigen binding activity of the sample. C-terminal or N-terminal fragment of doppel protein may be used as an antigen. In another example, surface plasmon resonance analysis may be used to evaluate the activity of the antibody according to the present invention.

In some embodiments, the doppel-targeting molecule binds one or more forms of doppel, such as one or more of the monomeric, dimeric, glycosylated and non-glycosylated forms discussed above. In some embodiments, the doppel-targeting molecule binds one or more forms of human doppel, such as one or more of the monomeric, dimeric, glycosylated and non-glycosylated forms discussed above. In some embodiments, the doppel-targeting molecule binds one or more forms of a non-human species of doppel, such as one or more of the monomeric, dimeric, glycosylated and non-glycosylated forms discussed above.

In some embodiments, the doppel-targeting molecule preferentially binds to one are more of the forms of doppel described above, such as preferentially binding to one or more forms of doppel described above as compared to one or more of the other forms. In some embodiments, the doppel-targeting molecule preferentially binds to one or more forms of human doppel. In some embodiments, the doppel-targeting molecule preferentially binds to one or more forms of a non-human species of doppel.

In some embodiments, the doppel-targeting molecule binds to the glycosylated form of human doppel having a molecular weight of about 42 KDa (discussed above) with greater affinity than the non-glycosylated form of doppel. In some embodiments, the doppel-targeting molecule binds to the non-glycosylated form of human doppel (approximately 14 KDa) with greater affinity than the glycosylated form of doppel (approximately 42 KDa). In some embodiments, the doppel-targeting molecule binds the dimeric form of human doppel protein (approximately 28 KDa).

In accordance with any embodiments, the doppel-targeting molecule may bind to doppel produced by any means, including, but not limited to, isolated forms of doppel, recombinant forms of human doppel, and/or doppel from doppel-transfected Huvec cell lysates, human tumor endothelial cells, etc.

In some embodiments, the doppel-targeting molecule is an antibody produced by a hybridoma cell line selected from any of 2B6, 2A8, 7A11, 7G3, 2E9, 4E3, 4H7, 2C10, 2C12, 5D3, 4D5 and 7D7, or is an antibody that has an amino acid sequence that is at least 85%, 90%, 95%, or 99% identical to an antibody produced by such a hybridoma cell line, or is a derivative of such an antibody, such as any one or more of the types of antibody derivatives discussed above, or a fragment of such an antibody or derivative thereof that binds doppel, such as any one or more of the types of antibody fragments discussed above.

Hybridoma cell lines 2B6, 2A8, 2E9, 2C10 and 2C12 were deposited with the Korean Cell Line Research Foundation under the provisions of the Budapest Treaty on Sep. 29, 2020, under the accession numbers listed in the table below.

Hybridoma cell lines 7A11, 7G3, 4E3, 4H7, 5D3, 4D5 and 7D7 were deposited with the Korean Cell Line Research Foundation under the provisions of the Budapest Treaty on Oct. 19, 2020, under the accession numbers listed in the table below.

In some embodiments, the doppel-targeting molecule is a human monoclonal antibody selected from any of A12, B2, E9, 3D5, 3D1, 4D1, and 3H9. In some embodiments, the doppel-targeting molecule has an amino acid sequence that is at least 85%, 90%, 95%, or 99% identical to A12, B2, E9, 3D5, 3D1, 4D1 or 3H9.

In some embodiments, the doppel-targeting molecule is a chimeric antibody selected from chimeric antibody 7G3 and chimeric antibody 2B6 described below. In some embodiments, the doppel-targeting molecule has an amino acid sequence that is at least 85%, 90%, 95%, or 99% identical to chimeric antibody 7G3 or chimeric antibody 2B6.

In some embodiments, the doppel-targeting molecule is a humanized antibody selected from humanized antibody 7G3 and humanized antibody 2B6 described below. In some embodiments, the doppel-targeting molecule has an amino acid sequence that is at least 85%, 90%, 95%, or 99% identical to humanized antibody 7G3 or humanized antibody 2B6.

In some embodiments, the doppel-targeting molecule is an antibody or antibody-like molecule as described above having complementarity-determining regions (CDRs) sequences that are at least 85%, 90%, 95%, 99%, or 100% identical to the CDRs of an antibody produced by any of hybridoma cell lines, e.g., clones 2B6, 2A8, 7A11, 7G3, 2E9, 4E3, 4H7, 2C10, 2C12, 5D3, 4D5, or 7D7.

In some embodiments, the doppel-targeting molecule is an antibody or antibody-like molecule as described above having CDR sequences that are at least 85%, 90%, 95%, 99%, or 100% identical to the CDRs of any of human monoclonal antibodies, e.g., A12, B2, E9, 3D5, 3D1, 4D1, or 3H9.

In some embodiments, the doppel-targeting molecule is an antibody or antibody-like molecule as described above having heavy chain variable domain sequences that are at least 85%, 90%, 95%, 99%, or 100% identical to the heavy chain variable domain sequences of an antibody produced by any of the foregoing hybridoma cell lines, e.g., clones 2B6, 2A8, 7A11, 7G3, 2E9, 4E3, 4H7, 2C10, 2C12, 5D3, 4D5, or 7D7.

In some embodiments, the doppel-targeting molecule is an antibody or antibody-like molecule as described above having heavy chain variable domain sequences that are at least 85%, 90%, 95%, 99%, or 100% identical to the heavy chain variable domain sequences of any of human monoclonal antibodies, e.g., A12, B2, E9, 3D5, 3D1, 4D1, or 3H9.

In some embodiments, the doppel-targeting molecule is an antibody or antibody-like molecule as described above having light chain variable domain sequences at least 85%, 90%, 95%, 99%, or 100% identical to the light chain variable domain sequence of an antibody produced by any of the foregoing hybridoma cell lines, e.g., clones 2B6, 2A8, 7A11, 7G3, 2E9, 4E3, 4H7, 2C10, 2C12, 5D3, 4D5, or 7D7.

In some embodiments, the doppel-targeting molecule is an antibody or antibody-like molecule as described above having light chain variable domain sequences that are at least 85%, 90%, 95%, 99%, or 100% identical to the light chain variable domain sequences of any of human monoclonal antibodies, e.g., A12, B2, E9, 3D5, 3D1, 4D1, or 3H9.

In some embodiments, the doppel-targeting molecule is an antibody or antibody-like molecule as described above having the heavy chain variable domain sequence and the light chain variable domain sequence of an antibody produced by any of the foregoing hybridoma cell lines, or of any one of the human monoclonal antibodies, or having a heavy chain variable domain sequence and a light chain variable domain sequence at least 85%, 90%, 95%, or 99% identical thereto, e.g., having the heavy chain variable domain sequence and the light chain variable domain sequence of an antibody produced by any one of clones 2B6, 2A8, 7A11, 7G3, 2E9, 4E3, 4H7, 2C10, 2C12, 5D3, 4D5, or 7D7, or having the heavy chain variable domain sequence and the light chain variable domain sequence of any one of the human monoclonal antibodies A12, B2, E9, 3D5, 3D1, 4D1 or 3H9.

In some embodiments, the doppel-targeting molecule is an antibody or antibody-like molecule as described above having framework region sequences that are at least 85%, 90%, 95%, 99%, or 100% identical to the framework region sequences of an antibody produced by any one of hybridoma cell lines, e.g., clones 2B6, 2A8, 7A11, 7G3, 2E9, 4E3, 4H7, 2C10, 2C12, 5D3, 4D5, or 7D7.

In some embodiments, the doppel-targeting molecule is an antibody or antibody-like molecule as described above having framework region sequences that are at least 85%, 90%, 95%, 99%, or 100% identical to the framework region sequences of any of human monoclonal antibodies, e.g., A12, B2, E9, 3D5, 3D1, 4D1, or 3H9.

In specific embodiments, the doppel-targeting molecule is an antibody or antibody-like molecule as described above having the heavy chain variable domain sequence, the light chain variable domain sequence, and the framework region sequence of an antibody produced by any one of clones 2B6, 2A8, 7A11, 7G3, 2E9, 4E3, 4H7, 2C10, 2C12, 5D3, 4D5, or 7D7 or has heavy chain variable domain, light chain variable domain, and framework region sequences at least 85%, 90%, 95%, or 99% identical thereto.

In specific embodiments, the doppel-targeting molecule is an antibody or antibody-like molecule as described above having the heavy chain variable domain sequence, the light chain variable domain sequence, and the framework region sequence of any of human monoclonal antibodies A12, B2, E9, 3D5, 3D1, 4D1 or 3H9, or has heavy chain variable domain, light chain variable domain, and framework region sequences at least 85%, 90%, 95%, or 99% identical thereto.

In some embodiments, the heavy chain variable region comprises a CDRH1 amino acid sequence at least 85%, 90%, 95%, 99%, or 100% identical to the CDRH1 sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the heavy chain variable region comprises a CDRH2 amino acid sequence at least 85%, 90%, 95%, 99%, or 100% identical to the CDRH2 sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the heavy chain variable region comprises a CDRH3 amino acid sequence at least 85%, 90%, 95%, 99%, or 100% identical to the CDRH3 sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the light chain variable region comprises a CDRL1 amino acid sequence at least 85%, 90%, 95%, 99%, or 100% identical to the CDRL1 sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the light chain variable region comprises a CDRL2 amino acid sequence at least 85%, 90%, 95%, 99%, or 100% identical to the CDRL2 sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the light chain variable region comprises a CDRL3 amino acid sequence at least 85%, 90%, 95%, 99%, or 100% identical to the CDRL3 sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the doppel-targeting molecule is an antibody or antibody-like molecule as described above having the heavy chain sequence, the light chain sequence, and the framework region sequence of any one of chimeric antibody 7G3, chimeric antibody 2B6, humanized antibody 7G3, or humanized antibody 2B6, or has the heavy chain, light chain, and framework region sequences at least 85%, 90%, 95%, or 99% identical thereto.

In some embodiments, the doppel-targeting molecule is an antibody or antibody-like molecule as described above having one or more or all of the following characteristics:

(a) the light chain immunoglobulin variable domain sequence comprises one or more CDRs that are at least 85%, 90%, 95%, or 99% identical to a CDR of a light chain variable domain of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9;

(b) the heavy chain immunoglobulin variable domain sequence comprises one or more CDRs that are at least 85%, 90%, 95%, or 99% identical to a CDR of a heavy chain variable domain of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9;

(c) the light chain immunoglobulin variable domain sequence is at least 85%, 90%, 95%, or 99% identical to a light chain variable domain of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9; and/or (d) the heavy chain immunoglobulin variable domain sequence is at least 85%, 90%, 95%, or 99% identical to a heavy chain variable domain of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In other embodiments, the doppel-targeting molecule is an antibody or antibody-like molecule as described above having a CDR wherein one or more amino acid residues in the CDR is substituted with another amino acid, relative to the CDR sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9. The substitution may be "conservative" in the sense of being a substitution within the same family of amino acids, based on the following family groupings:

(1) Amino acids with basic side chains: lysine, arginine, histidine.

(2) Amino acids with acidic side chains: aspartic acid, glutamic acid (3) Amino acids with uncharged polar side chains: asparagine, glutamine, serine, threonine, tyrosine.

(4) Amino acids with nonpolar side chains: glycine, alanine, valine, leucine, isoleucine, proline, phenylalanine, methionine, tryptophan, cysteine.

In other embodiments, the doppel-targeting molecule is an antibody or antibody-like molecule as described above having a CDR wherein one or more amino acid residues are added to or deleted from the CDR, relative to the CDR sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9. Such additions or deletions may occur at one or more of the N or C terminus of the CDR or at a position within the CDR.

By varying the amino acid sequence of one or more CDRs by addition, deletion or substitution of amino acids, various effects such as increased binding affinity for the target antigen may be obtained.

An antibody or antibody-like doppel-targeting molecule as described herein may have a constant region different from that of an antibody produced by any one of clones 2B6, 2A8, 7A11, 7G3, 2E9, 4E3, 4H7, 2C10, 2C12, 5D3, 4D5, or any of human monoclonal antibodies 7D7, or A12, B2, E9, 3D5, 3D1, 4D1 or 3H9. For example, doppel-targeting antibodies may be provided with Fc regions of any isotype: IgA (IgA1, IgA2), IgD, IgE, IgG (IgG1, IgG2, IgG3, IgG4) or IgM.

In some embodiments, the heavy chain constant domain sequence is at least 85%, 90%, 95%, 99%, or 100% identical to the heavy chain constant domain sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the light chain constant domain sequence is at least 85%, 90%, 95%, 99%, or 100% identical to the light chain constant domain sequence of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the heavy chain constant domain sequence and the light chain constant domain sequence is at least 85%, 90%, 95%, 99%, or 100% identical to the heavy chain constant domain sequence and the light chain constant domain sequence, respectively, of an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In specific embodiments, the doppel-targeting molecule is an antibody or antibody-like molecule as described above having CDRH1, CDRH2, CDRH3, CDRL1, CDRL2, and CDRL3 sequences at least 85%, 90%, 95%, or 99% identical to the CDRH1, CDRH2, CDRH3, CDRL1, CDRL2, and CDRL3 sequences of any one antibody produced by any one of clones 2B6, 2A8, 7A11, 7G3, 2E9, 4E3, 4H7, 2C10, 2C12, 5D3, 4D5, or 7D7, or of any one of human monoclonal antibodies A12, B2, E9, 3D5, 3D1, 4D1 or 3H9. In other specific embodiments, the doppel-targeting molecule is an antibody or antibody-like molecule as described above having a heavy chain variable region sequence, light chain variable region sequence, and, optionally, one or more of framework region sequences, heavy chain constant region sequence, and light chain constant region sequence, at least 85%, 90%, 95%, or 99% identical to the heavy chain variable region sequence, light chain variable region sequence, and, optionally, framework region sequences, heavy chain constant region sequence, and light chain constant region sequence, of any one antibody produced by any one of clones 2B6, 2A8, 7A11, 7G3, 2E9, 4E3, 4H7, 2C10, 2C12, 5D3, 4D5, or 7D7, or of any one of human monoclonal antibodies A12, B2, E9, 3D5, 3D1, 4D1 or 3H9.

In some embodiments, the doppel-targeting molecule is an antibody or antibody-like molecule as described above having a heavy chain variable domain sequence and a light chain variable domain sequence that together form an antigen binding site that binds to doppel. In some embodiments, the doppel-targeting molecule is an antibody or antibody-like molecule as described above that binds to an epitope bound by an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9. In some embodiments, the doppel-targeting molecule binds to doppel with similar specificity and sensitivity profiles as the antibodies on which they are based (e.g., an antibody produced by any one of clones 2B6, 2A8, 7A11, 7G3, 2E9, 4E3, 4H7, 2C10, 2C12, 5D3, 4D5, or 7D7, or any of human monoclonal antibodies A12, B2, E9, 3D5, 3D1, 4D1 or 3H9.

In some embodiments, the doppel-targeting molecule is a chimeric antibody or a chimeric antibody-like molecule as described above having VH and VL regions from a mouse antibody (e.g., any of 2B6, 2A8, 7A11, 7G3, 2E9, 4E3, 4H7, 2C10, 2C12, 5D3, 4D5 and 7D7) and constant regions from a human antibody. In some embodiments, the doppel-targeting molecule is a chimeric antibody or a chimeric antibody-like molecule as having constant regions from the human heavy chain from IgG1 (P01857_HUMAN-Immunoglobulin heavy constant gamma 1(IGHG1)) and human light chain from kappa (P01834_HUMAN-Immunoglobulin kappa constant (IGKC)).

In some embodiments, the doppel-targeting molecule is a humanized antibody or a humanized antibody-like molecule as described above having a heavy chain from a human antibody. In some embodiments, the doppel-targeting molecule is a humanized antibody or a humanized antibody-like molecule, as described above having a heavy chain at least about 20%, about 30%, about 40%, about 50%, about 60%, about 70%, about 80%, about 90%, or about 100% identical to the heavy chain of a murine antibody as described herein (e.g., any of 2B6, 2A8, 7A11, 7G3, 2E9, 4E3, 4H7, 2C10, 2C12, 5D3, 4D5 and 7D7). In some embodiments, the heavy chain is from a human antibody selected from the ImMunoGeneTics (IMGT) data base. In some embodiments the heavy chain is from the heavy chain genes IGHV1-46 or IGHJ4.

In some embodiments, the doppel-targeting molecule is a humanized antibody or a humanized antibody-like molecule, as described above having a light chain from a human antibody. In some embodiments, the doppel-targeting molecule is a humanized antibody or a humanized antibody-like molecule, as described above having a light chain at least about 20%, about 30%, about 40%, about 50%, about 60%, about 70%, about 80%, about 90%, or about 100% identical to the light chain of a murine antibody as disclosed herein (e.g., any of 2B6, 2A8, 7A11, 7G3, 2E9, 4E3, 4H7, 2C10, 2C12, 5D3, 4D5 and 7D7). In some embodiments, the light chain is from a human antibody selected from the IMGT data base. In some embodiments the light chain is from the light chain gene IGKV3D-1.

In some embodiments, the doppel-targeting molecule is a humanized antibody or a humanized antibody-like molecule, as described above, and has CDR regions from a mouse antibody as disclosed herein (e.g., any of 2B6, 2A8, 7A11, 7G3, 2E9, 4E3, 4H7, 2C10, 2C12, 5D3, 4D5 and 7D7).

TABLE 1

| Clone | Accession Number |
|---|---|
| 2B6 | KCLRF-BP-00490 |
| 2A8 | KCLRF-BP-00489 |
| 7A11 | KCLRF-BP-00498 |
| 7G3 | KCLRF-BP-00500 |
| 2E9 | KCLRF-BP-00493 |
| 4E3 | KCLRF-BP-00495 |
| 4H7 | KCLRF-BP-00496 |
| 2C10 | KCLRF-BP-00491 |
| 2C12 | KCLRF-BP-00492 |
| 5D3 | KCLRF-BP-00497 |
| 4D5 | KCLRF-BP-00494 |
| 7D7 | KCLRF-BP-00499 |

TABLE 2

| Light Chain CDR Sequence | | | |
|---|---|---|---|
| Antibody | CDRL1 | CDRL2 | CDRL3 |
| 2B6 | QNVDAN (SEQ ID NO: 1) | SAS (SEQ ID NO: 2) | QQYNSYPFT (SEQ ID NO: 3) |
| 2A8 | QSLLYSSNQKNY (SEQ ID NO: 4) | WAS (SEQ ID NO: 5) | QQYYSYPLT (SEQ ID NO: 6) |
| 7A11 | QSIVQSNGNTY (SEQ ID NO: 7) | KVS (SEQ ID NO: 8) | FQGSHVPLT (SEQ ID NO: 9) |
| 7G3 | SSVSSSY (SEQ ID NO: 10) | STS (SEQ ID NO: 11) | HQYHRSPLT (SEQ ID NO: 12) |
| 2E9 | RGISNY (SEQ ID NO: 13) | YTS (SEQ ID NO: 14) | QQYSKLPST (SEQ ID NO: 15) |
| 4E3 | QSLLYSSNQKNY (SEQ ID NO: 16) | WAS (SEQ ID NO: 17) | QQYYSYPLT (SEQ ID NO: 18) |
| 4H7 | QSLLYSSNQKNY (SEQ ID NO: 19) | WAS (SEQ ID NO: 20) | QQYYTYPLS (SEQ ID NO: 21) |
| 2C10 | KSISKY (SEQ ID NO: 22) | SGS (SEQ ID NO: 23) | QQHSEYPWT (SEQ ID NO: 24) |

TABLE 2-continued

| Light Chain CDR Sequence | | | |
|---|---|---|---|
| Antibody | CDRL1 | CDRL2 | CDRL3 |
| 2C12 | SSVNY (SEQ ID NO: 25) | LTS (SEQ ID NO: 26) | QQWSSNPWT (SEQ ID NO: 27) |
| 5D3 | ESVDSYGNSF (SEQ ID NO: 28) | RAS (SEQ ID NO: 29) | QQSNEDLT (SEQ ID NO: 30) |
| 4D5 | SSVNY (SEQ ID NO: 31) | LTS (SEQ ID NO: 32) | QQWSSNPWT (SEQ ID NO: 33) |
| 7D7 | TGAVTTSNY (SEQ ID NO: 34) | GTN (SEQ ID NO: 35) | ALWYSNHWV (SEQ ID NO: 36) |
| A12 | RASQSIGSYLN (SEQ ID NO: 37) | AASTLQS (SEQ ID NO: 38) | QQSYSFPWT (SEQ ID NO: 39) |
| B2 | RASQSISNYLN (SEQ ID NO: 40) | AASRLQS (SEQ ID NO: 41) | QQSYSFPWT (SEQ ID NO: 42) |
| E9 | RASQSIRNYLN (SEQ ID NO: 43) | AASNLQS (SEQ ID NO: 44) | QQSSSFPLT (SEQ ID NO: 45) |
| 3D5 | RASQSISSYLN (SEQ ID NO: 46) | AASSLQS (SEQ ID NO: 47) | QQSESFPLT (SEQ ID NO: 48) |
| 3D1 | RASQSISNWLN (SEQ ID NO: 49) | ATSSLQS (SEQ ID NO: 50) | QQSYSYPWT (SEQ ID NO: 51) |
| 4D1 | RASQSISNYLN (SEQ ID NO: 52) | AASTLQS (SEQ ID NO: 53) | QQSYSTPWT (SEQ ID NO: 54) |
| 3H9 | RASQSISNYLN (SEQ ID NO: 55) | AASTLQS (SEQ ID NO: 56) | QQSYSFPYT (SEQ ID NO: 57) |

TABLE 3

| Heavy Chain CDR Sequence | | | |
|---|---|---|---|
| Antibody | CDRH1 | CDRH2 | CDRH3 |
| 2B6 | GFTFTDYA (SEQ ID NO: 58) | ISSYYGDA (SEQ ID NO: 59) | ARRLRGAMDY (SEQ ID NO: 60) |
| 2A8 | GYSITSGYS (SEQ ID NO: 61) | IHYSGST (SEQ ID NO: 62) | ARLYGWYFDV (SEQ ID NO: 63) |
| 7A11 | GYTFTSYW (SEQ ID NO: 64) | IYPSDSYT (SEQ ID NO: 65) | TRSMIT (SEQ ID NO: 66) |
| 7G3 | GYSFTDYI (SEQ ID NO: 67) | INPYYGST (SEQ ID NO: 68) | ARRNYYGNYDAMDY (SEQ ID NO: 69) |
| 2E9 | GFTFTDYY (SEQ ID NO: 70) | IRNKANGYTT (SEQ ID NO: 71) | ARGDGYYGYFDY (SEQ ID NO: 72) |
| 4E3 | GFTFTDYY (SEQ ID NO: 73) | IRNKANGYTT (SEQ ID NO: 74) | ARGDGYYGYFDY (SEQ ID NO: 75) |
| 4H7 | GYSITSGYS (SEQ ID NO: 76) | IHYSGNT (SEQ ID NO: 77) | AMRTYYYGPLDY (SEQ ID NO: 78) |
| 2C10 | GDSITSGY (SEQ ID NO: 79) | IRYSGSA (SEQ ID NO: 80) | ARYPYYGSYWYFDV (SEQ ID NO: 81) |
| 2C12 | GFSLTGYG (SEQ ID NO: 82) | IWGDGNT (SEQ ID NO: 83) | ARDRDYYGSIPFAY (SEQ ID NO: 84) |
| 5D3 | GYSFTGYN (SEQ ID NO: 85) | IDPYYGGS (SEQ ID NO: 86) | ARVRYDYSLMDY (SEQ ID NO: 87) |
| 4D5 | GFSLTSYG (SEQ ID NO: 88) | IWAAGST (SEQ ID NO: 89) | ARRDGNYRGFAY (SEQ ID NO: 90) |

TABLE 3-continued

| Heavy Chain CDR Sequence | | | |
|---|---|---|---|
| Antibody | CDRH1 | CDRH2 | CDRH3 |
| 7D7 | GDSFTRYW (SEQ ID NO: 91) | IYPGNSDT (SEQ ID NO: 92) | TRGGYGPY (SEQ ID NO: 93) |
| A12 | SYAMS (SEQ ID NO: 94) | AISSDGGSTYYADSVKG (SEQ ID NO: 95) | RRLWSYSFDY (SEQ ID NO: 96) |
| B2 | DYAMS (SEQ ID NO: 97) | AISSSGGSTYYADSVKG (SEQ ID NO: 98) | LYYTYEVLDI (SEQ ID NO: 99) |
| E9 | SYYMH (SEQ ID NO: 100) | RISPGGGGTIYAQKFQG (SEQ ID NO: 101) | AQSEGLSYYFDV (SEQ ID NO: 102) |
| 3D5 | DYAMS (SEQ ID NO: 103) | RISSSGSSKYYADSVKG (SEQ ID NO: 104) | WGSYGYGLVYYFDV (SEQ ID NO: 105) |
| 3D1 | DYAMS (SEQ ID NO: 106) | RISGSGGTKYYADSVKG (SEQ ID NO: 107) | HQVYWALDV (SEQ ID NO: 108) |
| 4D1 | DYAMS (SEQ ID NO: 109) | AISSSGGEKYYADSVKG (SEQ ID NO: 110) | HGYGQEYYYFDV (SEQ ID NO: 111) |
| 3H9 | SYAMS (SEQ ID NO: 112) | GISGSGSRTDYADSVKG (SEQ ID NO: 113) | VYTYTRGFAFDL (SEQ ID NO: 114) |

TABLE 4

| Light Chain Variable Region Sequence for 2B6, 2A8, 7A11, 7G3, 2E9, 4E3, 4H7, 2C10, 2C12, 5D3, 4D5 and 7D7 and full Light Chain Sequence for A12, B2, E9, 3D5, 3D1, 4D1, and 3H9 | |
|---|---|
| Ab | Light Chain Variable Region Sequence or full Light Chain Sequence |
| 2B6 | DIVMTQSQKFMSTSVGDRVSVTCKASQNVDANVAWYQQKPGQSPKALIYSASYRYSGV PYRFTGSGSGTDFTLTISNVQSADLAEYFCQQYNSYPFTFGSGTKLELK (SEQ ID NO: 115) |
| 2A8 | DIVMSQSPSSLAVSVGEKVTMNCKSSQSLLYSSNQKNYLAWYQQKPGQSPKLLIYWAS TRESGVPDRFTGSGSGTDFTLTISSVKAEDLAVYYCQQYYSYPLTFGAGTKLELK (SEQ ID NO: 116) |
| 7A11 | DVLMTQTPLSLPVSLGDQASISCRSSQSIVHSNGNTYLEWYLQKPGQSPKVLIYKVSN RFSGVPDRFSGSGSGTDFTLKINRVEAEDLGVYYCFQGSHVPLTFGAGTKLELK (SEQ ID NO: 117) |
| 7G3 | QIVLTQSPAIMSASLGERVTMTCTASSSVSSSYLHWYQQKPGSSPKLWIYSTSNLASG VPARFSGSGSGTSYSLTISSMEAEDTATYYCHQYHRSPLTFGAGTKLELK (SEQ ID NO: 118) |
| 2E9 | DVQMTQTTSSLSASLGDRVTISCSASRGISNYLNWYQQKPDGTVKLLIYYTSSLHSGV PPRFSGSGSGTDYSLTISNLEPEDIATYYCQQYSKLPSTFGGGTKVEIK (SEQ ID NO: 119) |
| 4E3 | DIVMSQSPSSLAVSVGEKVTMNCKSSQSLLYSSNQKNYLAWYQQKPGQSPKLLIYWAS TRESGVPDRFTGSGSGTDFTLTISSVKAEDLAVYYCQQYYSYPLTFGAGTKLELK (SEQ ID NO: 120) |
| 4H7 | DIVMSQSPSSLPVSVGEKVTMSCKSSQSLLYSSNQKNYLAWYQQKPGQSPKVLIYWAS TRESGVPDRFTGSGSGTDFTLTISSVKAEDLAVYYCQQYYTYPLSFGAGTKLELK (SEQ ID NO: 121) |
| 2C10 | DVQITQSPSYLAASPGETITLNCRASKSISKYLAWYQEKPGKTNKLLIYSGSTLQSGI PSRFSGSGSGSDFTLTISSLEPEDFAMYYCQQHSEYPWTFGGGTKLEIK (SEQ ID NO: 122) |
| 2C12 | QIVLTQSPALMSASPGEKVTMTCSASSSVNYIYWYQQKPGSSPKPWIYLTSNLASGVP ARFSGSGSGTSYSLTISSMEAEDAATYYCQQWSSNPWTFGGGTKLEIK (SEQ ID NO: 123) |
| 5D3 | DIVLTQSPASLAVSLGQRATISCRASESVDSYGNSFMHWYQQKPGQPPKLLIYRASNL ESGIPARFSGSGSRTDFTLTINPVEADDVASYYCQQSNEDLTFGAGTKLELK (SEQ ID NO: 124) |

TABLE 4-continued

Light Chain Variable Region Sequence for 2B6, 2A8, 7A11, 7G3, 2E9, 4E3, 4H7, 2C10, 2C12, 5D3, 4D5 and 7D7 and full Light Chain Sequence for A12, B2, E9, 3D5, 3D1, 4D1, and 3H9

| Ab | Light Chain Variable Region Sequence or full Light Chain Sequence |
|---|---|
| 4D5 | QIVLSQSPALMSASPGEKVTMTCSASSSVNYIYWYQQKPGSSPKPWIYLTSNLASGVP ARFSGSGSGTSYSLTISSMEAEDAATYYCQQWSSNPWTFGGGTKLEIK (SEQ ID NO: 125) |
| 7D7 | QAVVTQESALTTSPGETVTLTCRSSTGAVTTSNYANWVQEKPDHLFTGLIGGTNNRAP GVPARFSGSLIGDKAALTITGAQTEDEAIYFCALWYSNHWVFGGGTKLTVL (SEQ ID NO: 126) |
| A12 | DIQMTQSPSSLSASVGDRVTITCRASQSIGSYLNWYQQKPGKAPKLLIYAASTLQSGV PSRFSGSGSGTDFTLTISSLQPEDFATYYCQQSYSFPWTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 127) |
| B2 | DIQMTQSPSSLSASVGDRVTITCRASQSISNYLNWYQQKPGKAPKLLIYAASRLQSGV PSRFSGSGSGTDFTLTISSLQPEDFATYYCQQSYSFPWTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 128) |
| E9 | DIQMTQSPSSLSASVGDRVTITCRASQSIRNYLNWYQQKPGKAPKLLIYAASNLQSGV PSRFSGSGSGTDFTLTISSLQPEDFATYYCQQSSSFPLTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 129) |
| 3D5 | DIQMTQSPSSLSASVGDRVTITCRASQSISSYLNWYQQKPGKAPKLLIYAASSLQSGV PSRFSGSGSGTDFTLTISSLQPEDFATYYCQQSESFPLTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 130) |
| 3D1 | DIQMTQSPSSLSASVGDRVTITCRASQSISNWLNWYQQKPGKAPKLLIYATSSLQSGV PSRFSGSGSGTDFTLTISSLQPEDFATYYCQQSYSYPWTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 131) |
| 4D1 | DIQMTQSPSSLSASVGDRVTITCRASQSISNYLNWYQQKPGKAPKLLIYAASTLQSGV PSRFSGSGSGTDFTLTISSLQPEDFATYYCQQSYSTPWTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 132) |
| 3H9 | DIQMTQSPSSLSASVGDRVTITCRASQSISNYLNWYQQKPGKAPKLLIYAASTLQSGV PSRFSGSGSGTDFTLTISSLQPEDFATYYCQQSYSFPYTFGQGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 133) |

TABLE 5

Heavy Chain Variable Region Sequence for 2B6, 2A8, 7A11, 7G3, 2E9, 4E3, 4H7, 2C10, 2C12, 5D3, 4D5 and 7D7 and full Heavy Chain Sequence for A12, B2, E9, 3D5, 3D1, 4D1, and BH9

| Ab | Heavy Chain Variable Region Sequence Or full Heavy Chain Sequence |
|---|---|
| 2B6 | QVQLQQSGAELVRPGVSVKLSCKFSGFTFTDYAMHWVRQSHAKSLAWIGVISSYYGD ASYNQKFTGKATMTVDKSSSTAYMELARLTSEDSAIYYCARRLRGAMDYWGQGTSVT VSS (SEQ ID NO: 134) |
| 2A8 | DVQLQESGPDLVKPSQSLSLTCTVTGYSITSGYSWHWIRQFPGNKLEWMGYIHYSGS TNYNPSLKSRISITRDTSKNQFFLQLNSVTTEDTATYYCARLYGWYFDVWGAGTTVT VSS (SEQ ID NO: 135) |

TABLE 5-continued

Heavy Chain Variable Region Sequence for 2B6, 2A8, 7A11, 7G3, 2E9, 4E3, 4H7, 2C10, 2C12, 5D3, 4D5 and 7D7 and full Heavy Chain Sequence for A12, B2, E9, 3D5, 3D1, 4D1, and BH9

| Ab | Heavy Chain Variable Region Sequence Or full Heavy Chain Sequence |
|---|---|
| 7A11 | QVQLQQPGAELVRPGASVKLSCKASGYTFTSYWINWVKQRPGQGLEWIGNIYPSDSYTNYNQKFKDKATLTVDKSSSTAYMQLSSPTSEDSAVYYCTRSMITWGQGTTLTVSS (SEQ ID NO: 136) |
| 7G3 | EIQLQQTGPELVKPGASVKISCKASGYSFTDYIMLWVKQSHGKSLEWIGNINPYYGSTSYNLKFKGKATLTVDKSSSTAYMQLNSLTSEDSAVYYCARRNYYGNYDAMDYWGQGTSVTVSS (SEQ ID NO: 137) |
| 2E9 | EVKLVESGGDLVQPGGSLRLSCATSGFTFTDYYMTWVRQFPGKALEWLGFIRNKANGYTTEYSASVKGRFTISRDNSQSILYLQMNTLRAEDSATFYCARGDGYYGYFDYWGQGTTLTVSS (SEQ ID NO: 138) |
| 4E3 | EVKLVESGGDLVQPGGSLRLSCATSGFTFTDYYMTWVRQFPGKALEWLGFIRNKANGYTTEYSASVKGRFTISRDNSQSILYLQMNTLRAEDSATFYCARGDGYYGYFDYWGQGTTLTVSS (SEQ ID NO: 139) |
| 4H7 | DVQLQESGPDLVKPSQSLSLTCTVTGYSITSGYSWHWIRQFPGNKLEWMGYIHYSGNTNYNPSLKSRISITRDTSKNQFFLQLNSVTTEDTATYSCAMRTYYYGPLDYWGQGTTLTVSS (SEQ ID NO: 140) |
| 2C10 | EVQLQESGPSLVKPSQTLSLTCSVTGDSITSGYWNWIRKFPGNKLEYMGYIRYSGSAYYNPSLKSRISITRDTSKNQYYLQLNSVTTEDTATYYCARYPYYGSYWYFDVWGAGTTVTVSS (SEQ ID NO: 141) |
| 2C12 | QVQLKESGPGLVAPSQSLSITCTVSGFSLTGYGVNWVRQPPGKGLEWLGMIWGDGNTDYNSALKSRLSISKDNSKSQVFLKMNSLQTDDTARYYCARDRDYYGSIPFAYWGQGTLVTVSA (SEQ ID NO: 142) |
| 5D3 | EVQLKQSGPELEKPGASVKISCKASGYSFTGYNMNWVKQSNGKSLEWIGNIDPYYGGSTYNQKFKGKATLTVDKSSSTAYMQLKSLTSEDSAVYYCARVRYDYSLMDYWGQGTSVTVSS (SEQ ID NO: 143) |
| 4D5 | QVQLKESGPGLVAPSQSLSITCTVSGFSLTSYGVHWVRQPPGKGLEWLGVIWAAGSTNYNSALMSRLSISKDNSKSQVFLKMNSLQTDDTAMYYCARRDGNYRGFAYWGQGTLVTVSA (SEQ ID NO: 144) |
| 7D7 | EVQLQESGTVLARPGASVKMSCKASGDSFTRYWMHWVKQRPGQGLEWIGGIYPGNSDTRYNQKFKGKAKLTAVTSASTAYMELSSLTNEDSAVYYCTRGGYGPYWGQGTTLTVSS (SEQ ID NO: 145) |
| A12 | EVQLVESGGGLVQPGGSLRLSCAASGFTFSSYAMSWVRQAPGKGLEWVSAISSDGGSTYYADSVKGRFTISRDNSKNTLYLQMNSLRAEDTAVYYCAKRRLWSYSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 146) |
| B2 | EVQLVESGGGLVQPGGSLRLSCAASGFTFSDYAMSWVRQAPGKGLEWVSAISSSGGSTYYADSVKGRFTISRDNSKNTLYLQMNSLRAEDTAVYYCAKLYYTYEVLDIWGQGTFVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 147) |
| E9 | QVQLVQSGAEVKKPGSSVKVSCKASGGTFSSYYMHWVRQAPGQGLEWMGRISPGGGGTIYAQKFQGRVTITADESTSTAYMELSSLRSEDTAVYYCARAQSEGLSYYFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 148) |

TABLE 5-continued

Heavy Chain Variable Region Sequence for 2B6, 2A8, 7A11, 7G3, 2E9, 4E3, 4H7, 2C10, 2C12, 5D3, 4D5 and 7D7 and full Heavy Chain Sequence for A12, B2, E9, 3D5, 3D1, 4D1, and BH9

| Ab | Heavy Chain Variable Region Sequence Or full Heavy Chain Sequence |
|---|---|
| 3D5 | EVQLVESGGGLVQPGGSLRLSCAASGFTFSDYAMSWVRQAPGKGLEWVSRISSSGSSKYYADSVKGRFTISRDNSKNTLYLQMNSLRAEDTAVYYCAKWGSYGYGLVYYFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 149) |
| 3D1 | EVQLVESGGGLVQPGGSLRLSCAASGFTFSDYAMSWVRQAPGKGLEWVSRISGSGGTKYYADSVKGRFTISRDNSKNTLYLQMNSLRAEDTAVYYCAKHQVYWALDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 150) |
| 4D1 | EVQLVESGGGLVQPGGSLRLSCAASGFTFSDYAMSWVRQAPGKGLEWVSAISSSGGEKYYADSVKGRFTISRDNSKNTLYLQMNSLRAEDTAVYYCAKHGYGQEYYYFDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 151) |
| 3H9 | EVQLVESGGGLVQPGGSLRLSCAASGFTFSSYAMSWVRQAPGKGLEWVSGISGSGSRTDYADSVKGRFTISRDNSKNTLYLQMNSLRAEDTAVYYCAKVYTYTRGFAFDLWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 152) |

TABLE 6

| Clone | $K_D$ (M) value |
|---|---|
| 2B6 | $2.921 \times 10^{-10}$ |
| 2A8 | $1.483 \times 10^{-8}$ |
| 7A11 | $2.532 \times 10^{-10}$ |
| 7G3 | $1.057 \times 10^{-8}$ |
| 2E9 | $4.051 \times 10^{-9}$ |
| 4E3 | $2.474 \times 10^{-9}$ |
| 4H7 | $2.870 \times 10^{-11}$ |
| 2C10 | $8.759 \times 10^{-9}$ |
| A12 | $9.200 \times 10^{-9}$ |
| B2 | $7.990 \times 10^{-9}$ |
| E9 | $4.410 \times 10^{-9}$ |
| 3D5 | $5.380 \times 10^{-8}$ |
| 3D1 | $3.080 \times 10^{-10}$ |
| 4D1 | $2.660 \times 10^{-7}$ |
| 3H9 | $2.800 \times 10^{-8}$ |

TABLE 7

| | Doppel protein amino acid sequence |
|---|---|
| Human PRND | MRKHLSWWWL ATVCMLLFSH LSAVQTRGIK HRIKWNRKAL PSTAQITEAQ VAENRPGAFI KQGRKLDIDF GAEGNRYYEA NYWQEPDGIH YNGCSEANVT KEAPVTGCIN ATQAANQEF QKPDKLHQQ VLWRLVQELC SLKHCEFWLE RGHHHHHH (SEQ ID NO: 153) |
| Mouse PRND | MKNRLGTWWV AILCMLLASH LSTVKARGIK HRFKWNRKVL PSSGGQITEA RVAENRPGAF IKQGRKLDID FGAEGNRYYA ANYWQFPDGI YYEGCSEANV TKEMLVTSCV NATQAANQAE FSREKQDSKL HQRVLWRLIK EICSAKHCDF WLERGHHHHHH (SEQ ID NO: 154) |

Additional doppel-targeting molecules can be identified by screening methods, such as those described below and illustrated in the examples below. Suitable methods may include assessing the binding of a test molecule to a doppel protein (or a fragment thereof that forms a complex with a tyrosine kinase inhibitor (e.g. VEGFR2)) as illustrated in the examples below. Such methods may additionally or alternatively include culturing endothelial cells where doppel and the tyrosine kinase inhibitor constitutively interact with each other in the presence or absence of a test agent that binds the doppel protein or fragment thereof and detecting one or more of the internalization of the tyrosine kinase inhibitor and/or the degradation of the tyrosine kinase inhibitor, and selecting a test molecule that inhibits the internalization of the tyrosine kinase inhibitor and/or promotes the degradation of the tyrosine kinase inhibitor, as compared with the internalization and/or degradation detected in the absence of the test molecule. Additionally or alternatively, doppel-blocking activity can be assessed, for example, by assaying the inhibition of phosphorylation and degradation of the tyrosine kinase inhibitor. Additionally or alternatively, doppel-blocking activity can be assessed, for example, by assaying the suppression of endothelial cell sprouting, which can be assessed, for example, by assaying the sprout number formed in endothelial cell spheroids and comparing the number of sprouts arising in a control group. Various methods and embodiments are illustrated in the examples below.

Any doppel protein can be used to assess binding of the test molecule. In specific embodiments, the doppel protein or fragment thereof forms a complex with the target tyrosine kinase inhibitor, such as VEGFR2 protein.

Any medium may be used for culturing endothelial cells where doppel and the tyrosine kinase inhibitor constitutively interact with each other in the presence or absence of a test agent. For example, cell extracts, cell culture supernatants, products of fermenting microorganism, extracts of marine organisms, plant extracts, etc., can be used.

Also described herein are compositions comprising one or more doppel-targeting molecules as described herein. In some embodiments, the compositions comprise one or more doppel-targeting molecules and a pharmaceutically acceptable excipient or carrier, such as a carrier suitable for the intended route of administration.

The composition may be prepared for any route of administration, including, but not limited to, any oral, parenteral, or local route of administration. In some embodiments, the composition is suitable for injection or infusion, such as for intravenous injection or infusion, such as being prepared as a sterile composition for injection or infusion. In other embodiments, the composition is suitable for oral administration, such as being prepared in a liquid or solid oral dosage form (such as a solution, syrup, powder, granule, tablet, capsule, suspension, emulsion, or oral spray). In other embodiments, the pharmaceutical composition is suitable for inhalation, such as being in the form of a solution or powder suitable for nasal or peroral inhalation. In other embodiments, the pharmaceutical composition is suitable for rectal or vaginal administration, such as being in a suppository formulation. In other embodiments, the composition is suitable for topical or transdermal administration, such as being in a solution, emulsion, gel, or patch. Appropriate components and excipients for such compositions are known in the art.

Thus, in some embodiments, the doppel-targeting molecule is formulated for oral administration, subcutaneous injection, intravenous injection or infusion, intraocular injection, intradermal injection, intramuscular injection, intraperitoneal injection, intratracheal administration, inhalation, intranasal administration, sublingual administration, buccal administration, rectal administration, vaginal administration, or topical administration.

In some embodiments, the doppel-targeting molecule is formulated for intravenous injection. Antibodies and antibody fragments typically are administered by intravenous injection to avoid degradation in the digestive tract, but could be formulated for oral delivery by, for example, being formulated in a manner that protects them from digestive enzymes, such as by using formulation techniques that are known in the art.

Examples of formulations for parenteral administration include sterilized aqueous solutions, water-insoluble solutions, suspensions, emulsions, lyophilized formulations, and suppositories. Non-aqueous solutions and suspensions may include, for example, propylene glycol, polyethylene glycol, a plant oil such as olive oil, or injectable ester such as ethyl oleate. A base for a suppository formulation may include, for example, witepsol, macrogol, Tween 61, cacao butter, laurin butter, glycerogelatin or the like.

Formulations for oral delivery may comprise a poloxamer, labrasol, polyethylene glycol, and mixtures thereof.

In some embodiments, the composition comprises an effective amount of a doppel-targeting molecule to interfere with the interaction of doppel and a tyrosine kinase receptor, such as VEGFR2, VEGFR1, VEGFR3, bFGFR, and PDGFR. In some embodiments, the composition comprises an effective amount of a doppel-targeting molecule to decrease pathological angiogenesis. In some embodiments, the composition comprises an effective amount of a doppel-targeting molecule to decrease tumor angiogenesis. In some embodiments, the composition comprises an effective amount of a doppel-targeting molecule to decrease pathological vasculature. In some embodiments, the composition comprises an effective amount of a doppel-targeting molecule to decrease tumor vasculature. In some embodiments, the composition comprises an effective amount of a doppel-targeting molecule to decrease tumor angiogenesis.

In some embodiments, the composition comprises an effective amount of a doppel-targeting molecule to decrease angiogenesis associated with asthma. In some embodiments, the composition comprises an effective amount of a doppel-targeting molecule to decrease angiogenesis associated with tuberculosis. In some embodiments, the composition comprises an effective amount of a doppel-targeting molecule to decrease angiogenesis associated with atherosclerosis. In some embodiments, the composition comprises an effective amount of a doppel-targeting molecule to decrease angiogenesis associated with pulmonary arterial hypertension (PAH). In some embodiments, the composition comprises an effective amount of a doppel-targeting molecule to decrease angiogenesis associated with a neoplasm or neoplasm-related condition.

In some embodiments, the compositions are effective to evoke a therapeutic response in tumoral endothelial cells.

In some embodiments, the compositions are effective to detect tumoral endothelial cells, such as when the doppel-targeting molecule includes or is conjugated to a detectable label.

In some embodiments, the compositions are effective to evoke a therapeutic response to a neoplasm or a neoplasm-related condition, such as breast carcinomas, lung carcinomas, gastric carcinomas, esophageal carcinomas, colorectal carcinomas, liver carcinomas, ovarian carcinomas, arrhenoblastomas, cervical carcinomas, endometrial carcinomas, endometrial hyperplasias, endometriosis, fibrosarcomas, choriocarcinomas, head and neck cancers, nasopharyngeal carcinomas, laryngeal carcinomas, hepatoblastomas, Kaposi's sarcomas, melanomas, skin carcinomas, hemangiomas, cavernous hemangiomas, hemangioblastomas, pancreas carcinomas, retinoblastomas, astrocytomas, glioblastomas, Schwannomas, oligodendrogliomas, medulloblastomas, neuroblastomas, rhabdomyosarcomas, osteogenic sarcomas, leiomyosarcomas, urinary tract carcinomas, thyroid carcinomas, Wilm's tumor, renal cell carcinomas, prostate carcinomas, abnormal vascular proliferation associated with phakomatoses, edemas (such as that associated with brain tumors), and/or Meigs' syndrome.

In some embodiments, the compositions disclosed herein are used for inhibiting angiogenesis in a subject in need thereof. In some embodiments, the subject is suffering from or at risk of developing a disease or condition involving doppel-tyrosine kinase receptor signaling (such as doppel-VEGFR2 signaling), such as a tumor or cancer or a disease or condition associated with increased vascularization, such as asthma, tuberculosis, atherosclerosis, pulmonary arterial hypertension (PAH), or a neoplasm or neoplasm-related condition.

As discussed above, the doppel-targeting molecules and compositions described herein are useful for inhibiting pathological angiogenesis and treating related diseases or conditions, in a subject in need thereof. Thus, such uses and methods are provided herein.

The term "subject" as used herein refers to any mammal, including, but not limited to, human, feline, murine, canine, equine, simian, or other species. In some embodiments, the subject is a human.

As used herein, "treating" includes reducing, slowing, or retarding pathological angiogenesis (or tumorigenesis), even if some pathological angiogenesis (or tumorigenesis) still occurs, and/or reducing, slowing, or retarding increased vasculature even if some pathological increased vasculature still occurs.

The doppel-targeting molecules and compositions described herein are useful in inhibiting pathological angiogenesis in subjects with a disease or condition involving doppel or doppel-tyrosine kinase receptor signaling, or a disease or condition indicated by increased vascularization. Non-limiting examples of such diseases or conditions include tumors, cancers, such as, but not limited to, angiogenic cancers; atherosclerosis; tuberculosis; asthma, and pulmonary arterial hypertension (PAH). Thus, the disclosed methods and doppel-targeting molecules and/or compositions may be useful for treating various neoplastic and non-neoplastic diseases and disorders.

The doppel-targeting molecules and compositions disclosed herein are also useful in generating a therapeutic response against tumoral endothelial cells (TECs) and, thus, in the treatment of diseases or conditions characterized by the presence of these cells.

The doppel-targeting molecule and compositions described herein are useful in treating neoplasms and neoplasm-related conditions.

The term "neoplasm" as used herein refers to an abnormal growth of tissue, which upon formation of a mass is known as a tumor. Neoplasms may be benign or malignant. Malignant neoplasms are generally referred to as cancer.

Neoplasms and neoplasm-related conditions that are amenable to treatment include breast carcinomas, lung carcinomas, gastric carcinomas, esophageal carcinomas, colorectal carcinomas, liver carcinomas, ovarian carcinomas, arrhenoblastomas, cervical carcinomas, endometrial carcinomas, endometrial hyperplasias, endometriosis, fibrosarcomas, choriocarcinomas, head and neck cancers, nasopharyngeal carcinomas, laryngeal carcinomas, hepatoblastomas, Kaposi's sarcomas, melanomas, skin carcinomas, hemangiomas, cavernous hemangiomas, hemangioblastomas, pancreas carcinomas, retinoblastomas, astrocytomas, glioblastomas, Schwannomas, oligodendrogliomas, medulloblastomas, neuroblastomas, rhabdomyosarcomas, osteogenic sarcomas, leiomyosarcomas, urinary tract carcinomas, thyroid carcinomas, Wilm's tumor, renal cell carcinomas, prostate carcinomas, abnormal vascular proliferation associated with phakomatoses, edemas (such as that associated with brain tumors), and Meigs' syndrome.

Thus, the doppel-targeting antibodies described herein (and related doppel-binding molecules) are useful, for example, in treating, for example, a disease or a condition selected from cancer, atherosclerosis, tuberculosis, asthma, pulmonary arterial hypertension (PAH) in a subject in need thereof, or for treating a neoplasm or neoplasm-related condition, such as breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and Meigs' syndrome.

Thus, provided herein are doppel-targeting molecules and compositions comprising them for use in methods of inhibiting pathological angiogenesis in a subject in need thereof, such as a subject suffering from or at risk of developing any one or more of the conditions mentioned above, as well as such methods. The uses and methods comprise administering an effective amount of a doppel-targeting molecule or compositions as described herein to a subject in need thereof. In some embodiments, the effective amount is effective to interfere with the interaction of doppel and a tyrosine kinase receptor, such as VEGFR2, VEGFR1, VEGFR3, bFGFR, or PDGFR. In specific embodiments, the effective amount is effective to interfere with the interaction of doppel and VEGFR2. In some embodiments, the effective amount is effective to decrease the vasculature of a tumor. In some embodiments, the effective amount is effective to evoke a therapeutic response in tumoral endothelial cells. In some embodiments, the effective amount is effective to reducing, slowing, or retarding pathological angiogenesis or tumorigenesis. In some embodiments, the effective amount is effective to decrease angiogenesis associated with asthma. In some embodiments, the effective amount is effective to decrease angiogenesis associated with tuberculosis. In some embodiments, the effective amount is effective to decrease angiogenesis associated with atherosclerosis. In some embodiments, the effective amount is effective to decrease angiogenesis associated with pulmonary arterial hypertension (PAH). In some embodiments, the effective amount is effective to decrease angiogenesis associated with a neoplasm or neoplasm-related disorder.

The doppel-targeting molecules may be administered via any route of administration, including, but not limited to, any parenteral or local route of administration. In some embodiments, the method comprises administering the doppel-targeting molecule by oral administration, subcutaneous injection, intravenous injection or infusion, intraocular injection, intradermal injection, intramuscular injection, intraperitoneal injection, intratracheal administration, inhalation, intranasal administration, sublingual administration, buccal administration, rectal administration, vaginal administration, or topical administration.

In some embodiments, the method comprises administering the doppel-targeting molecule by oral administration. In some embodiments, the method comprises administering the doppel-targeting molecule by intravenous injection.

In some embodiments, the methods include treating the subject with an additional therapy. For example, treatment methods may include administering a chemotherapeutic agent to the subject, or providing radiation therapy. As used herein, the term chemotherapeutic agent refers to a molecule useful to treat cancer, such as a small molecule chemical compound used to treat cancer. Non-limiting examples of chemotherapeutic agents include but are not limited to alkylating agents, anti-metabolites, anti-tumor antibiotics, plant alkaloids/microtubule inhibitors, DNA linking agents, biologics, bisphosphonates, hormones, and other drugs known to be useful to treat cancer. Non-limiting examples of chemotherapeutic agents include aminoglutethimide, amsacrine, anastrozole, asparaginase, beg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

EXAMPLES

The following examples illustrate specific embodiments, and are illustrative only.

Example 1: Sorting of Tumoral Endothelial Cells (TEC) for Evaluating Doppel Expression This example describes methods of purifying endothelial cells from different tumor tissue types.

Tumoral endothelial cells were isolated using a double marker following a published procedure with some modifications. Briefly, tumors were grown subcutaneously in the flank of $C_3H$/HeN mice and resected, minced using two surgical blades, and digested in 9 mL collagenase and 1 mL dispase solution per gram of tissue. Tissues were incubated for 30 minutes in a 37° C. water bath, under continuous agitation. Subsequently, 75 uL DNaseI solution per 10 ml cell suspension was added and incubated for another 30 minutes at 37° C. with continuous agitation. Digested tissues were sieved through a 100-μm cell strainer and single cells were separated. Cells were collected by centrifugation at 400×g for 7 min at room temperature. To remove red blood cells, granulocytes, nonvital cells and cell debris, the cells were resuspended in 10 mL Ficoll separation medium (per gram of starting material) and carefully layered in the suspension on 7.5 mL Ficoll-Paque (pre-warmed to room temperature). The interphase-containing viable cells were transferred into a fresh tube. Cells were collected into FACS tubes, and incubated with anti-mouse CD31-PE and anti-mouse CD34-FITC antibodies (at a final concentration of 2 μg/mL). FACS machine was prepared by adjusting conditions with a sheath fluid pressure of 29.9 psi, a sorting frequency of 44 kHz, and a plate voltage of 3,500 V. Collected cells were suspended in 10 ml ECGM containing 10% FBS and centrifuged. Then cells were plated in 0.2% gelatin-coated 100 mm dishes and cultured overnight in normal ECGM supplemented. The next day, the media was replaced with supplemented ECGM containing 10% FBS. Cells were grown until confluent.

Example 2: Western Blotting of Cells for Detecting Doppel Expression

Figure 3:
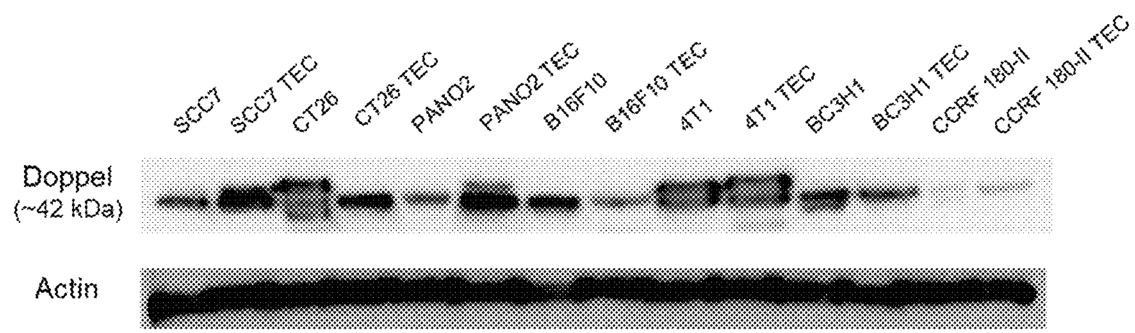
FIG. 3 shows doppel expression on tumor cells and tumor endothelial cells.

Tumor cells and tumor endothelial cells were cultured on 6 well until fluent. Cells were washed with PBS 2 times and treated with lysis buffer (RIPA buffer containing protease inhibitors and phosphatase inhibitors). Cell lysates were collected and centrifuged with 15,000 rpm for 15 mins. Supernatant were collected and kept in −80 degree until analysis. 50 μg of each protein was loaded to lane and expression of doppel was confirmed by following general SDS-PAGE protocol. The results show that doppel is expressed on both cancer cells and tumor endothelial cells. Doppel expression level depends on the type of tumors and generally tumor endothelial cells express more doppel compared to cancer cells. CCRF 180-11 expressed less doppel both for cancer cells and endothelial cells compared to other types of cancer (FIG. 3).

Example 3: Measurement of Binding Affinity Between Doppel and Anti-Doppel Monoclonal Antibody This example describes a method of assessing the dissociation rate constant between doppel and anti-doppel monoclonal antibodies.

Affinity measurements of anti-doppel monoclonal antibodies produced by the clones described herein with Prnp and Prnd (doppel) were performed by the surface plasmon resonance on a BIAcore T100 (GE Healthcare). Using the standard EDAC-NHS coupling method, recombinant proteins were immobilized at a density of 4000-7000 onto a sensor chip (GE Healthcare). Measurements were performed at a flow rate of 20 μL/min, and 50 mM NaOH was used to regenerate the chip surface after each cycle of analysis. Each concentration was analyzed in duplicate. Kinetic analysis of the data obtained was performed using BIAcore T100 evaluation software (GE Healthcare).

The antibody produced by clone 4H7 showed the highest binding affinity value while the antibody produced by clone 2A8 showed the lowest binding affinity value (FIG. 4 and Table 6).

Binding affinity was also derived using general ELISA assay. Doppel proteins were immobilized on ELISA well and binding of antibodies produced by clones 2B6, 2A8, 7A11, 7G3, 2E9, 4E3 and 4H7 were measured (FIG. 5 and FIG. 6).

Example 4: Measuring Cell Binding of Anti-Doppel Antibodies Using Flow Cytometry Human tumor endothelial cells, cancer cells and doppel knock-down cells were cultured in 6 well plates. Cells were trypsinized and prepared in single cell suspensions. Cells were than incubated with each anti-doppel antibody for 30 mins. After labeling antibodies with secondary fluorescent antibody, cell binding was measured using flow cytometry.

Figure 7A:
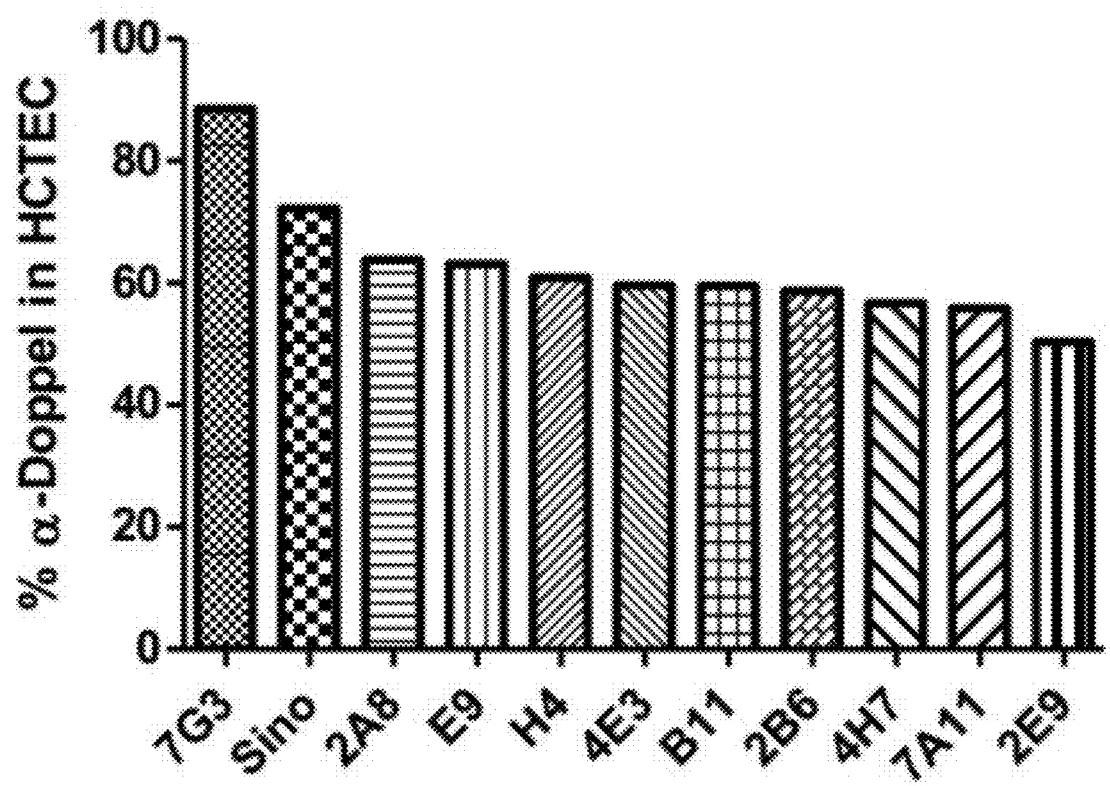
FIG. 7A-7C show cell binding of anti-doppel monoclonal antibodies using flow cytometry. Quantification of HTEC cell binding of 7G3, Sino (commercialized antibody), 2A8, E9, H4, 4E3, B11, 2B6, 4H7, 7A11 and 2E9 (FIG. 7A) and their histograms (FIG. 7B). Binding of A12, B2, 7G3, 2B6 and 2C10 on doppel-expressing and doppel knock down cells (FIG. 7C).
Figure 7B:
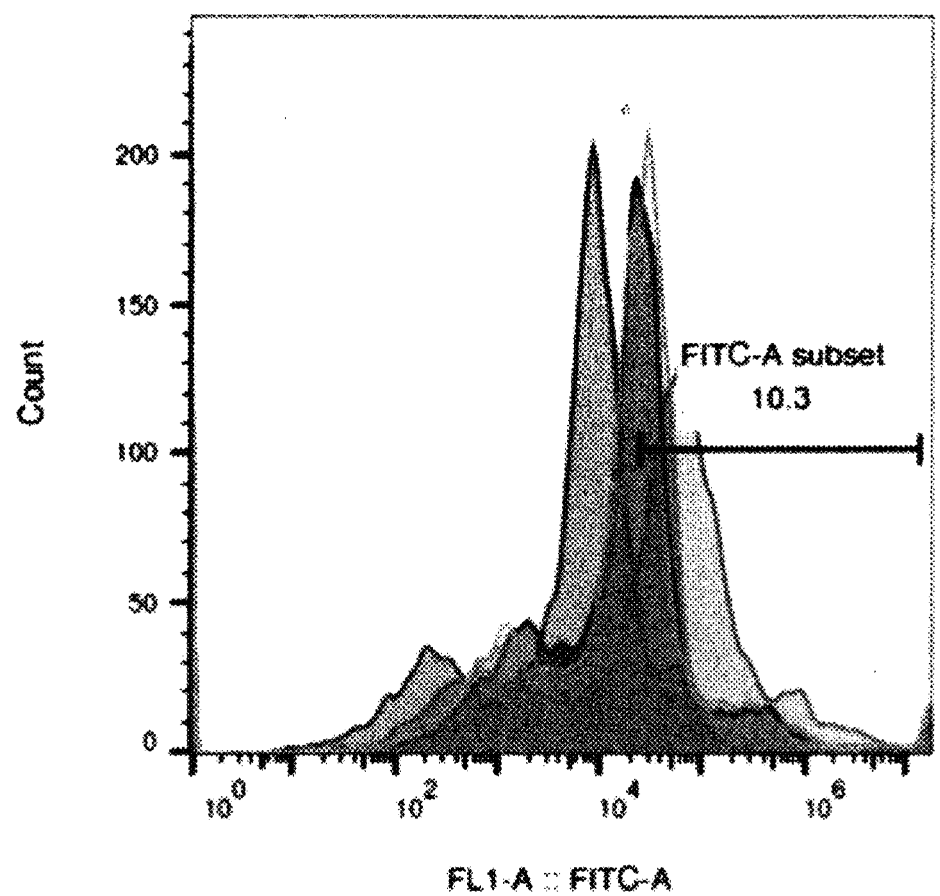
Figure 7C:
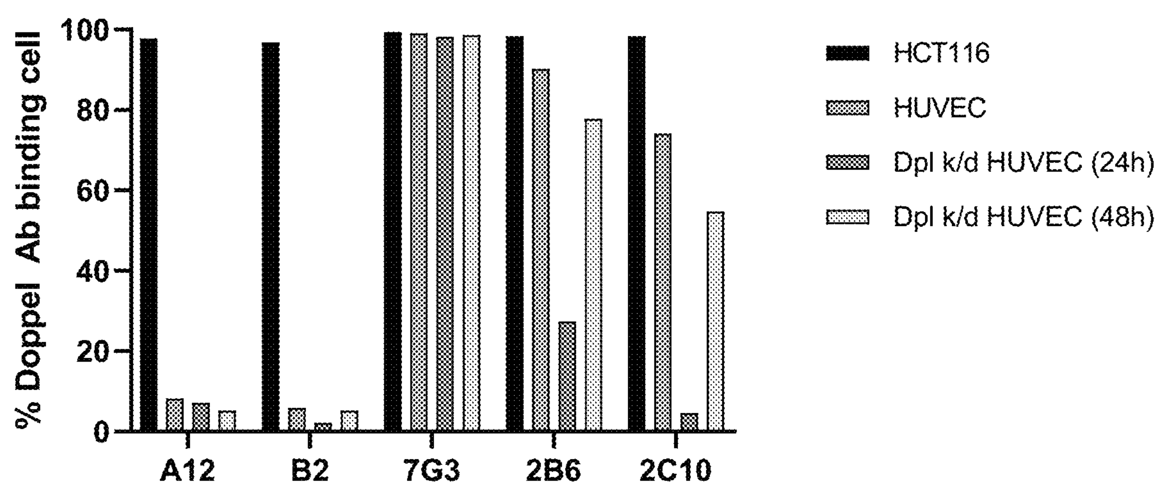
Figure 8:
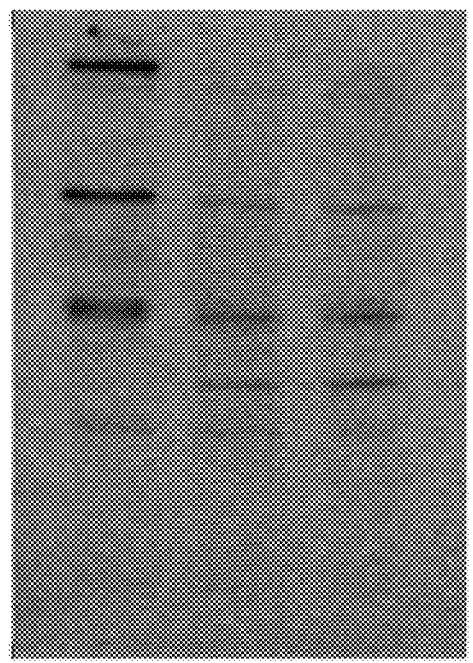
FIG. 8 shows doppel expression on HCTEC tumor endothelial cells compared with HUVEC and Hu.dpl cells.

The results showed that antibodies produced by clones 7G3, 2B6 and 2C10 and human monoclonal antibodies A12 and B2 exhibited higher binding affinity and human monoclonal antibodies A12 and B2 showed more specific binding to doppel molecules (FIG. 7).

Example 5: Generation of TEC Spheroid and Inhibiting Angiogenic Sprouting Using Antibodies The spheroid-based in vitro angiogenesis assay was performed using anti-doppel antibodies disclosed herein. 70-80% confluent of tumor endothelial cells were trypsinized and suspended in the mixture of endothelial cell growth media (ECGM) and methocel with 4:1 ratio. One spheroid was designed to be consisted of 1000 endothelial cells with 25 μL and cultured for 48 h with hanging drop method in 37° C., 5% $CO_2$ conditions. After that, spheroids were collected carefully and suspended in the mixture of iced collagen solution (rat tail type I in 0.1% acidic acid) and 10% MEM 199 media with VEGF (50 ng/mL). Spheroids were seeded on to 24-well plates at a density of 50-100 spheroids/well and incubated in 37° C., 5% $CO_2$ conditions for 30 mins followed by treatment with anti-doppel antibodies. After 24 hours, sprouting numbers in each group were quantified using optical microscope.

Figure 9A:
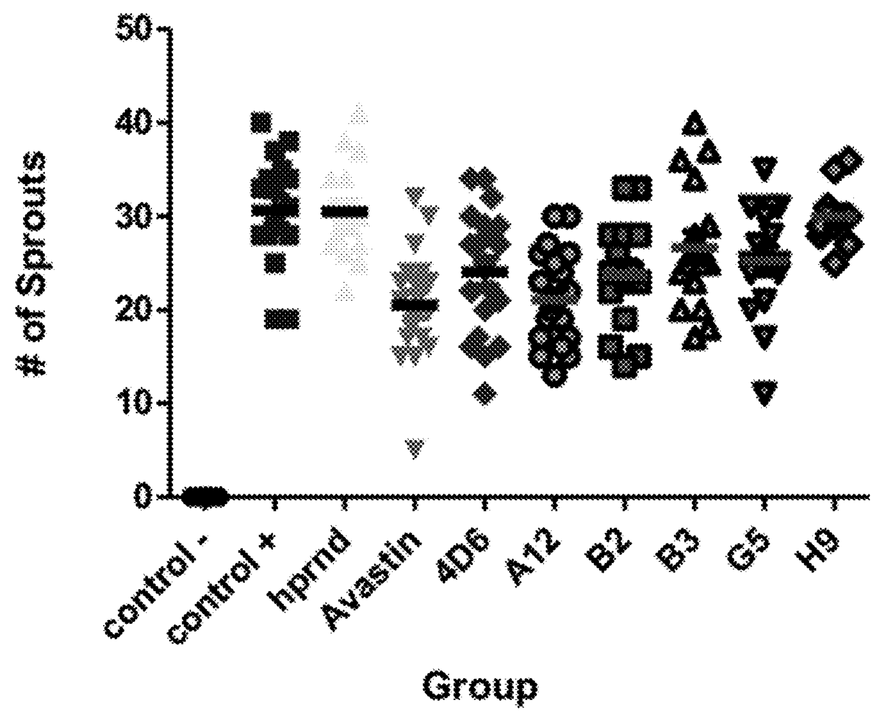
FIG. 9A-9C show an in vitro 3D spheroid assay for assessing anti-angiogenic efficacy of anti-doppel monoclonal antibodies disclosed herein. Quantification of angiogenic sprouting of cells treated with hPRND, Avastin, 4D6, A12, B2, B3, G5 and H9 is shown in FIG. 9A. Quantification of angiogenic sprouting of cells treated with Avastin, Sino (commercialized antibody), 2A8, 2B6, 2C10, 2C12, 7A11, 2E9, 4D5, 4H7, 5D3, 7D7 and 7G3 is shown in FIG. 9B. Representative optical images of spheroid sprouting are shown in FIG. 9C.
Figure 9B:
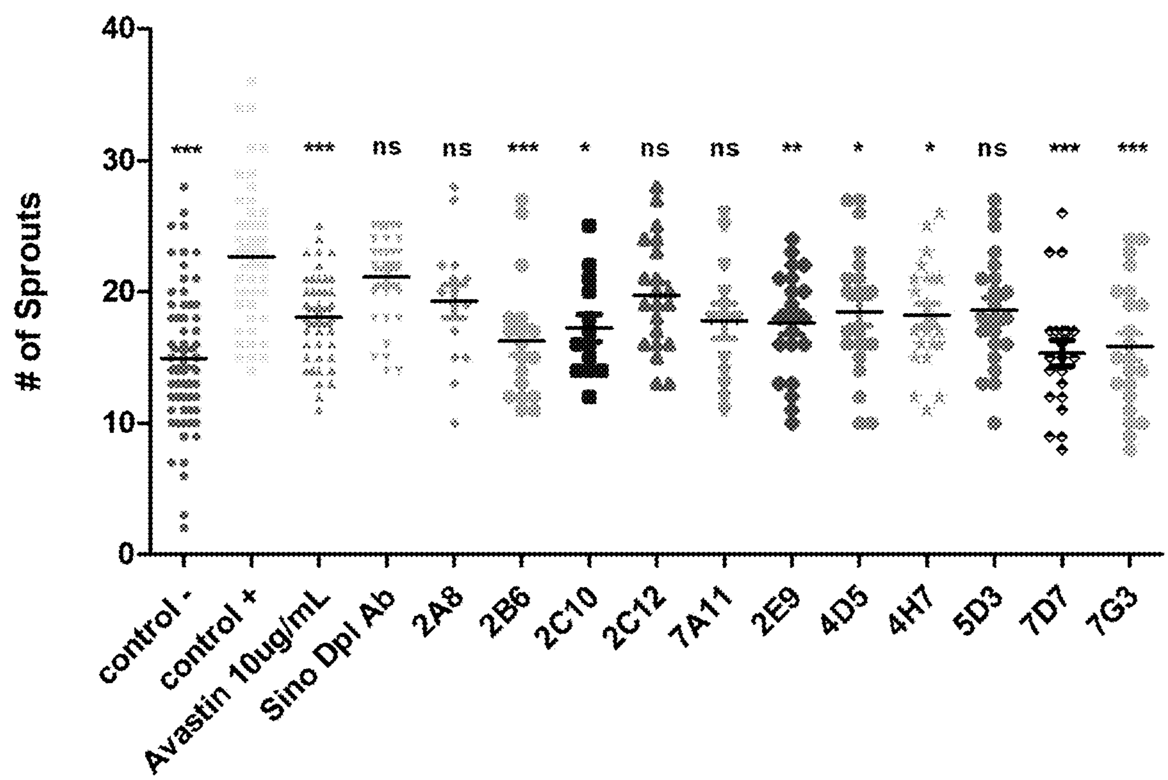
Figure 9C:
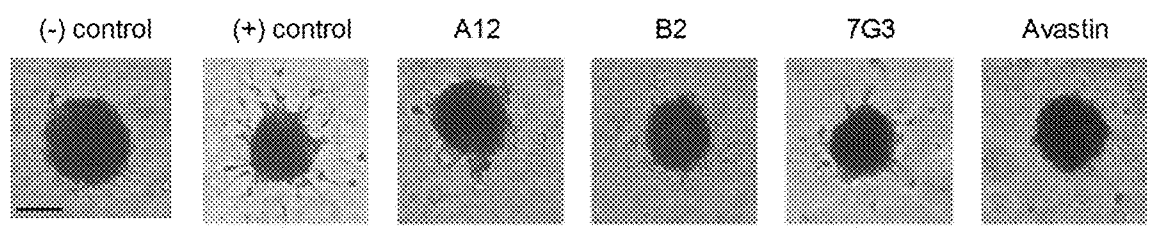

The results showed antibodies produced by clones 7G3 and 7D7 and human monoclonal antibodies B2 and A12 exhibited the best efficacy, similar to that of Avastin in inhibiting angiogenic sprouting (FIG. 9).

Example 6: Inhibiting Phosphorylation of VEGFR2, FGFR1 Using Anti-Doppel Antibodies The phosphorylation assay was done to evaluate whether anti-doppel antibodies can inhibit the phosphorylation of main angiogenic surface receptors such as VEGFR2 and FGFR1.

Human tumor endothelial cells were cultured on 6 well plates until confluent. Cells were washed with PBS 2 times and incubated in fasting media for 12 hours. Cells were than washed again with PBS 2 times and added with lysis buffer (LIPA buffer with protease and phosphatase inhibitors). Cell lysates were collected and centrifuged at 15,000 rpm for 15 mins and supernatant were taken for SDS-PAGE analysis.

Figure 10A:
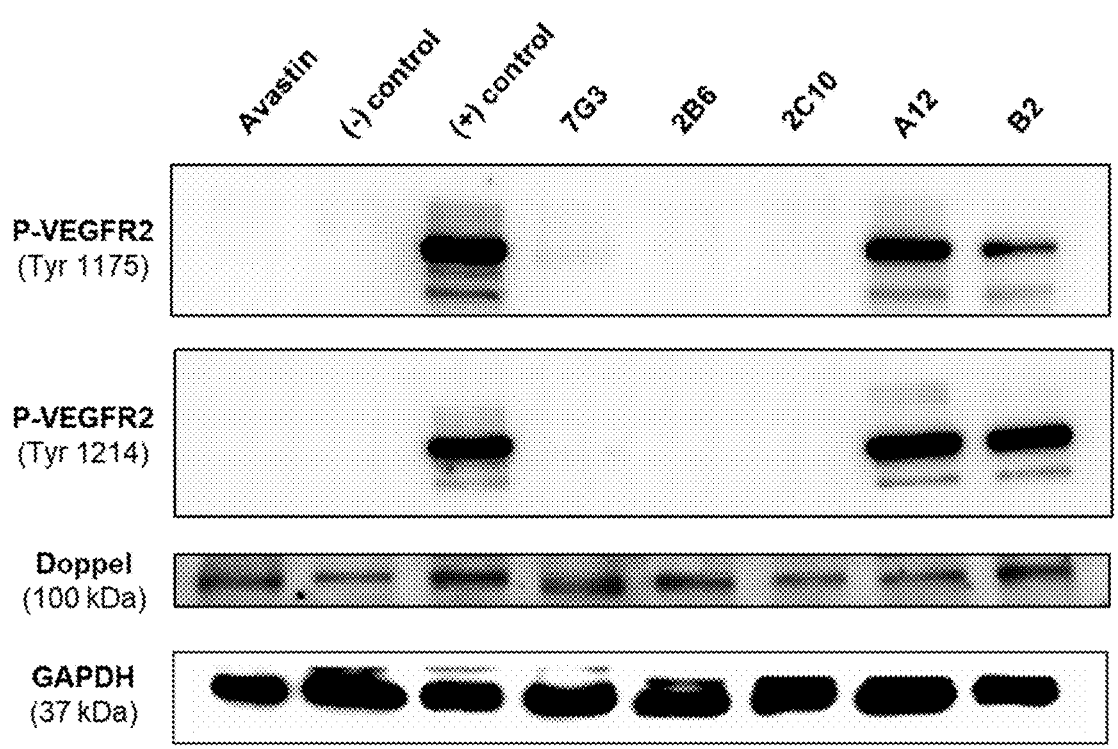
FIG. 10A-10C show in vitro phosphorylation assays of VEGFR2 and pFGFR1. Inhibition of phosphorylation of VEGFR2 using 7G3, 2B6, 2C10, A12 and B2 is shown in FIG. 10A. Inhibition of phosphorylation of pFGFR1 using 7G3, 2B6, A12, B2 and B2-19 is shown in FIG. 10B. Inhibition of phosphorylation of pVEGFR2 using 7G3, chimeric 7G3, humanized 7G3, 2B6, chimeric 2B6, humanized 2B6, 3D1, 3D5, 3H9, and 4D1 is shown in FIG. 10C.
Figure 10B:
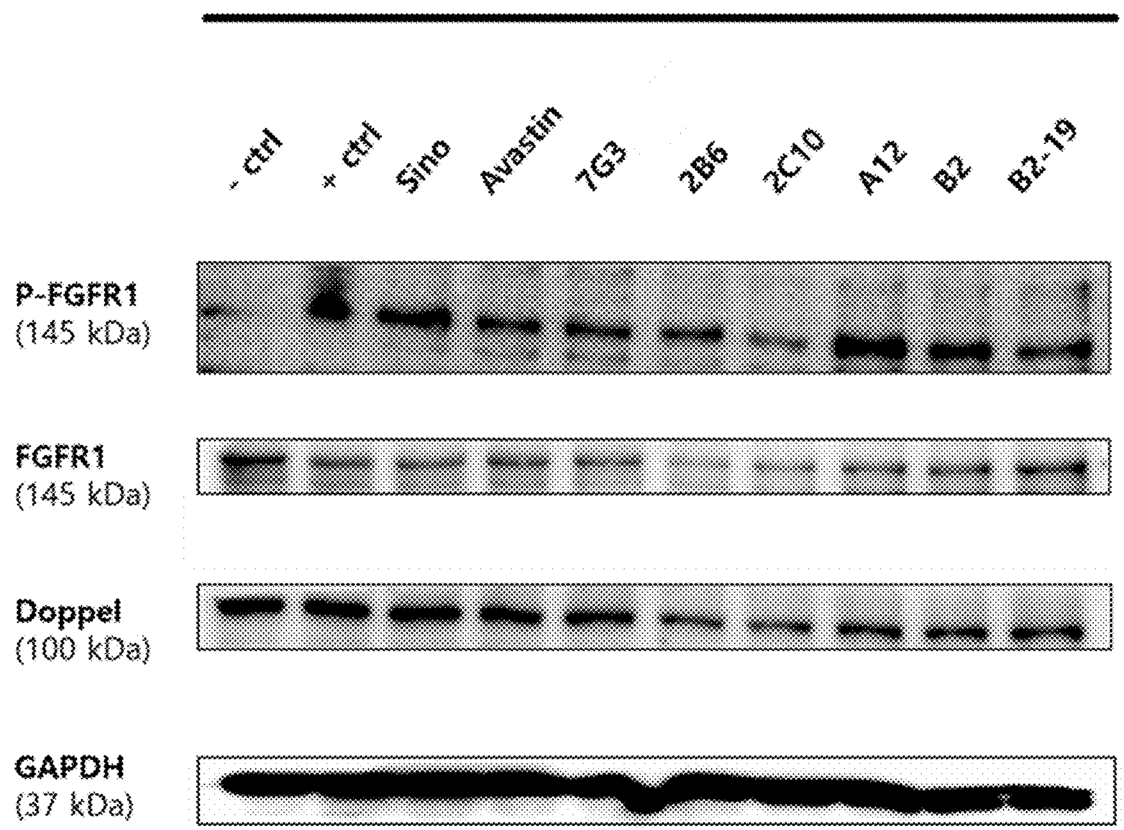
Figure 10C:
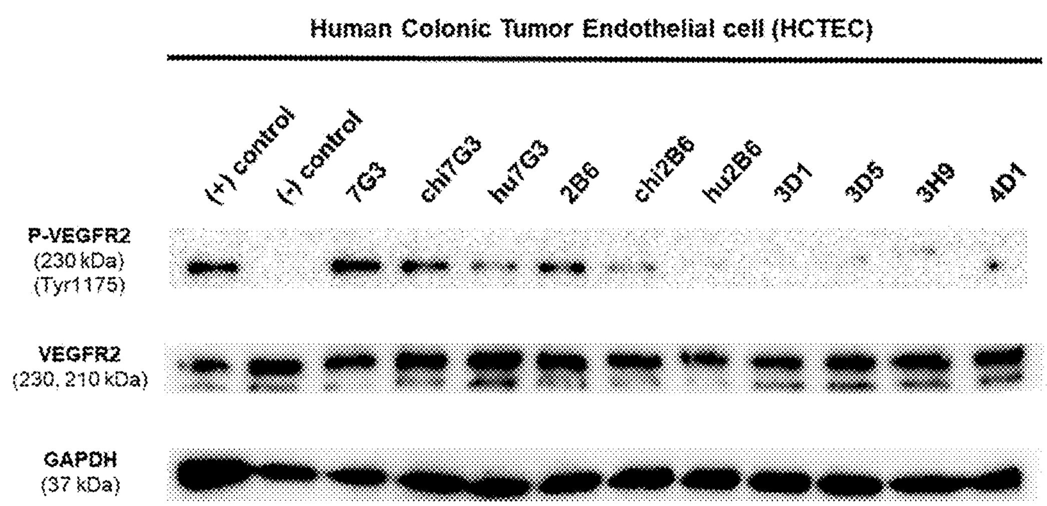

Results show that antibodies produced by clones 7G3, 2B6 and 2C10 could inhibit the phosphorylation of both VEGFR2 and FGFR1, while Avastin exerted inhibition effects only against pVEGFR2 (FIG. 10A-B). The VEGFR2 anti-phosphorylation effect is also exhibited by the 3D1, 3D5, 3H9, and 4D1 human monoclonal antibodies (FIG. 10C). This data may indicate that the doppel-targeting molecules described herein can inhibit the phosphorylation of receptors by preventing the interaction between doppel molecules and receptors on the surface of cells.

Figure 11:
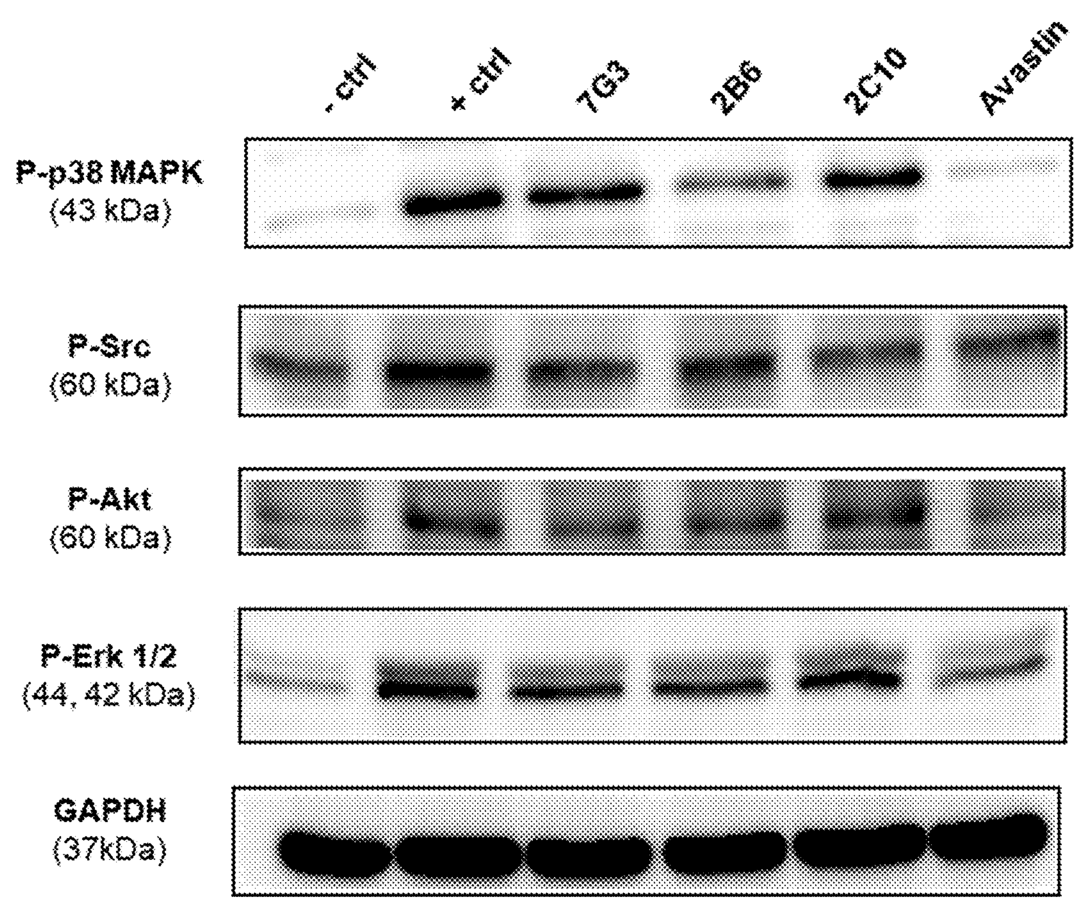
FIG. 11 shows evaluation of inhibition of down-stream angiogenic signaling after treatment with 7G3, 2B6, 2C10 and Avastin.
Figure 12A:
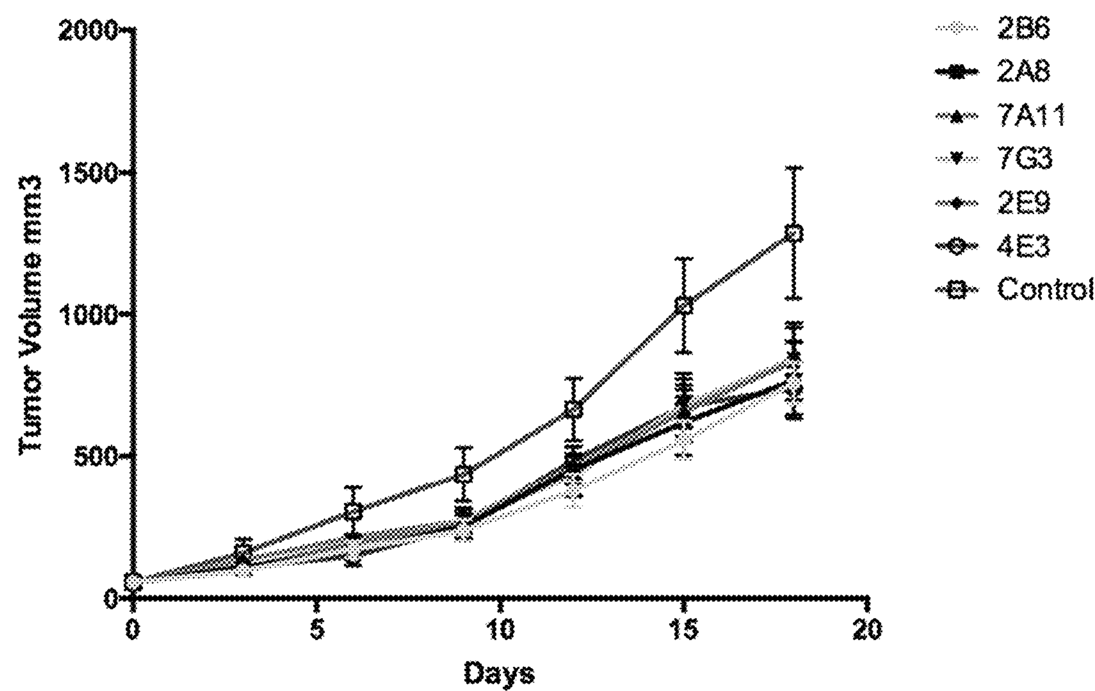
FIG. 12A-12D show in vivo anti-tumor efficacy of 7G3, 2B6, 2E9, 4E3, A12, B2, E9 and 4H7 using a wild type HCT116 xenograft tumor model. Anti-tumor efficacy of 2B6, 2A8, 7A11, 2E9 and 4E3 is shown in FIG. 12A. Anti-tumor efficacy of 4D6, Avastin, A12 and B2 is shown in FIG. 12B. Anti-tumor efficacy of 4H7, B2, B11, E9 and H4 is shown in FIG. 12C. Anti-tumor efficacy of Human IgG, Mouse IgG, Avastin, A12, B2, 7A11 and 4E3 is shown in FIG. 12D.
Figure 12B:
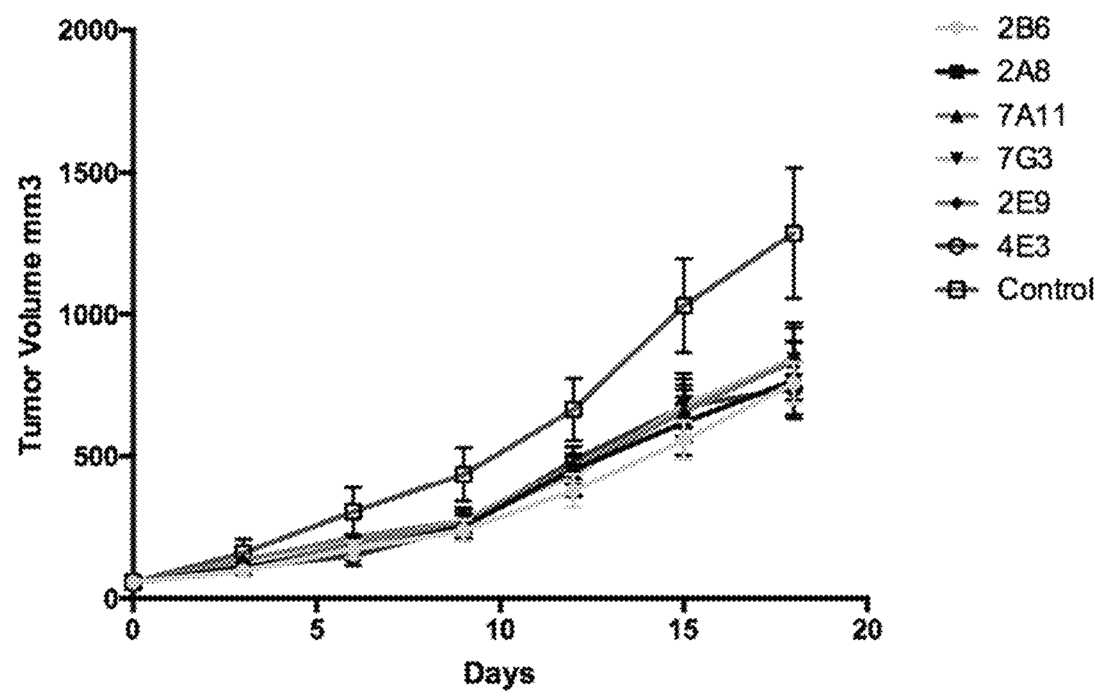
Figure 12C:
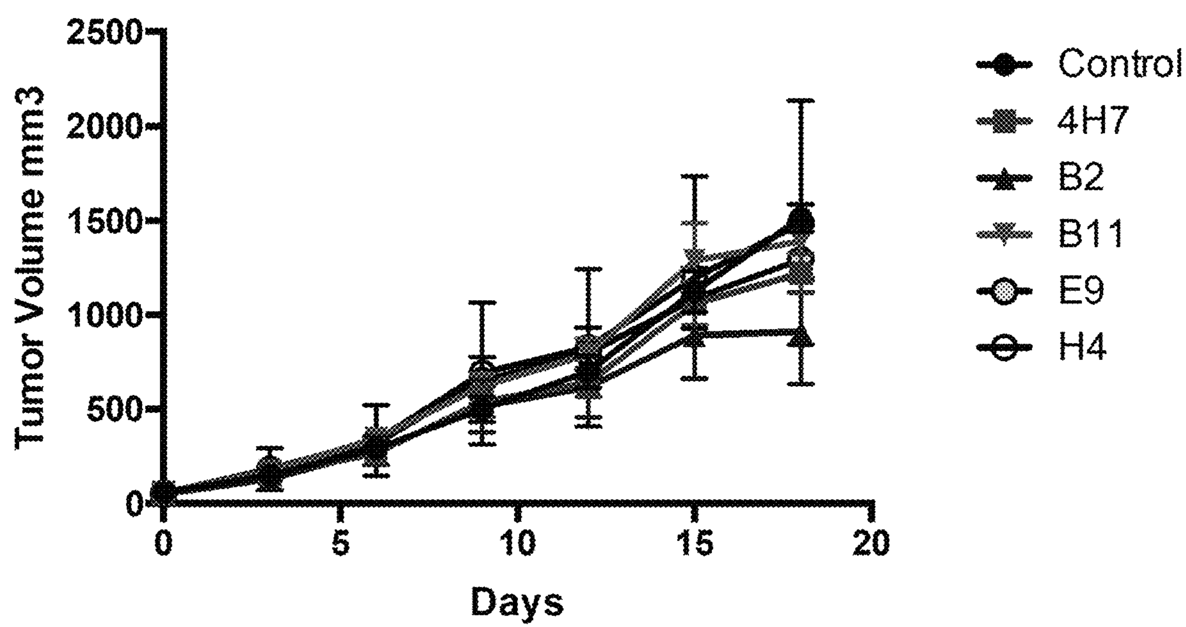
Figure 12D:
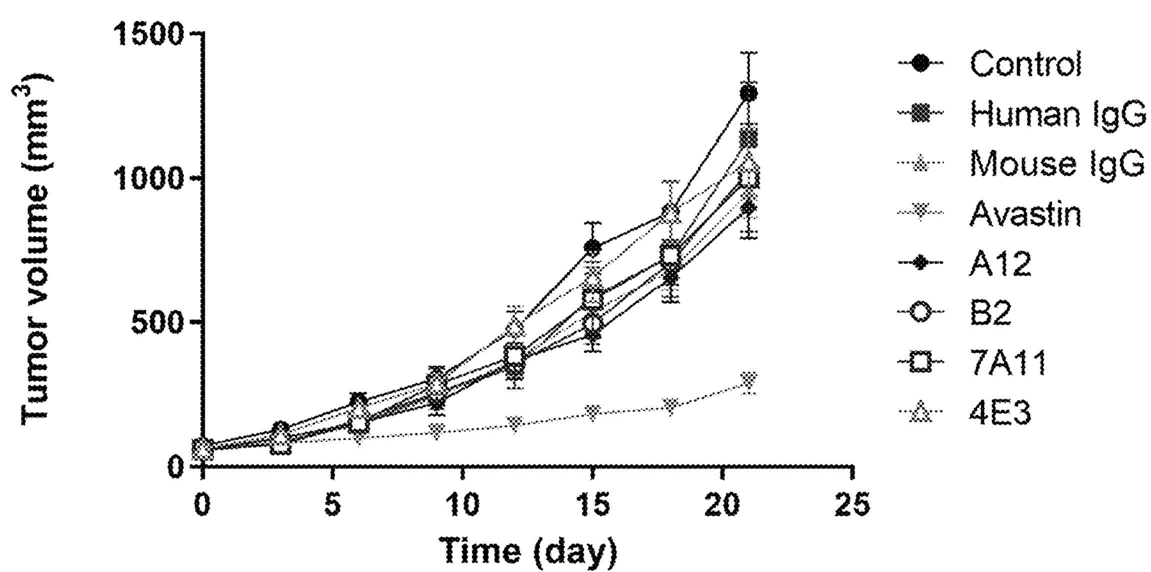
Figure 13A:
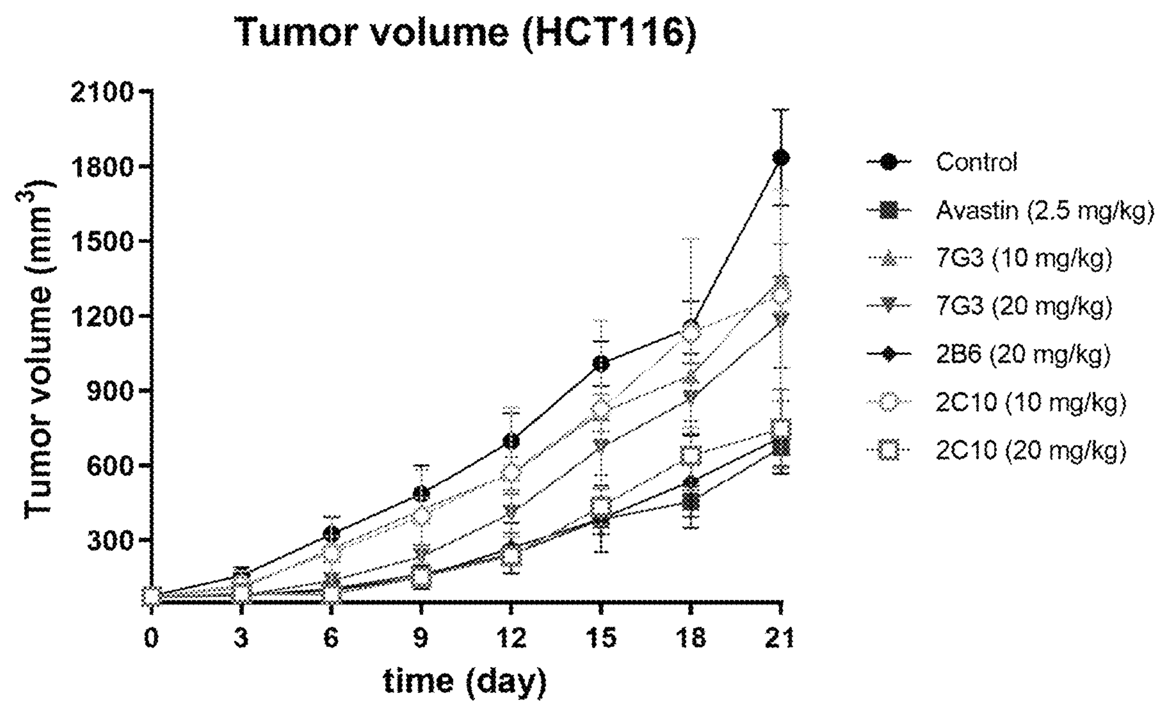
FIG. 13A-13D show in vivo anti-tumor efficacy of Avastin, 7G3 (10 and 20 mg/kg), 2B6 (20 mg/kg) and 2C10 (10 and 20 mg/kg) using an Avastin-resistant HCT116 xenograft tumor model. Anti-tumor efficacy of Avastin, 7G3, 2B6 and 2C10 is shown in FIG. 13A. Body weight change during treatment is shown in FIG. 13B. Tumor weight in each group after terminating the experiment is shown in FIG. 13C. Tumor images for each group is shown in FIG. 13D.
Figure 13B:
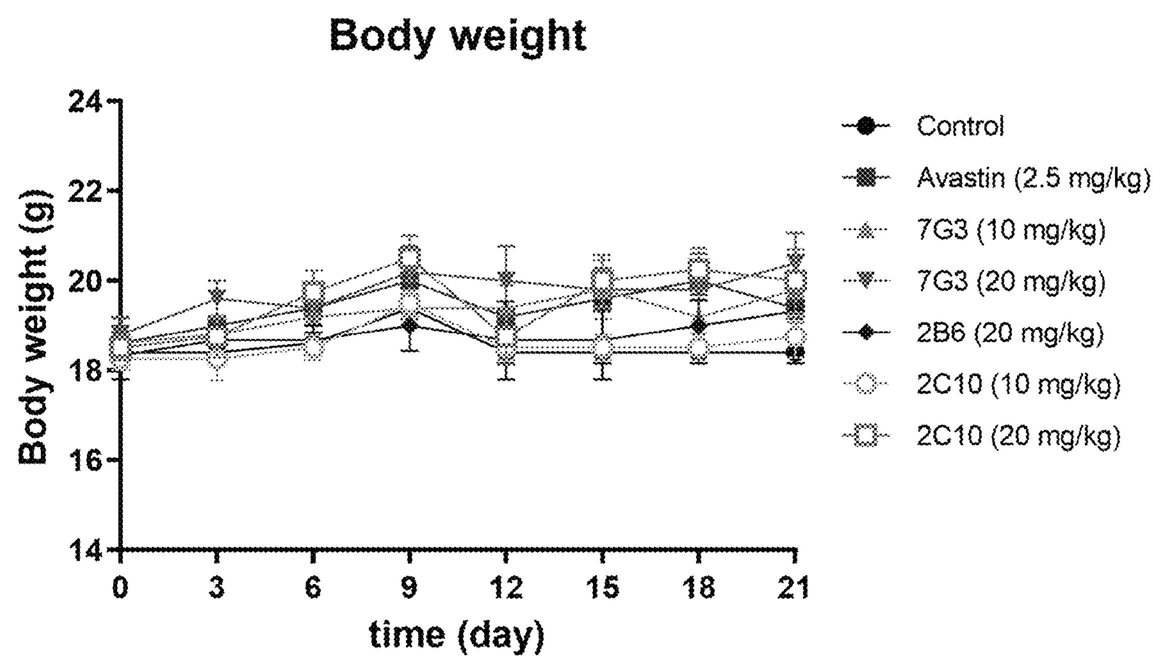
Figure 13C:
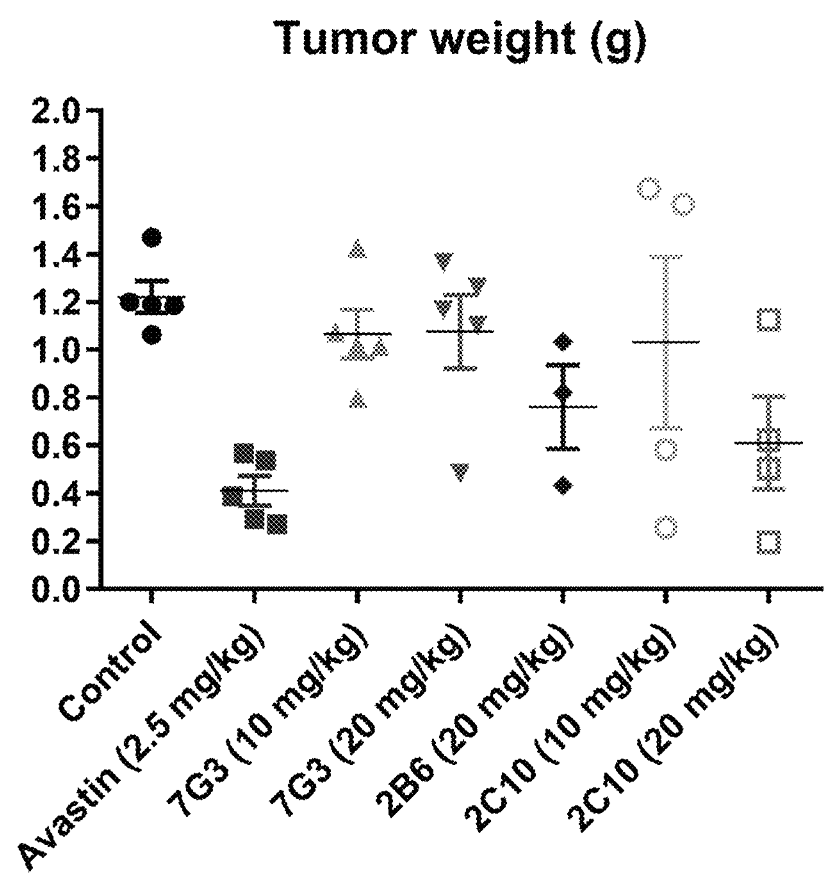
Figure 13D:
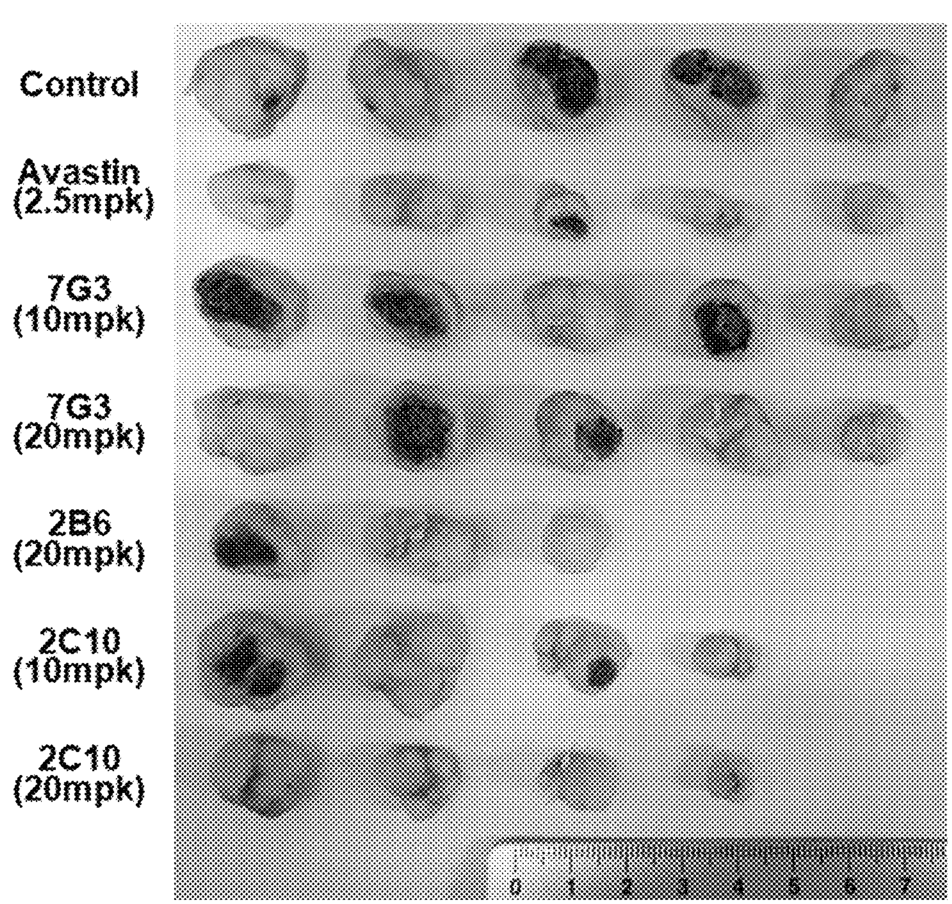

These effects were also shown by assessing down-signaling of angiogenic signals, which found that antibodies produced by clones 7G3, 2B6 and 2C10 can also prevent angiogenic signal transduction (FIG. 11).

Example 7: Anti-Doppel Antibodies Suppress Tumor Growth in Human Colon Cancer Models Custom made murine and human anti-doppel monoclonal antibodies were acquired and tested for recognition of mouse doppel present in host-derived blood vessels of tumors and ability to block doppel function to inhibit tumor growth.

For assessing anti-tumor efficacy of anti-doppel antibodies, an HCT116 xenograft tumor model was used. HCT116 cells ($1\times10^7$ cells/mouse) were inoculated to the left flank of the balb-c/nu mice. When the average tumor volume reached 70-100 $mm^3$, antibodies were treated every 3 days through intravenous for total 5 times. Tumor volume was measured every 3 days until the end of experiments.

Results showed that treatment with murine antibodies produced by clones 7G3, 2B6, 2E9, 4E3, or 4H7, or human monoclonal antibodies A12, B2, or E9 effectively suppressed the growth of tumor. However, the results were not as strong as observed with Avastin, possibly due to the dose not being high enough to elicit as strong an anti-tumor effects (FIG. 12).

A dose dependency test using the same tumor model and procedure was carried out. Results showed that 20 mg/kg of antibodies produced by clones 2B6 and 2C10 exhibited substantially enhanced anti-tumor efficacy and similar inhibiting effects as 2.5 mg/kg of Avastin. The different doses required to induce equivalent anti-tumor effects may be attributed to different mechanisms of action by the different antibodies (FIG. 13).

Figure 14A:
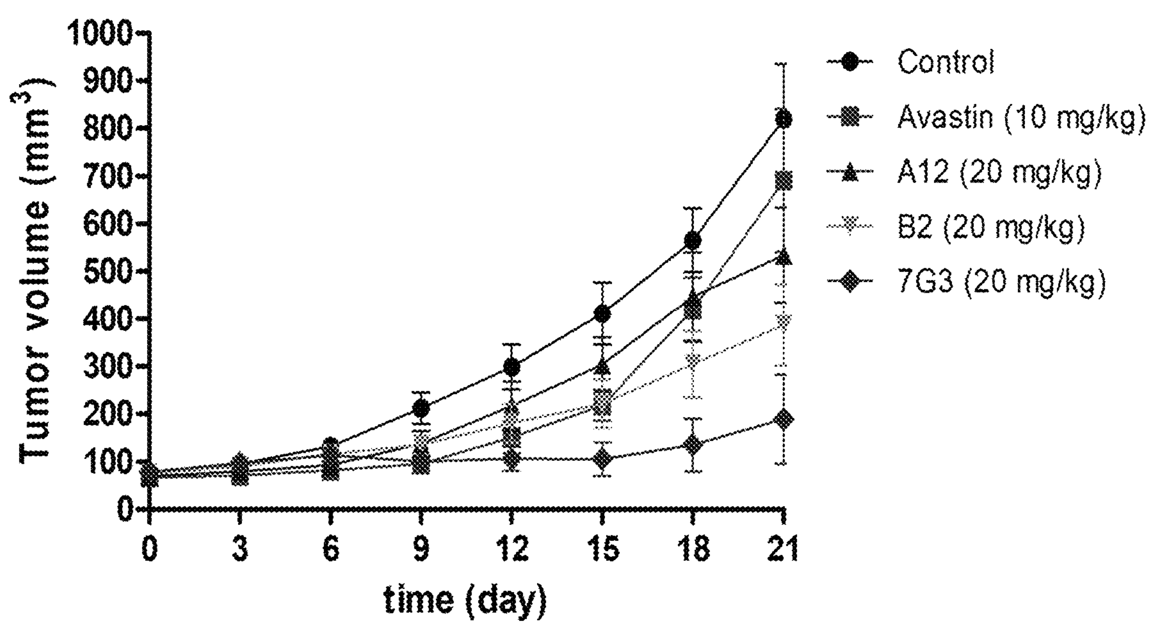
FIG. 14A-14B show in vivo anti-tumor efficacy of Avastin, A12 (20 mg/kg), B2 (20 mg/kg) and 7G3 (20 mg/kg) using a resistant type HCT116 xenograft tumor model (FIG. 14A). Individual tumor volume is shown in FIG. 14B.
Figure 14B:
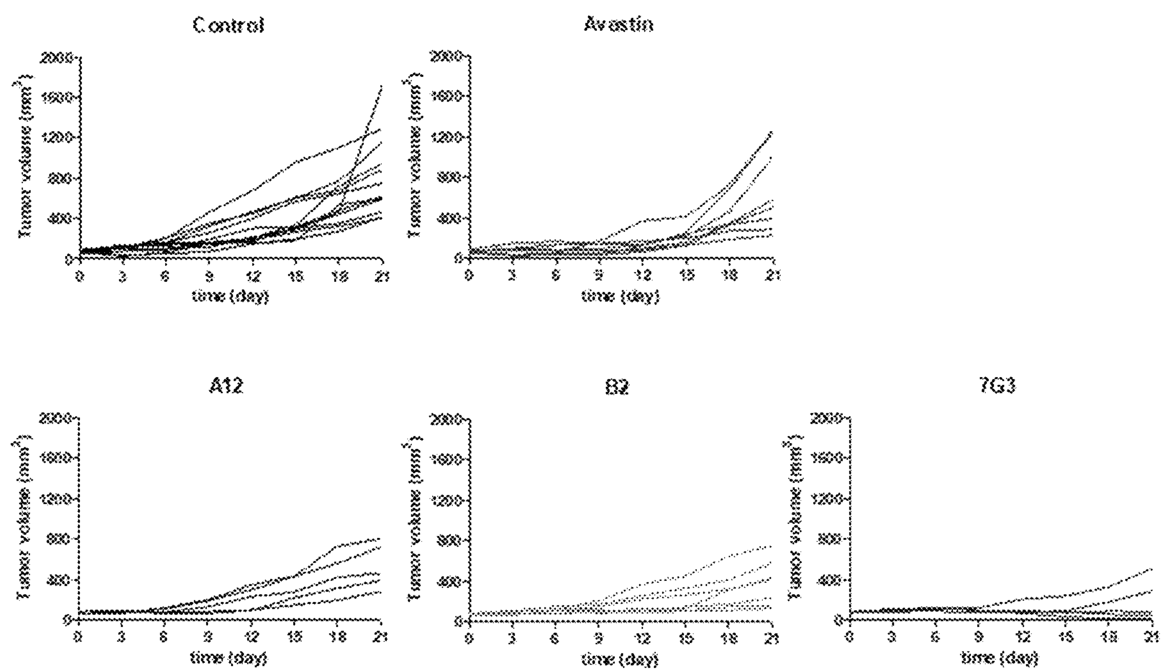

Efficacy was also tested using an Avastin-resistant HCT116 xenograft tumor model following the same procedure. In this case, results show that Avastin could not exert anti-tumor efficacy because of the resistant cell property, whereas Fab fragments A12 and B2, and the antibody produced by clone 7G3 showed substantially improved anti-tumor efficacy (FIG. 14). These data indicate that Avastin resistance can be overcome by using different anti-doppel antibodies that target a different anti-angiogenic mechanism.

Example 8: Pharmacokinetic Properties of Anti-Doppel Antibody

For pharmacokinetic analysis of an anti-doppel antibody as described herein (the antibody produced by clone 7G3), Sprague Dawley (SD) rats (male, 250 g) were used. After injecting FITC conjugated 7G3 antibody or Avastin, blood samples were extracted at 15 minutes, 30 minutes, 2 hours, 12 hours, 1 day, 2 days, 3 days, 4 days, 5 days, and 7 days. Plasma samples were collected by centrifuging blood samples at 4,000 g for 20 minutes. Antibody content in plasma was analyzed by quantifying fluorescent intensity.

Figure 15A:
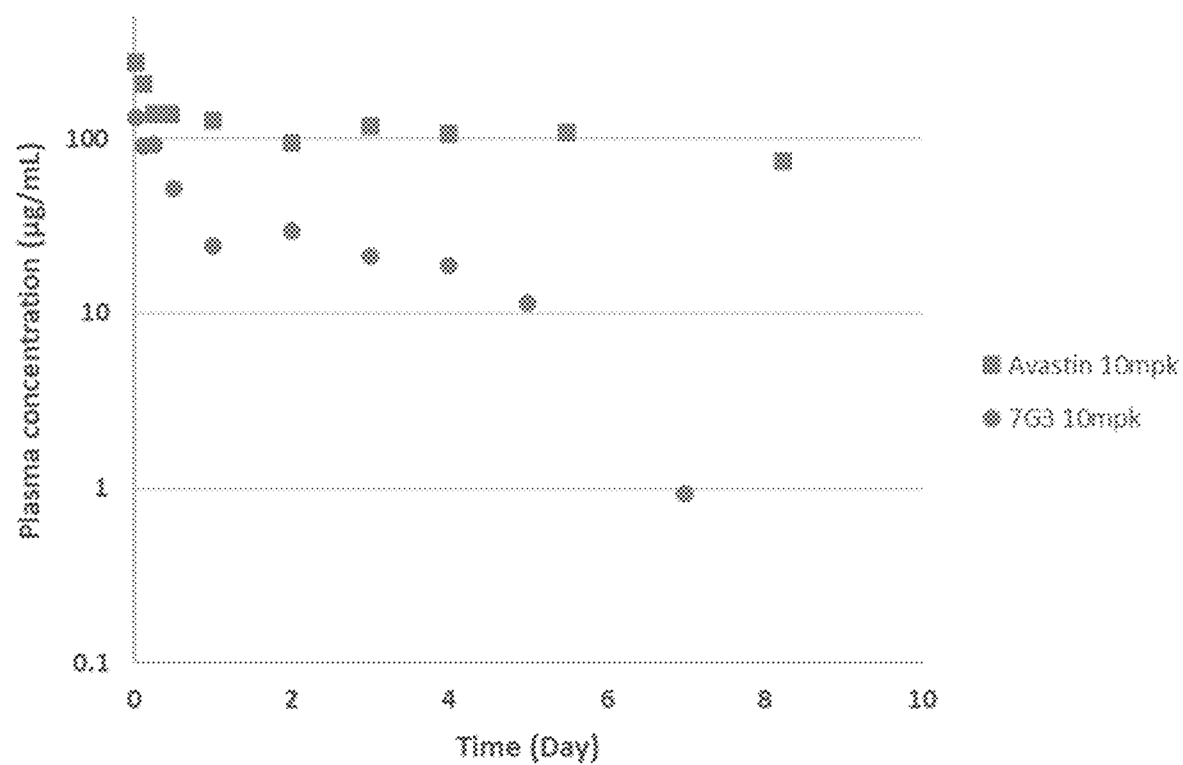

The results showed that alpha half-life of Avastin was more than 4-times longer than that of the antibody produced by clone 7G3 (FIG. 15). These results indicate that an anti-doppel molecule as disclosed herein may need more frequent dosing or higher dosing as compared to Avastin to maintain blood concentration.

Example 9: Production of Chimeric Antibodies and Humanized Antibodies

To produce chimeric antibodies, the VH and VL regions of mouse antibodies 7G3 and 2B6 were amplified in pcDNA3.4 (Invitrogen) vector by PCR, respectively. The animal cell expression vector was produced so that the constant region were from IgG1 (P01857_HUMAN-Immunoglobulin heavy constant gamma 1(IGHG1)) for the heavy chain and kappa (P01834_HUMAN-Immunoglobulin kappa constant (IGKC)) for the light chain.

The light chain of the chimeric 7G3 antibody designed as described above has an amino acid sequence of SEQ ID NO:

155. The heavy chain of the chimeric 7G3 antibody designed as described above has an amino acid sequence of SEQ ID NO: 157. The light chain of the chimeric 2B6 antibody designed as described above has an amino acid sequence of SEQ ID NO: 159. The heavy chain of the chimeric 2B6 antibody designed as described above has an amino acid sequence of SEQ ID NO: 161.

To produce humanized antibodies, the amino acid sequences of the heavy and light chain variable regions of mouse 7G3 antibody were compared with those of the human antibodies in the IMGT database, and the heavy chain genes IGHV1-46, IGHJ4, and the light chain gene IGKV3D-7 of the human antibody variable region with high similarity were selected. In order to humanize the mouse 7G3 antibody, the CDR of 7G3 antibody was grafted into a human antibody, and three amino acid residues of the humanized light chain FR (R71V, T73K, V78A) and one amino acid of the humanized heavy chain (L47W) were replaced with those of 7G3 antibody. In the same way, to humanize mouse 2B6 antibody, the CDR of 2B6 antibody was grafted into heavy chain genes VH3-66, IGHJ4, and light chain genes IGKV1-39 of the human antibody variable region, and three amino acid residues of the humanized heavy chain FR (E46A, R71V, N73K) and two amino acid residues of the humanized light chain (L46A, S60Y) were replaced with those of 2B6 antibody.

The light chain of the humanized 7G3 antibody designed as described above has an amino acid sequence of SEQ ID NO: 163. The heavy chain of humanized 7G3 antibody designed as described above has an amino acid sequence of SEQ ID NOs: 165. The light chain of the humanized 2B6 antibody designed as described above has an amino acid sequence of SEQ ID NO: 167. The heavy chain of humanized 2B6 antibody has an amino acid sequence of SEQ ID NOs: 169. The humanized antibody was genetically recombined with a humanized antibody to a variable region in an expression vector of a chimeric antibody.

For chimeric and humanized antibodies, polyethylenimine (PEI) was used in Freestylem 293-F cells (Invitrogen) to transfect plasmid DNA of heavy and light chain expression vectors at a ratio of 1:1. The transfected cells were cultured for 5 days at 37° C., 125 rpm, and 8% CO2 in a shaking CO2 incubator, and then the antibody was purified from the supernatant obtained by centrifugation using HiTrap MabSelect SuRe (Invitrogen).

TABLE 8

Antibody amino acid and nucleotide sequence

| | Ab | Sequence |
|---|---|---|
| Chimeric 7G3 | Light chain (Amino acid) | QIVLTQSPAIMSASLGERVTMTCTASSSVSSSYLHWYQQKPGSSPKL WIYSTSNLASGVPARFSGSGSGTSYSLTISSMEAEDTATYYCHQYHR SPLTFGAGTKLELKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC (SEQ ID NO: 155) |
| | Light chain (Nucleotide) | Caaattgttctcacccagtctccagcaatcatgtctgcatctctagg ggaacgggtcaccatgacctgcactgccagctcaagtgtaagttcca gttacttgcactggtaccagcagaagccaggatcctcccccaaactc tggatttatagcacatccaacctggcttctggagtcccagctcgctt cagtggcagtgggtctgggacctcttactctctcacaatcagcagca tggaggctgaagatactgccacttattactgccaccagtatcatcgt tccccactcacgttcggtgctgggaccaagctggagctgaaacgtac ggtggctgcaccatctgtcttcatcttcccgccatctgatgagcagt tgaaatctggaactgcctctgttgtgtgcctgctgaataacttctat cccagagaggccaaagtacagtggaaggtggataacgccctccaatc gggtaactcccaggagagtgtcacagagcaggacagcaaggacagca cctacagcctcagcagcaccctgacgctgagcaaagcagactacgag aaacacaaagtctacgcctgcgaagtcacccatcagggcctgagctc gcccgtcacaaagagcttcaacaggggagagtgttag (SEQ ID NO: 156) |
| | Heavy chain (Amino acid) | EIQLQQTGPELVKPGASVKISCKASGYSFTDYIMLWVKQSHGKSLEW IGNINPYYGSTSYNLKFKGKATLTVDKSSSTAYMQLNSLTSEDSAVY YCARRNYYGNYDAMDYWGQGTSVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSRDELTKNQVSLTCLVKGF YPSDIAVEWESNGQPENNYKTTPPVLDSDGSFFLYSKLTVDKSRWQQ GNVFSCSVMHEALHNHYTQKSLSLSPGK (SEQ ID NO: 157) |
| | Heavy chain (Nucleotide) | gagatccagctgcagcagactggacctgagctggtgaagcctggggc ttcagtgaagatatcctgcaaggcttctggttattcattcactgact acatcatgctctgggtgaagcagagccatggaaagagccttgagtgg attggaaatattaatccttactatggtagtactagctacaatctgaa gttcaagggcaaggccacattgactgtagacaaatcttccagcacag cctacatgcagctcaacagtctgacatctgaggactctgcagtctat tactgtgcaagaaggaactactatggtaactacgatgctatggacta ctggggtcaaggaacctcagtcaccgtctcctcagctagcaccaagg gcccatcggtcttccccctggcaccctcctccaagagcacctctggg ggcacagcggccctgggctgcctggtcaaggactacttccccgaacc ggtgacggtgtcgtggaactcaggcgccctgaccagcggcgtgcaca ccttcccggctgtcctacagtcctcaggactctactccctcagcagc |

TABLE 8-continued

Antibody amino acid and nucleotide sequence

| | Ab | Sequence |
|---|---|---|
| | | gtggtgaccgtgccctccagcagcctgggcacccagacctacatctg<br>caacgtgaatcacaagcccagcaacaccaaggtggacaagaaagttg<br>agcccaaatcttgtgacaaaactcacacatgcccaccgtgcccagca<br>cctgaactcctggggggaccgtcagtcttcctcttccccccaaaacc<br>caaggacaccctcatgatctcccggacccctgaggtcacatgcgtgg<br>tggtggacgtgagccacgaagaccctgaggtcaagttcaactggtac<br>gtggacggcgtggaggtgcataatgccaagacaaagccgcgggagga<br>gcagtacaacagcacgtaccgtgtggtcagcgtcctcaccgtcctgc<br>accaggactggctgaatggcaaggagtacaagtgcaaggtctccaac<br>aaagccctcccagcccccatcgagaaaaccatctccaaagccaaagg<br>gcagccccgagaaccacaggtgtacaccctgcccccatcccgggacg<br>agctgaccaagaaccaggtcagcctgacctgcctggtcaaaggcttc<br>tatcccagcgacatcgccgtggagtgggagagcaatgggcagccgga<br>gaacaactacaagaccacgcctcccgtgctggactccgacggctcct<br>tcttcctctacagcaagctcaccgtggacaagagcaggtggcagcag<br>gggaacgtcttctcatgctccgtgatgcatgaggctctgcacaacca<br>ctacacgcagaagagcctctccctgtctccgggtaaatga<br>(SEQ ID NO: 158) |
| Chimeric 2B6 | Light chain (Amino acid) | DIVMTQSQKFMSTSVGDRVSVTCKASQNVDANVAWYQQKPGQSPKAL<br>IYSASYRYSGVPYRFTGSGSGTDFTLTISNVQSADLAEYFCQQYNSY<br>PFTFGSGTKLEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC<br>(SEQ ID NO: 159) |
| | Light chain (Nucleotide) | Gacattgtgatgacccagtctcaaaaattcatgtccacatcagtagg<br>agacagggtcagcgtcacctgcaaggccagtcagaatgtggatgcta<br>atgtagcctggtatcaacagaaaccaggacaatctcctaaagcactg<br>atttactcggcatcctaccggtacagtggagtcccttatcgcttcac<br>aggcagtggatctgggacagatttcactctcaccatcagcaatgtgc<br>agtctgcagacttggcagagtatttctgtcagcaatataacagctat<br>ccattcacgttcggctcggggacaaagttggaaataaaacgtacggt<br>ggctgcaccatctgtcttcatcttcccgccatctgatgagcagttga<br>aatctggaactgcctctgttgtgtgcctgctgaataacttctatccc<br>agagaggccaaagtacagtggaaggtggataacgccctccaatcggg<br>taactcccaggagagtgtcacagagcaggacagcaaggacagcacct<br>acagcctcagcagcaccctgacgctgagcaaagcagactacgagaaa<br>cacaaagtctacgcctgcgaagtcacccatcagggcctgagctcgcc<br>cgtcacaaagagcttcaacaggggagagtgttag<br>(SEQ ID NO: 160) |
| | Heavy chain (Amino acid) | QVQLQQSGAELVRPGVSVKLSCKFSGFTFTDYAMHWVRQSHAKSLAW<br>IGVISSYYGDASYNQKFTGKATMTVDKSSSTAYMELARLTSEDSAIY<br>YCARRLRGAMDYWGQGTSVTVSSASTKGPSVFPLAPSSKSTSGGTAA<br>LGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSD<br>IAVEWESNGQPENNYKTTPPVLDSDGSFFLYSKLTVDKSRWQQGNVF<br>SCSVMHEALHNHYTQKSLSLSPGK<br>(SEQ ID NO: 161) |
| | Heavy chain (Nucleotide) | caggtccagctgcagcagtctggggctgagctggtgaggcctggggt<br>ctcagtgaaactttcctgcaagttttctggcttcacattcactgatt<br>atgctatgcactgggtgaggcagagtcatgcaaagagtctagcgtgg<br>attggagttattagttcttactatggtgatgctagctacaaccagaa<br>gttcacgggcaaggccacaatgactgtagataaatcctccagcacag<br>cctatatggaacttgccagactgacatctgaggattctgccatctat<br>tactgtgcaagacgattacgaggggctatggactactggggtcaagg<br>aacctcagtcaccgtctcctcagctagcaccaagggcccatcggtct<br>tccccctggcaccctcctccaagagcacctctgggggcacagcggcc<br>ctgggctgcctggtcaaggactacttccccgaaccggtgacggtgtc<br>gtggaactcaggcgccctgaccagcggcgtgcacaccttcccggctg<br>tcctacagtcctcaggactctactccctcagcagcgtggtgaccgtg<br>ccctccagcagcctgggcacccagacctacatctgcaacgtgaatca<br>caagcccagcaacaccaaggtggacaagaaagttgagcccaaatctt<br>gtgacaaaactcacacatgcccaccgtgcccagcacctgaactcctg<br>gggggaccgtcagtcttcctcttccccccaaaacccaaggacaccct<br>catgatctcccggacccctgaggtcacatgcgtggtggtggacgtga<br>gccacgaagaccctgaggtcaagttcaactggtacgtggacggcgtg<br>gaggtgcataatgccaagacaaagccgcgggaggagcagtacaacag<br>cacgtaccgtgtggtcagcgtcctcaccgtcctgcaccaggactggc<br>tgaatggcaaggagtacaagtgcaaggtctccaacaaagccctccca<br>gcccccatcgagaaaaccatctccaaagccaaagggcagccccgaga |

TABLE 8-continued

Antibody amino acid and nucleotide sequence

| | Ab | Sequence |
|---|---|---|
| | | accacaggtgtacaccctgcccccatcccgggacgagctgaccaaga accaggtcagcctgacctgcctggtcaaaggcttctatcccagcgac atcgccgtggagtgggagagcaatgggcagccggagaacaactacaa gaccacgcctcccgtgctggactccgacggctccttcttcctctaca gcaagctcaccgtggacaagagcaggtggcagcaggggaacgtcttc tcatgctccgtgatgcatgaggctctgcacaaccactacacgcagaa gagcctctccctgtctccgggtaaatga (SEQ ID NO: 162) |
| Humanized 7G3 | Light chain (Amino acid) | EIVMTQSPATLSLSPGERATLSCTASSSVSSSYLHWYQQKPGQAPRL WIYSTSNLASGIPARFSGSGSGTDFTLTISSLQPEDFAVYYCHQYHR SPLTFGQGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC (SEQ ID NO: 163) |
| | Light chain (Nucleotide) | Gagatcgtgatgacccagtccccagccacactgtctctgtccccagg agagagagccaccctgagctgcacagcctcctcctccgtgtcctcct cctacctgcactggtatcagcagaagcccggccaggctcctaggctg tggatctacagcacctctaacctggcctctggcatccccgctcggtt ctccggcagcggctctggcacagactttaccctgacaatctccagcc tgcagcctgaggatttcgccgtgtactattgtcaccagtatcatcgc tccccactgacctttggccagggcacaaaggtggagatcaagcgtac ggtggctgcaccatctgtcttcatcttcccgccatctgatgagcagt tgaaatctggaactgcctctgttgtgtgcctgctgaataacttctat cccagagaggccaaagtacagtggaaggtggataacgccctccaatc gggtaactcccaggagagtgtcacagagcaggacagcaaggacagca cctacagcctcagcagcaccctgacgctgagcaaagcagactacgag aaacacaaagtctacgcctgcgaagtcacccatcagggcctgagctc gcccgtcacaaagagcttcaacaggggagagtgttag (SEQ ID NO: 164) |
| | Heavy chain (Amino acid) | QVQLVQSGAEVKKPGASVKVSCKASGYSFTDYIMLWVRQAPGQGLEW MGNINPYYGSTSYNLKFKGRVTMTVDKSTSTAYMELSSLRSEDTAVY YCARRNYYGNYDAMDYWGQGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSRDELTKNQVSLTCLVKGF YPSDIAVEWESNGQPENNYKTTPPVLDSDGSFFLYSKLTVDKSRWQQ GNVFSCSVMHEALHNHYTQKSLSLSPGK (SEQ ID NO: 165) |
| | Heavy chain (Nucleotide) | caggtgcagctggtgcagtccggagctgaggtgaagaagccaggagc ctccgtgaaggtgtcttgcaaggcctctggctactccttcaccgact atatcatgctgtgggtgaggcaggctccaggacagggactggagtgg atgggaaacatcaatccttactatggcagcacatcttacaacctgaa gtttaagggcagagtgaccatgacagtggacaagtccaccagcacag cctatatggagctgtccagcctgcgcagcgaggataccgccgtgtac tattgtgctaggcggaactactatggcaattacgacgctatggatta ttggggccagggcaccctggtgacagtgtcttccgctagcaccaagg gcccatcggtcttcccctggcaccctcctccaagagcacctctggg ggcacagcggccctgggctgcctggtcaaggactacttccccgaacc ggtgacggtgtcgtggaactcaggcgccctgaccagcggcgtgcaca ccttcccggctgtcctacagtcctcaggactctactccctcagcagc gtggtgaccgtgccctccagcagcctgggcacccagacctacatctg caacgtgaatcacaagcccagcaacaccaaggtggacaagaaagttg agcccaaatcttgtgacaaaactcacacatgcccaccgtgcccagca cctgaactcctggggggaccgtcagtcttcctcttccccccaaaacc caaggacaccctcatgatctcccggacccctgaggtcacatgcgtgg tggtggacgtgagccacgaagaccctgaggtcaagttcaactggtac gtggacggcgtggaggtgcataatgccaagacaaagccgcgggagga gcagtacaacagcacgtaccgtgtggtcagcgtcctcaccgtcctgc accaggactggctgaatggcaaggagtacaagtgcaaggtctccaac aaagccctcccagcccccatcgagaaaaccatctccaaagccaaagg gcagccccgagaaccacaggtgtacaccctgcccccatcccgggacg agctgaccaagaaccaggtcagcctgacctgcctggtcaaaggcttc tatcccagcgacatcgccgtggagtgggagagcaatgggcagccgga gaacaactacaagaccacgcctcccgtgctggactccgacggctcct tcttcctctacagcaagctcaccgtggacaagagcaggtggcagcag gggaacgtcttctcatgctccgtgatgcatgaggctctgcacaacca ctacacgcagaagagcctctccctgtctccgggtaaatga (SEQ ID NO: 166) |

TABLE 8-continued

| Antibody amino acid and nucleotide sequence | | |
|---|---|---|
| | Ab | Sequence |
| Humanized 2B6 | Light chain (Amino acid) | DIQMTQSPSSLSASVGDRVTITCKASQNVDANVAWYQQKPGKAPKAL<br>IYSASYRYSGVPYRFSGSGSGTDFTLTISSLQPEDFATYYCQQYNSY<br>PFTFGQGTKVEIKRTVAAPSVFIFPPSDEQLKSGTASVVCLLNNFYP<br>REAKVQWKVDNALQSGNSQESVTEQDSKDSTYSLSSTLTLSKADYEK<br>HKVYACEVTHQGLSSPVTKSFNRGEC.<br>(SEQ ID NO: 167) |
| | Light chain (Nucleotide) | Gacatccagatgacccagagcccttccagcctgagcgcctctgtggg<br>cgacagggtgaccatcacatgcaaggcttctcagaacgtggatgcca<br>atgtggcttggtaccagcagaagcccggcaaggcccctaaggcgctg<br>atctattccgcctcctacaggtattctggagtgccataccggttctc<br>tggctccggcagcggaaccgactttaccctgacaatctcttccctgc<br>agccagaggatttcgccacatactattgtcagcagtacaactcctat<br>cccttcacctttggccagggcacaaaggtggagatcaagcgtacggt<br>ggctgcaccatctgtcttcatcttcccgccatctgatgagcagttga<br>aatctggaactgcctctgttgtgtgcctgctgaataacttctatccc<br>agagaggccaaagtacagtggaaggtggataacgccctccaatcggg<br>taactcccaggagagtgtcacagagcaggacagcaaggacagcacct<br>acagcctcagcagcaccctgacgctgagcaaagcagactacgagaaa<br>cacaaagtctacgcctgcgaagtcacccatcagggcctgagctcgcc<br>cgtcacaaagagcttcaacaggggagagtgttag<br>(SEQ ID NO: 168) |
| | Heavy chain (Amino acid) | EVQLVESGGGLVQPGGSLRLSCAASGFTFTDYAMHWVRQAPGKGLAW<br>VAVISSYYGDASYNQKFTGRFTISVDKSKNTLYLQMNSLRAEDTAVY<br>YCARRLRGAMDYWGQGTLVTVSSASTKGPSVFPLAPSSKSTSGGTAA<br>LGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSD<br>IAVEWESNGQPENNYKTTPPVLDSDGSFFLYSKLTVDKSRWQQGNVF<br>SCSVMHEALHNHYTQKSLSLSPGK<br>(SEQ ID NO: 169) |
| | Heavy chain (Nucleotide) | gaggtgcagctggtggagtctggaggaggactggtgcagccaggagg<br>cagcctgaggctgtcttgcgccgcttccggcttcacctttacagact<br>acgccatgcactgggtgagacaggctcctggcaagggactggcgtgg<br>gtggccgtgatctccagctactatggcgacgcttcctacaaccagaa<br>gttcaccggcaggtttacaatcagcgtggataagtctaagaacaccc<br>tgtatctgcagatgaatagcctgagagccgaggacacagccgtgtac<br>tattgtgccaggcggctgcgcggcgctatggattattggggccaggg<br>caccctggtgacagtgtcttccgctagcaccaagggcccatcggtct<br>tccccctggcaccctcctccaagagcacctctgggggcacagcggcc<br>ctgggctgcctggtcaaggactacttccccgaaccggtgacggtgtc<br>gtggaactcaggcgccctgaccagcggcgtgcacaccttcccggctg<br>tcctacagtcctcaggactctactccctcagcagcgtggtgaccgtg<br>ccctccagcagcctgggcacccagacctacatctgcaacgtgaatca<br>caagcccagcaacaccaaggtggacaagaaagttgagcccaaatctt<br>gtgacaaaactcacacatgcccaccgtgcccagcacctgaactcctg<br>gggggaccgtcagtcttcctcttccccccaaaacccaaggacaccct<br>catgatctcccggacccctgaggtcacatgcgtggtggtggacgtga<br>gccacgaagaccctgaggtcaagttcaactggtacgtggacggcgtg<br>gaggtgcataatgccaagacaaagccgcgggaggagcagtacaacag<br>cacgtaccgtgtggtcagcgtcctcaccgtcctgcaccaggactggc<br>tgaatggcaaggagtacaagtgcaaggtctccaacaaagccctccca<br>gcccccatcgagaaaaccatctccaaagccaaagggcagccccgaga<br>accacaggtgtacaccctgcccccatcccgggacgagctgaccaaga<br>accaggtcagcctgacctgcctggtcaaaggcttctatcccagcgac<br>atcgccgtggagtgggagagcaatgggcagccggagaacaactacaa<br>gaccacgcctcccgtgctggactccgacggctccttcttcctctaca<br>gcaagctcaccgtggacaagagcaggtggcagcaggggaacgtcttc<br>tcatgctccgtgatgcatgaggctctgcacaaccactacacgcagaa<br>gagcctctccctgtctccgggtaaatga<br>(SEQ ID NO: 170) |

Deposit Information

International Depositary Authority: Korean Cell Line Research Foundation

Accession Number: KCLRFBP00489; Date: 20200929
Accession Number: KCLRFBP00490; Date: 20200929
Accession Number: KCLRFBP00491; Date: 20200929
Accession Number: KCLRFBP00492; Date: 20200929
Accession Number: KCLRFBP00493; Date: 20200929
Accession Number: KCLRFBP00494; Date: 20201019
Accession Number: KCLRFBP00495; Date: 20201019
Accession Number: KCLRFBP00496; Date: 20201019
Accession Number: KCLRFBP00497; Date: 20201019
Accession Number: KCLRFBP00498; Date: 20201019
Accession Number: KCLRFBP00499; Date: 20201019
Accession Number: KCLRFBP00500; Date: 20201019

The invention claimed is:

1. A doppel-targeting molecule that binds to doppel, wherein the doppel targeting molecule comprises a heavy chain variable region and a light chain variable region, wherein:

(a) the heavy chain variable region comprises a CDRH1 comprising the amino acid sequence of SEQ ID NO: 58; a CDRH2 comprising the amino acid sequence of SEQ ID NO: 59; and a CDRH3 comprising the amino acid sequence of SEQ ID NO: 60; and the light chain variable region comprises a CDRL1 comprising the amino acid sequence of SEQ ID NO: 1; a CDRL2 comprising the amino acid sequence of SEQ ID NO: 2; and a CDRL3 comprising the amino acid sequence of SEQ ID NO: 3;

(b) the heavy chain variable region comprises a CDRH1 comprising the amino acid sequence of SEQ ID NO: 61; a CDRH2 comprising the amino acid sequence of SEQ ID NO: 62; and a CDRH3 comprising the amino acid sequence of SEQ ID NO: 63; and the light chain variable region comprises a CDRL1 comprising the amino acid sequence of SEQ ID NO: 4; a CDRL2 comprising the amino acid sequence of SEQ ID NO: 5; and a CDRL3 comprising the amino acid sequence of SEQ ID NO: 6;

(c) the heavy chain variable region comprises a CDRH1 comprising the amino acid sequence of SEQ ID NO: 64; a CDRH2 comprising the amino acid sequence of SEQ ID NO: 65; and a CDRH3 comprising the amino acid sequence of SEQ ID NO: 66; and the light chain variable region comprises a CDRL1 comprising the amino acid sequence of SEQ ID NO: 7; a CDRL2 comprising the amino acid sequence of SEQ ID NO: 8; and a CDRL3 comprising the amino acid sequence of SEQ ID NO: 9;

(d) the heavy chain variable region comprises a CDRH1 comprising the amino acid sequence of SEQ ID NO: 67; a CDRH2 comprising the amino acid sequence of SEQ ID NO: 68; and a CDRH3 comprising the amino acid sequence of SEQ ID NO: 69; and the light chain variable region comprises a CDRL1 comprising the amino acid sequence of SEQ ID NO: 10; a CDRL2 comprising the amino acid sequence of SEQ ID NO: 11; and a CDRL3 comprising the amino acid sequence of SEQ ID NO: 12;

(e) the heavy chain variable region comprises a CDRH1 comprising the amino acid sequence of SEQ ID NO: 70; a CDRH2 comprising the amino acid sequence of SEQ ID NO: 71; and a CDRH3 comprising the amino acid sequence of SEQ ID NO: 72; and the light chain variable region comprising a CDRL1 comprising the amino acid sequence of SEQ ID NO: 13; a CDRL2 comprising the amino acid sequence of SEQ ID NO: 14; and a CDRL3 comprising the amino acid sequence of SEQ ID NO: 15;

(f) the heavy chain variable region comprises a CDRH1 comprising the amino acid sequence of SEQ ID NO: 73; a CDRH2 comprising the amino acid sequence of SEQ ID NO: 74; and a CDRH3 comprising the amino acid sequence of SEQ ID NO: 75; and the light chain variable region comprises a CDRL1 comprising the amino acid sequence of SEQ ID NO: 16; a CDRL2 comprising the amino acid sequence of SEQ ID NO: 17; and a CDRL3 comprising the amino acid sequence of SEQ ID NO: 18;

(g) the heavy chain variable region comprises a CDRH1 comprising the amino acid sequence of SEQ ID NO: 76; a CDRH2 comprising the amino acid sequence of SEQ ID NO: 77; and a CDRH3 comprising the amino acid sequence of SEQ ID NO: 78; and the light chain variable region comprises a CDRL1 comprising the amino acid sequence of SEQ ID NO: 19; a CDRL2 comprising the amino acid sequence of SEQ ID NO: 20; and a CDRL3 comprising the amino acid sequence of SEQ ID NO: 21;

(h) the heavy chain variable region comprises a CDRH1 comprising the amino acid sequence of SEQ ID NO: 79; a CDRH2 comprising the amino acid sequence of SEQ ID NO: 80; and a CDRH3 comprising the amino acid sequence of SEQ ID NO: 81; and the light chain variable region comprises a CDRL1 comprising the amino acid sequence of SEQ ID NO: 22; a CDRL2 comprising the amino acid sequence of SEQ ID NO: 23; and a CDRL3 comprising the amino acid sequence of SEQ ID NO: 24;

(i) the heavy chain variable region comprises a CDRH1 comprising the amino acid sequence of SEQ ID NO: 82; a CDRH2 comprising the amino acid sequence of SEQ ID NO: 83; and a CDRH3 comprising the amino acid sequence of SEQ ID NO: 84; and the light chain variable region comprises a CDRL1 comprising the amino acid sequence of SEQ ID NO: 25; a CDRL2 comprising the amino acid sequence of SEQ ID NO: 26; and a CDRL3 comprising the amino acid sequence of SEQ ID NO: 27;

(j) the heavy chain variable region comprises a CDRH1 comprising the amino acid sequence of SEQ ID NO: 85; a CDRH2 comprising the amino acid sequence of SEQ ID NO: 86; and a CDRH3 comprising the amino acid sequence of SEQ ID NO: 87; and the light chain variable region comprises a CDRL1 comprising the amino acid sequence of SEQ ID NO: 28; a CDRL2 comprising the amino acid sequence of SEQ ID NO: 29; and a CDRL3 comprising the amino acid sequence of SEQ ID NO: 30;

(k) the heavy chain variable region comprises a CDRH1 comprising the amino acid sequence of SEQ ID NO: 88; a CDRH2 comprising the amino acid sequence of SEQ ID NO: 89; and a CDRH3 comprising the amino acid sequence of SEQ ID NO: 90; and the light chain variable region comprises a CDRL1 comprising the amino acid sequence of SEQ ID NO: 31; a CDRL2 comprising the amino acid sequence of SEQ ID NO: 32; and a CDRL3 comprising the amino acid sequence of SEQ ID NO: 33;

(l) the heavy chain variable region comprises a CDRH1 comprising the amino acid sequence of SEQ ID NO: 91; a CDRH2 comprising the amino acid sequence of SEQ ID NO: 92; and a CDRH3 comprising the amino acid sequence of SEQ ID NO: 93; and the light chain variable region comprises a CDRL1 comprising the amino acid sequence of SEQ ID NO: 34; a CDRL2 comprising the amino acid sequence of SEQ ID NO: 35; and a CDRL3 comprising the amino acid sequence of SEQ ID NO: 36;

(m) the heavy chain variable region comprises a CDRH1 comprising the amino acid sequence of SEQ ID NO: 94; a CDRH2 comprising the amino acid sequence of SEQ ID NO: 95; and a CDRH3 comprising the amino acid sequence of SEQ ID NO: 96; and the light chain variable region comprises a CDRL1 comprising the amino acid sequence of SEQ ID NO: 37; a CDRL2 comprising the amino acid sequence of SEQ ID NO: 38; and a CDRL3 comprising the amino acid sequence of SEQ ID NO: 39;

(n) the heavy chain variable region comprises a CDRH1 comprising the amino acid sequence of SEQ ID NO: 97; a CDRH2 comprising the amino acid sequence of SEQ ID NO: 98; and a CDRH3 comprising the amino acid sequence of SEQ ID NO: 99; and the light chain variable region comprises a CDRL1 comprising the amino acid sequence of SEQ ID NO: 40; a CDRL2 comprising the amino acid sequence of SEQ ID NO: 41; and a CDRL3 comprising the amino acid sequence of SEQ ID NO: 42;

(o) the heavy chain variable region comprises a CDRH1 comprising the amino acid sequence of SEQ ID NO: 100; a CDRH2 comprising the amino acid sequence of SEQ ID NO: 101; and a CDRH3 comprising the amino acid sequence of SEQ ID NO: 102; and the light chain variable region comprises a CDRL1 comprising the amino acid sequence of SEQ ID NO: 43; a CDRL2 comprising the amino acid sequence of SEQ ID NO: 44; and a CDRL3 comprising the amino acid sequence of SEQ ID NO: 45;

(p) the heavy chain variable region comprises a CDRH1 comprising the amino acid sequence of SEQ ID NO: 103; a CDRH2 comprising the amino acid sequence of SEQ ID NO: 104; and a CDRH3 comprising the amino acid sequence of SEQ ID NO: 105; and the light chain variable region comprises a CDRL1 comprising the amino acid sequence of SEQ ID NO: 46; a CDRL2 comprising the amino acid sequence of SEQ ID NO: 47; and a CDRL3 comprising the amino acid sequence of SEQ ID NO: 48;

(q) the heavy chain variable region comprises a CDRH1 comprising the amino acid sequence of SEQ ID NO: 106; a CDRH2 comprising the amino acid sequence of SEQ ID NO: 107; and a CDRH3 comprising the amino acid sequence of SEQ ID NO: 108; and the light chain variable region comprises a CDRL1 comprising the amino acid sequence of SEQ ID NO: 49; a CDRL2 comprising the amino acid sequence of SEQ ID NO: 50; and a CDRL3 comprising the amino acid sequence of SEQ ID NO: 51;

(r) the heavy chain variable region comprises a CDRH1 comprising the amino acid sequence of SEQ ID NO: 109; a CDRH2 comprising the amino acid sequence of SEQ ID NO: 110; and a CDRH3 comprising the amino acid sequence of SEQ ID NO: 111; and the light chain variable region comprises a CDRL1 comprising the amino acid sequence of SEQ ID NO: 52; a CDRL2 comprising the amino acid sequence of SEQ ID NO: 53; and a CDRL3 comprising the amino acid sequence of SEQ ID NO: 54;

(s) the heavy chain variable region comprises a CDRH1 comprising the amino acid sequence of SEQ ID NO: 112; a CDRH2 comprising the amino acid sequence of SEQ ID NO: 113; and a CDRH3 comprising the amino acid sequence of SEQ ID NO: 114; and the light chain variable region comprises a CDRL1 comprising the amino acid sequence of SEQ ID NO: 55; a CDRL2 comprising the amino acid sequence of SEQ ID NO: 56; and a CDRL3 comprising the amino acid sequence of SEQ ID NO: 57; and doppel-binding fragments of any thereof.

2. A doppel-targeting molecule that binds to doppel, wherein the doppel targeting molecule comprises a heavy chain variable region and a light chain variable region, wherein:

(a) the heavy chain variable regions comprises the amino acid sequence of SEQ ID NO: 134 and the light chain variable region comprises the amino acid sequence of SEQ ID NO: 115;

(b) the heavy chain variable regions comprises the amino acid sequence of SEQ ID NO: 135 and the light chain variable region comprises the amino acid sequence of SEQ ID NO: 116;

(c) the heavy chain variable regions comprises the amino acid sequence of SEQ ID NO: 136 and the light chain variable region comprises the amino acid sequence of SEQ ID NO: 117;

(d) the heavy chain variable regions comprises the amino acid sequence of SEQ ID NO: 137 and the light chain variable region comprises the amino acid sequence of SEQ ID NO: 118;

(e) the heavy chain variable regions comprises the amino acid sequence of SEQ ID NO: 138 and the light chain variable region comprises the amino acid sequence of SEQ ID NO: 119;

(f) the heavy chain variable regions comprises the amino acid sequence of SEQ ID NO: 139 and the light chain variable region comprises the amino acid sequence of SEQ ID NO: 120;

(g) the heavy chain variable regions comprises the amino acid sequence of SEQ ID NO: 140 and the light chain variable region comprises the amino acid sequence of SEQ ID NO: 121;

(h) the heavy chain variable regions comprises the amino acid sequence of SEQ ID NO: 141 and the light chain variable region comprises the amino acid sequence of SEQ ID NO: 122;

(i) the heavy chain variable regions comprises the amino acid sequence of SEQ ID NO: 142 and the light chain variable region comprises the amino acid sequence of SEQ ID NO: 123;

(j) the heavy chain variable regions comprises the amino acid sequence of SEQ ID NO: 143 and the light chain variable region comprises the amino acid sequence of SEQ ID NO: 124;

(k) the heavy chain variable regions comprises the amino acid sequence of SEQ ID NO: 144 and the light chain variable region comprises the amino acid sequence of SEQ ID NO: 125;

(1) the heavy chain variable regions comprises the amino acid sequence of SEQ ID NO: 145 and the light chain variable region comprises the amino acid sequence of SEQ ID NO: 126;

(m) the heavy chain variable regions comprises the amino acid sequence of SEQ ID NO: 146 and the light chain variable region comprises the amino acid sequence of SEQ ID NO: 127;

(n) the heavy chain variable regions comprises the amino acid sequence of SEQ ID NO: 147 and the light chain variable region comprises the amino acid sequence of SEQ ID NO: 128;

(o) the heavy chain variable regions comprises the amino acid sequence of SEQ ID NO: 148 and the light chain variable region comprises the amino acid sequence of SEQ ID NO: 129;

(p) the heavy chain variable regions comprises the amino acid sequence of SEQ ID NO: 149 and the light chain variable region comprises the amino acid sequence of SEQ ID NO: 130;

(q) the heavy chain variable regions comprises the amino acid sequence of SEQ ID NO: 150 and the light chain variable region comprises the amino acid sequence of SEQ ID NO: 131;

(r) the heavy chain variable regions comprises the amino acid sequence of SEQ ID NO: 151 and the light chain variable region comprises the amino acid sequence of SEQ ID NO: 132; or (s) the heavy chain variable regions comprises the amino acid sequence of SEQ ID NO: 152 and the light chain variable region comprises the amino acid sequence of SEQ ID NO: 133;

and doppel-binding fragments of any thereof.

3. A doppel-targeting molecule that binds to doppel, wherein the doppel-targeting molecule is selected from a doppel-binding murine antibody produced by a hybridoma cell line clone selected from:

(i) Hybridoma cell line clone 2B6, deposited on Sep. 29, 2020 with Korean Cell Line Research Foundation as hPrnd #2B6 under Accession Number KCLRF-BP-00490;

(ii) Hybridoma cell line clone 2A8, deposited on Sep. 29, 2020 with Korean Cell Line Research Foundation as mPrnd #2A8 under Accession Number KCLRF-BP-00489;

(iii) Hybridoma cell line clone 7A11, deposited on Oct. 19, 2020 with Korean Cell Line Research Foundation as hPrnd #7A11 under Accession Number KCLRF-BP-00498;

(iv) Hybridoma cell line clone 7G3, deposited on Oct. 19, 2020 with Korean Cell Line Research Foundation as hPrnd #7G3 under Accession Number KCLRF-BP-00500;

(v) Hybridoma cell line clone 2E9, deposited on Sep. 29, 2020 with Korean Cell Line Research Foundation as hPrnd #2E9 under Accession Number KCLRF-BP-00493;

(vi) Hybridoma cell line clone 4E3, deposited on Oct. 19, 2020 with Korean Cell Line Research Foundation as hPrnd #4E3 under Accession Number KCLRF-BP-00495;

(vii) Hybridoma cell line clone 4H7, deposited on Oct. 19, 2020 with Korean Cell Line Research Foundation as hPrnd #4H7 under Accession Number KCLRF-BP-00496;

(viii) Hybridoma cell line clone 2C10, deposited on Sep. 29, 2020 with Korean Cell Line Research Foundation as hPrnd #2C10 under Accession Number KCLRF-BP-00491;

(ix) Hybridoma cell line clone 2C12, deposited on Sep. 29, 2020 with Korean Cell Line Research Foundation as hPrnd #2C12 under Accession Number KCLRF-BP-00492;

(x) Hybridoma cell line clone 5D3, deposited on Oct. 19, 2020 with Korean Cell Line Research Foundation as hPrnd #5D3 under Accession Number KCLRF-BP-00497;

(xi) Hybridoma cell line clone 4D5, deposited on Oct. 19, 2020 with Korean Cell Line Research Foundation as hPrnd #4D5 under Accession Number KCLRF-BP-00494; and (xii) Hybridoma cell line clone 7D7, deposited on Oct. 19, 2020 with Korean Cell Line Research Foundation as hPrnd #7D7 under Accession Number KCLRF-BP-00499, and doppel-binding fragments thereof.

4. The doppel-targeting molecule of claim 1, wherein:

(a) the heavy chain variable regions comprises the amino acid sequence of SEQ ID NO: 134 and the light chain variable region comprises the amino acid sequence of SEQ ID NO: 115;

(h) the heavy chain variable regions comprises the amino acid sequence of SEQ ID NO: 141 and the light chain variable region comprises the amino acid sequence of SEQ ID NO: 122;

(p) the heavy chain variable regions comprises the amino acid sequence of SEQ ID NO: 149 and the light chain variable region comprises the amino acid sequence of SEQ ID NO: 130;

(q) the heavy chain variable regions comprises the amino acid sequence of SEQ ID NO: 150 and the light chain variable region comprises the amino acid sequence of SEQ ID NO: 131;

(r) the heavy chain variable regions comprises the amino acid sequence of SEQ ID NO: 151 and the light chain variable region comprises the amino acid sequence of SEQ ID NO: 132; or (s) the heavy chain variable regions comprises the amino acid sequence of SEQ ID NO: 152 and the light chain variable region comprises the amino acid sequence of SEQ ID NO: 133; and wherein the doppel-targeting molecule interferes with interaction of doppel and VEGFR2.

5. A pharmaceutical composition comprising a doppel-targeting molecule according to claim 1 and a pharmaceutically acceptable carrier or diluent.

6. The pharmaceutical composition of claim 5, wherein the composition is formulated for a route of administration selected from oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, and topical administration.

7. The pharmaceutical composition of claim 6, wherein the doppel-targeting molecule is an anti-doppel antibody or a doppel-binding fragment of an anti-doppel antibody, and is formulated for intravenous injection.

8. The doppel-targeting molecule of claim 1, wherein the doppel-targeting molecule is a monoclonal antibody.

9. A pharmaceutical composition comprising a monoclonal antibody according to claim 8 and a pharmaceutically acceptable carrier or diluent.

10. An in vitro method of detecting doppel expression in a subject, comprising (i) contacting a doppel-targeting molecule according to claim 1 with a physiological sample obtained from the subject, and (ii) detecting any binding between the doppel-targeting molecule and any doppel present in the sample.

11. The method of claim 10, wherein the doppel-targeting molecule is labeled with or includes a detectable label.

12. The method of claim 10, wherein the subject suffers from or is at risk of developing a disease or condition selected from one or more of tumor, cancer, atherosclerosis, tuberculosis, asthma, pulmonary arterial hypertension (PAH), a neoplasm, and a neoplasm-related condition.

13. A method of inhibiting pathological angiogenesis in a subject in need thereof, comprising administering to the subject an effective amount of a doppel-targeting molecule according to claim 1.

14. The method of claim 13, wherein the effective amount is effective to inhibit angiogenesis.

15. The method of claim 13, wherein the doppel-targeting molecule is administered by a route selected from oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, and topical administration.

16. The method of claim 13, wherein the doppel-targeting molecule is administered by intravenous injection.

17. The method of claim 13, wherein the subject suffers from or is at risk of developing a tumor, and the effective amount is effective to inhibit tumorigenesis and/or to decrease tumor vasculature.

18. The method of claim 13, wherein the subject suffers from or is at risk of developing a disease or condition selected from one or more of cancer, a neoplasm, and a neoplasm-related condition, and the effective amount is effective to decrease pathological vasculature associated with the cancer, neoplasm, or neoplasm-related condition, respectively.

19. The method of claim 18, wherein the neoplasm or neoplasm-related condition is selected from breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and Meigs' syndrome.

20. The method of claim 13, wherein the subject is a human.

21. An in vivo method of detecting doppel expression in a subject, comprising (i) administering to the subject a doppel-targeting molecule according to claim 1 wherein the doppel-targeting molecule is labeled with or includes a detectable label, and (ii) detecting any binding between the doppel-targeting molecule and any doppel expressed in the subject.

22. The method of claim 20, wherein the subject suffers from or is at risk of composition, atherosclerosis, tuberculosis, asthma, and pulmonary arterial hypertension (PAH), a neoplasm, and a neoplasm-related condition.

23. A doppel-targeting molecule that binds to doppel, wherein the doppel-targeting molecule is selected from:

(a) a chimeric antibody, wherein the chimeric antibody comprises a variable heavy chain region and variable light chain region from any one of mouse antibodies produced by a hybridoma cell line clone selected from the group consisting of:

(i) Hybridoma cell line clone 2B6, deposited on Sep. 29, 2020 with Korean Cell Line Research Foundation as hPrnd #2B6 under Accession Number KCLRF-BP-00490, (ii) Hybridoma cell line clone 2A8, deposited on Sep. 29, 2020 with Korean Cell Line Research Foundation as mPrnd #2A8 under Accession Number KCLRF-BP-00489, (iii) Hybridoma cell line clone 7A11, deposited on Oct. 19, 2020 with Korean Cell Line Research Foundation as hPrnd #7A11 under Accession Number KCLRF-BP-00498, (iv) Hybridoma cell line clone 7G3, deposited on Oct. 19, 2020 with Korean Cell Line Research Foundation as hPrnd #7G3 under Accession Number KCLRF-BP-00500, (v) Hybridoma cell line clone 2E9, deposited on Sep. 29, 2020 with Korean Cell Line Research Foundation as hPrnd #2E9 under Accession Number KCLRF-BP-00493, (vi) Hybridoma cell line clone 4E3, deposited on Oct. 19, 2020 with Korean Cell Line Research Foundation as hPrnd #4E3 under Accession Number KCLRF-BP-00495, (vii) Hybridoma cell line clone 4H7, deposited on Oct. 19, 2020 with Korean Cell Line Research Foundation as hPrnd #4H7 under Accession Number KCLRF-BP-00496, (viii) Hybridoma cell line clone 2C10, deposited on Sep. 29, 2020 with Korean Cell Line Research Foundation as hPrnd #2C10 under Accession Number KCLRF-BP-00491, (ix) Hybridoma cell line clone 2C12, deposited on Sep. 29, 2020 with Korean Cell Line Research Foundation as hPrnd #2C12 under Accession Number KCLRF-BP-00492, (x) Hybridoma cell line clone 5D3, deposited on Oct. 19, 2020 with Korean Cell Line Research Foundation as hPrnd #5D3 under Accession Number KCLRF-BP-00497, (xi) Hybridoma cell line clone 4D5, deposited on Oct. 19, 2020 with Korean Cell Line Research Foundation as hPrnd #4D5 under Accession Number KCLRF-BP-00494; and (xii) Hybridoma cell line clone 7D7, deposited on Oct. 19, 2020 with Korean Cell Line Research Foundation as hPrnd #7D7 under Accession Number KCLRF-BP-00499, and a constant heavy chain region and constant light chain region from a human antibody; and (b) a humanized antibody, wherein the humanized antibody comprises the CDR regions from any one of mouse antibodies produced by a hybridoma cell line clone selected from the group consisting of:

(i) Hybridoma cell line clone 2B6, deposited on Sep. 29, 2020 with Korean Cell Line Research Foundation as hPrnd #2B6 under Accession Number KCLRF-BP-00490;

(ii) Hybridoma cell line clone 2A8, deposited on Sep. 29, 2020 with Korean Cell Line Research Foundation as mPrnd #2A8 under Accession Number KCLRF-BP-00489;

(iii) Hybridoma cell line clone 7A11, deposited on Oct. 19, 2020 with Korean Cell Line Research Foundation as hPrnd #7A11 under Accession Number KCLRF-BP-00498;

(iv) Hybridoma cell line clone 7G3, deposited on Oct. 19, 2020 with Korean Cell Line Research Foundation as hPrnd #7G3 under Accession Number KCLRF-BP-00500;

(v) Hybridoma cell line clone 2E9, deposited on Sep. 29, 2020 with Korean Cell Line Research Foundation as hPrnd #2E9 under Accession Number KCLRF-BP-00493;

(vi) Hybridoma cell line clone 4E3, deposited on Oct. 19, 2020 with Korean Cell Line Research Foundation as hPrnd #4E3 under Accession Number KCLRF-BP-00495;

(vii) Hybridoma cell line clone 4H7, deposited on Oct. 19, 2020 with Korean Cell Line Research Foundation as hPrnd #4H7 under Accession Number KCLRF-BP-00496;

(viii) Hybridoma cell line clone 2C10, deposited on Sep. 29, 2020 with Korean Cell Line Research Foundation as hPrnd #2C10 under Accession Number KCLRF-BP-00491;

(ix) Hybridoma cell line clone 2C12, deposited on Sep. 29, 2020 with Korean Cell Line Research Foundation as hPrnd #2C12 under Accession Number KCLRF-BP-00492;

(x) Hybridoma cell line clone 5D3, deposited on Oct. 19, 2020 with Korean Cell Line Research Foundation as hPrnd #5D3 under Accession Number KCLRF-BP-00497;

(xi) Hybridoma cell line clone 4D5, deposited on Oct. 19, 2020 with Korean Cell Line Research Foundation as hPrnd #4D5 under Accession Number KCLRF-BP-00494; and (xii) Hybridoma cell line clone 7D7, deposited on Oct. 19, 2020 with Korean Cell Line Research Foundation as hPrnd #7D7 under Accession Number KCLRF-BP-00499, and variable heavy chain, variable light chain, constant heavy chain, and constant light chain regions from a human antibody; and doppel-binding fragments of any thereof.

24. A doppel-targeting molecule according to claim 23, wherein the doppel-targeting molecule is selected from:

a chimeric antibody comprising a light chain that comprises the amino acid sequence of SEQ ID NO: 155 and a heavy chain that comprises the amino acid sequence of SEQ ID NO: 157, and doppel-binding fragments thereof;

a chimeric antibody comprising a light chain that comprises the amino acid sequence of SEQ ID NO: 159 and a heavy chain that comprises the amino acid sequence of SEQ ID NO: 161,and doppel-binding fragments thereof;

a humanized antibody comprising a light chain that comprises the amino acid sequence of SEQ ID NO: 163 and a heavy chain that comprises the amino acid sequence of SEQ ID NO: 165, and doppel-binding fragments thereof;

a humanized antibody comprising a light chain that comprises the amino acid sequence of SEQ ID NO: 167 and a heavy chain that comprises the amino acid sequence of SEQ ID NO: 169, and doppel-binding fragments thereof.

25. A doppel-targeting molecule according to claim 1, wherein the doppel targeting molecule comprises a heavy chain variable region and a light chain variable region, wherein:

(a) the heavy chain variable regions comprises the amino acid sequence of SEQ ID NO: 134 and the light chain variable region comprises the amino acid sequence of SEQ ID NO: 115;

(b) the heavy chain variable regions comprises the amino acid sequence of SEQ ID NO: 135 and the light chain variable region comprises the amino acid sequence of SEQ ID NO: 116;

(c) the heavy chain variable regions comprises the amino acid sequence of SEQ ID NO: 136 and the light chain variable region comprises the amino acid sequence of SEQ ID NO: 117;

(d) the heavy chain variable regions comprises the amino acid sequence of SEQ ID NO: 137 and the light chain variable region comprises the amino acid sequence of SEQ ID NO: 118;

(e) the heavy chain variable regions comprises the amino acid sequence of SEQ ID NO: 138 and the light chain variable region comprises the amino acid sequence of SEQ ID NO: 119;

(f) the heavy chain variable regions comprises the amino acid sequence of SEQ ID NO: 139 and the light chain variable region comprises the amino acid sequence of SEQ ID NO: 120;

(g) the heavy chain variable regions comprises the amino acid sequence of SEQ ID NO: 140 and the light chain variable region comprises the amino acid sequence of SEQ ID NO: 121;

(h) the heavy chain variable regions comprises the amino acid sequence of SEQ ID NO: 141 and the light chain variable region comprises the amino acid sequence of SEQ ID NO: 122;

(i) the heavy chain variable regions comprises the amino acid sequence of SEQ ID NO: 142 and the light chain variable region comprises the amino acid sequence of SEQ ID NO: 123;

(j) the heavy chain variable regions comprises the amino acid sequence of SEQ ID NO: 143 and the light chain variable region comprises the amino acid sequence of SEQ ID NO: 124;

(k) the heavy chain variable regions comprises the amino acid sequence of SEQ ID NO: 144 and the light chain variable region comprises the amino acid sequence of SEQ ID NO: 125; or (1) the heavy chain variable regions comprises the amino acid sequence of SEQ ID NO: 145 and the light chain variable region comprises the amino acid sequence of SEQ ID NO: 126.

26. A doppel-targeting molecule according to claim 1, wherein the doppel targeting molecule comprises a heavy chain variable region and a light chain variable region, wherein:

(m) the heavy chain variable regions comprises the amino acid sequence of SEQ ID NO: 146 and the light chain variable region comprises the amino acid sequence of SEQ ID NO: 127;

(n) the heavy chain variable regions comprises the amino acid sequence of SEQ ID NO: 147 and the light chain variable region comprises the amino acid sequence of SEQ ID NO: 128;

(o) the heavy chain variable regions comprises the amino acid sequence of SEQ ID NO: 148 and the light chain variable region comprises the amino acid sequence of SEQ ID NO: 129;

(p) the heavy chain variable regions comprises the amino acid sequence of SEQ ID NO: 149 and the light chain variable region comprises the amino acid sequence of SEQ ID NO: 130;

(q) the heavy chain variable regions comprises the amino acid sequence of SEQ ID NO: 150 and the light chain variable region comprises the amino acid sequence of SEQ ID NO: 131;

(r) the heavy chain variable regions comprises the amino acid sequence of SEQ ID NO: 151 and the light chain variable region comprises the amino acid sequence of SEQ ID NO: 132; or (s) the heavy chain variable regions comprises the amino acid sequence of SEQ ID NO: 152 and the light chain variable region comprises the amino acid sequence of SEQ ID NO: 133.

27. A doppel-targeting molecule according to claim 23, wherein the doppel-targeting molecule is selected from:

a chimeric antibody comprising a light chain that comprises the amino acid sequence of SEQ ID NO: 155 and a heavy chain that comprises the amino acid sequence of SEQ ID NO: 157;

a chimeric antibody comprising a light chain that comprises the amino acid sequence of SEQ ID NO: 159 and a heavy chain that comprises the amino acid sequence of SEQ ID NO: 161;

a humanized antibody comprising a light chain that comprises the amino acid sequence of SEQ ID NO: 163 and a heavy chain that comprises the amino acid sequence of SEQ ID NO: 165;

a humanized antibody comprising a light chain that comprises the amino acid sequence of SEQ ID NO: 167 and a heavy chain that comprises the amino acid sequence of SEQ ID NO: 169.

* * * * *

SEQUENCE LISTING

```
<160> NUMBER OF SEQ ID NOS: 170

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Asn Val Asp Ala Asn
1               5


<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser
1


<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Asn Ser Tyr Pro Phe Thr
1               5


<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Leu Leu Tyr Ser Ser Asn Gln Lys Asn Tyr
1               5                   10


<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Trp Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gln Gln Tyr Tyr Ser Tyr Pro Leu Thr
1 5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Gln Ser Ile Val Gln Ser Asn Gly Asn Thr Tyr
1 5 10

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Lys Val Ser
1

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Phe Gln Gly Ser His Val Pro Leu Thr
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ser Ser Val Ser Ser Ser Tyr
1 5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ser Thr Ser
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

His Gln Tyr His Arg Ser Pro Leu Thr
1 5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Arg Gly Ile Ser Asn Tyr
1 5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Tyr Thr Ser
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Gln Gln Tyr Ser Lys Leu Pro Ser Thr
1 5

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gln Ser Leu Leu Tyr Ser Ser Asn Gln Lys Asn Tyr
1 5 10

```
<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ala Ser
1


<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Tyr Tyr Ser Tyr Pro Leu Thr
1               5


<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Leu Leu Tyr Ser Ser Asn Gln Lys Asn Tyr
1               5                   10


<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Ala Ser
1


<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Tyr Tyr Thr Tyr Pro Leu Ser
1               5


<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 22

Lys Ser Ile Ser Lys Tyr
1 5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ser Gly Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Gln Gln His Ser Glu Tyr Pro Trp Thr
1 5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Ser Ser Val Asn Tyr
1 5

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Leu Thr Ser
1

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gln Gln Trp Ser Ser Asn Pro Trp Thr
1 5

<210> SEQ ID NO 28
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 28

Glu Ser Val Asp Ser Tyr Gly Asn Ser Phe
1               5                   10


<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser
1


<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Ser Asn Glu Asp Leu Thr
1               5


<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Val Asn Tyr
1               5


<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Thr Ser
1


<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Trp Ser Ser Asn Pro Trp Thr
1               5
```

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Thr Gly Ala Val Thr Thr Ser Asn Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gly Thr Asn
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ala Leu Trp Tyr Ser Asn His Trp Val
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Arg Ala Ser Gln Ser Ile Gly Ser Tyr Leu Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Ala Ala Ser Thr Leu Gln Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gln Gln Ser Tyr Ser Phe Pro Trp Thr
1 5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Arg Ala Ser Gln Ser Ile Ser Asn Tyr Leu Asn
1 5 10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ala Ala Ser Arg Leu Gln Ser
1 5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gln Gln Ser Tyr Ser Phe Pro Trp Thr
1 5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Arg Ala Ser Gln Ser Ile Arg Asn Tyr Leu Asn
1 5 10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Ala Ala Ser Asn Leu Gln Ser
1 5

<210> SEQ ID NO 45
<211> LENGTH: 9

<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gln Gln Ser Ser Ser Phe Pro Leu Thr
1 5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Arg Ala Ser Gln Ser Ile Ser Ser Tyr Leu Asn
1 5 10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Ala Ala Ser Ser Leu Gln Ser
1 5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Gln Gln Ser Glu Ser Phe Pro Leu Thr
1 5

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Arg Ala Ser Gln Ser Ile Ser Asn Trp Leu Asn
1 5 10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Ala Thr Ser Ser Leu Gln Ser 1 5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gln Gln Ser Tyr Ser Tyr Pro Trp Thr
1 5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Arg Ala Ser Gln Ser Ile Ser Asn Tyr Leu Asn
1 5 10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Ala Ala Ser Thr Leu Gln Ser
1 5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gln Gln Ser Tyr Ser Thr Pro Trp Thr
1 5

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Arg Ala Ser Gln Ser Ile Ser Asn Tyr Leu Asn
1 5 10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Ala Ala Ser Thr Leu Gln Ser
1 5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Gln Gln Ser Tyr Ser Phe Pro Tyr Thr
1 5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Gly Phe Thr Phe Thr Asp Tyr Ala
1 5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ile Ser Ser Tyr Tyr Gly Asp Ala
1 5

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ala Arg Arg Leu Arg Gly Ala Met Asp Tyr
1 5 10

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Gly Tyr Ser Ile Thr Ser Gly Tyr Ser
1 5

<210> SEQ ID NO 62

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Ile His Tyr Ser Gly Ser Thr
1 5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Ala Arg Leu Tyr Gly Trp Tyr Phe Asp Val
1 5 10

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Gly Tyr Thr Phe Thr Ser Tyr Trp
1 5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Ile Tyr Pro Ser Asp Ser Tyr Thr
1 5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Thr Arg Ser Met Ile Thr
1 5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

```
Gly Tyr Ser Phe Thr Asp Tyr Ile
1               5


<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Asn Pro Tyr Tyr Gly Ser Thr
1               5


<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Arg Arg Asn Tyr Tyr Gly Asn Tyr Asp Ala Met Asp Tyr
1               5                   10


<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Phe Thr Phe Thr Asp Tyr Tyr
1               5


<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Arg Asn Lys Ala Asn Gly Tyr Thr Thr
1               5                   10


<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Arg Gly Asp Gly Tyr Tyr Gly Tyr Phe Asp Tyr
1               5                   10


<210> SEQ ID NO 73
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 73

Gly Phe Thr Phe Thr Asp Tyr Tyr
1               5

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Arg Asn Lys Ala Asn Gly Tyr Thr Thr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Asp Gly Tyr Tyr Gly Tyr Phe Asp Tyr
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Ser Ile Thr Ser Gly Tyr Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile His Tyr Ser Gly Asn Thr
1               5

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Met Arg Thr Tyr Tyr Tyr Gly Pro Leu Asp Tyr
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Gly Asp Ser Ile Thr Ser Gly Tyr
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Ile Arg Tyr Ser Gly Ser Ala
1               5

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Ala Arg Tyr Pro Tyr Tyr Gly Ser Tyr Trp Tyr Phe Asp Val
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gly Phe Ser Leu Thr Gly Tyr Gly
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Ile Trp Gly Asp Gly Asn Thr
1               5

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Ala Arg Asp Arg Asp Tyr Tyr Gly Ser Ile Pro Phe Ala Tyr
1 5 10

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Gly Tyr Ser Phe Thr Gly Tyr Asn
1 5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Ile Asp Pro Tyr Tyr Gly Gly Ser
1 5

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Ala Arg Val Arg Tyr Asp Tyr Ser Leu Met Asp Tyr
1 5 10

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gly Phe Ser Leu Thr Ser Tyr Gly
1 5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Ile Trp Ala Ala Gly Ser Thr
1 5

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Ala Arg Arg Asp Gly Asn Tyr Arg Gly Phe Ala Tyr
1 5 10

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Gly Asp Ser Phe Thr Arg Tyr Trp
1 5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Ile Tyr Pro Gly Asn Ser Asp Thr
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Thr Arg Gly Gly Tyr Gly Pro Tyr
1 5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Ser Tyr Ala Met Ser
1 5

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Ala Ile Ser Ser Asp Gly Gly Ser Thr Tyr Tyr Ala Asp Ser Val Lys
1 5 10 15

Gly

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Arg Arg Leu Trp Ser Tyr Ser Phe Asp Tyr
1 5 10

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Asp Tyr Ala Met Ser
1 5

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Ala Ile Ser Ser Ser Gly Gly Ser Thr Tyr Tyr Ala Asp Ser Val Lys
1 5 10 15

Gly

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Leu Tyr Tyr Thr Tyr Glu Val Leu Asp Ile
1 5 10

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Ser Tyr Tyr Met His
1 5

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Arg Ile Ser Pro Gly Gly Gly Gly Thr Ile Tyr Ala Gln Lys Phe Gln
1 5 10 15

Gly

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Ala Gln Ser Glu Gly Leu Ser Tyr Tyr Phe Asp Val
1 5 10

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Asp Tyr Ala Met Ser
1 5

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Arg Ile Ser Ser Ser Gly Ser Ser Lys Tyr Tyr Ala Asp Ser Val Lys
1 5 10 15

Gly

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Trp Gly Ser Tyr Gly Tyr Gly Leu Val Tyr Tyr Phe Asp Val
1 5 10

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

```
Asp Tyr Ala Met Ser
1               5


<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ile Ser Gly Ser Gly Gly Thr Lys Tyr Tyr Ala Asp Ser Val Lys
1               5                   10                  15

Gly


<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Gln Val Tyr Trp Ala Leu Asp Val
1               5


<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Tyr Ala Met Ser
1               5


<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Ile Ser Ser Ser Gly Gly Glu Lys Tyr Tyr Ala Asp Ser Val Lys
1               5                   10                  15

Gly


<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

His Gly Tyr Gly Gln Glu Tyr Tyr Tyr Phe Asp Val
1               5                   10
```

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Ser Tyr Ala Met Ser
1 5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gly Ile Ser Gly Ser Gly Ser Arg Thr Asp Tyr Ala Asp Ser Val Lys
1 5 10 15

Gly

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Val Tyr Thr Tyr Thr Arg Gly Phe Ala Phe Asp Leu
1 5 10

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Asp Ala Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Tyr Arg Phe Thr Gly
50 55 60

Ser Gly Ser Gly Thr Asp Phe Thr Leu Thr Ile Ser Asn Val Gln Ser
65 70 75 80

Ala Asp Leu Ala Glu Tyr Phe Cys Gln Gln Tyr Asn Ser Tyr Pro Phe
85 90 95

Thr Phe Gly Ser Gly Thr Lys Leu Glu Leu Lys
100 105

<210> SEQ ID NO 116
<211> LENGTH: 113
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 116

```
Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys
```

<210> SEQ ID NO 117
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 118
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

```
Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30
```

```
Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Thr Ala Thr Tyr Tyr Cys His Gln Tyr His Arg Ser Pro
                85                  90                  95

Leu Thr Phe Gly Ala Gly Thr Lys Leu Glu Leu Lys
            100                 105
```

<210> SEQ ID NO 119
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

```
Asp Val Gln Met Thr Gln Thr Thr Ser Ser Leu Ser Ala Ser Leu Gly
1               5                   10                  15

Asp Arg Val Thr Ile Ser Cys Ser Ala Ser Arg Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Pro Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Ser
                85                  90                  95

Thr Phe Gly Gly Gly Thr Lys Val Glu Ile Lys
            100                 105
```

<210> SEQ ID NO 120
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110
```

Lys

<210> SEQ ID NO 121
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Asp Ile Val Met Ser Gln Ser Pro Ser Ser Leu Pro Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Tyr Pro Leu Ser Phe Gly Ala Gly Thr Lys Leu Glu Leu
            100                 105                 110

Lys
```

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Asp Val Gln Ile Thr Gln Ser Pro Ser Tyr Leu Ala Ala Ser Pro Gly
1               5                   10                  15

Glu Thr Ile Thr Leu Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Met Tyr Tyr Cys Gln Gln His Ser Glu Tyr Pro Trp
                85                  90                  95

Thr Phe Gly Gly Gly Thr Lys Leu Glu Ile Lys
            100                 105
```

<210> SEQ ID NO 123
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Ile
            20                  25                  30

Tyr Trp Tyr Gln Gln Lys Pro Gly Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105


<210> SEQ ID NO 124
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Ser Tyr Tyr Cys Gln Gln Ser Asn
                85                  90                  95

Glu Asp Leu Thr Phe Gly Ala Gly Thr Lys Leu Glu Leu Lys
            100                 105                 110


<210> SEQ ID NO 125
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Ile Val Leu Ser Gln Ser Pro Ala Leu Met Ser Ala Ser Pro Gly
1               5                   10                  15

Glu Lys Val Thr Met Thr Cys Ser Ala Ser Ser Ser Val Asn Tyr Ile
            20                  25                  30

Tyr Trp Tyr Gln Gln Lys Pro Gly Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80
```

```
Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105


<210> SEQ ID NO 126
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105


<210> SEQ ID NO 127
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 128
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 129
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 130
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Ser Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 131
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 132
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 133
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 134
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Gln Ser Gly Ala Glu Leu Val Arg Pro Gly Val
1               5                   10                  15

Ser Val Lys Leu Ser Cys Lys Phe Ser Gly Phe Thr Phe Thr Asp Tyr
            20                  25                  30

Ala Met His Trp Val Arg Gln Ser His Ala Lys Ser Leu Ala Trp Ile
        35                  40                  45

Gly Val Ile Ser Ser Tyr Tyr Gly Asp Ala Ser Tyr Asn Gln Lys Phe
    50                  55                  60

Thr Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Arg Leu Arg Gly Ala Met Asp Tyr Trp Gly Gln Gly Thr Ser
            100                 105                 110

Val Thr Val Ser Ser
        115


<210> SEQ ID NO 135
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Leu Tyr Gly Trp Tyr Phe Asp Val Trp Gly Ala Gly Thr Thr
```

```
            100                 105                 110

Val Thr Val Ser Ser
        115


<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Met Ile Thr Trp Gly Gln Gly Thr Thr Leu Thr Val Ser
            100                 105                 110

Ser


<210> SEQ ID NO 137
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Leu Trp Val Lys Gln Ser His Gly Lys Ser Leu Glu Trp Ile
        35                  40                  45

Gly Asn Ile Asn Pro Tyr Tyr Gly Ser Thr Ser Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asn Tyr Tyr Gly Asn Tyr Asp Ala Met Asp Tyr Trp Gly
            100                 105                 110

Gln Gly Thr Ser Val Thr Val Ser Ser
        115                 120


<210> SEQ ID NO 138
<211> LENGTH: 121
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 138

Glu Val Lys Leu Val Glu Ser Gly Gly Asp Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Thr Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Phe
                85                  90                  95

Tyr Cys Ala Arg Gly Asp Gly Tyr Tyr Gly Tyr Phe Asp Tyr Trp Gly
            100                 105                 110

Gln Gly Thr Thr Leu Thr Val Ser Ser
        115                 120


<210> SEQ ID NO 139
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Lys Leu Val Glu Ser Gly Gly Asp Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Thr Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Phe
                85                  90                  95

Tyr Cys Ala Arg Gly Asp Gly Tyr Tyr Gly Tyr Phe Asp Tyr Trp Gly
            100                 105                 110

Gln Gly Thr Thr Leu Thr Val Ser Ser
        115                 120


<210> SEQ ID NO 140
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Val Gln Leu Gln Glu Ser Gly Pro Asp Leu Val Lys Pro Ser Gln
1               5                   10                  15
```

```
Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Asn Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Ser Cys
                85                  90                  95

Ala Met Arg Thr Tyr Tyr Tyr Gly Pro Leu Asp Tyr Trp Gly Gln Gly
            100                 105                 110

Thr Thr Leu Thr Val Ser Ser
        115
```

```
<210> SEQ ID NO 141
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Arg Tyr Ser Gly Ser Ala Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Pro Tyr Tyr Gly Ser Tyr Trp Tyr Phe Asp Val Trp Gly Ala
            100                 105                 110

Gly Thr Thr Val Thr Val Ser Ser
        115                 120
```

```
<210> SEQ ID NO 142
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60
```

```
Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Arg Asp Tyr Tyr Gly Ser Ile Pro Phe Ala Tyr Trp Gly Gln
            100                 105                 110

Gly Thr Leu Val Thr Val Ser Ala
        115                 120


<210> SEQ ID NO 143
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Lys Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Gly Ser Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Val Arg Tyr Asp Tyr Ser Leu Met Asp Tyr Trp Gly Gln Gly
            100                 105                 110

Thr Ser Val Thr Val Ser Ser
        115


<210> SEQ ID NO 144
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Ala Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Arg Asp Gly Asn Tyr Arg Gly Phe Ala Tyr Trp Gly Gln Gly Thr
            100                 105                 110
```

```
Leu Val Thr Val Ser Ala
        115


<210> SEQ ID NO 145
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Gln Glu Ser Gly Thr Val Leu Ala Arg Pro Gly Ala
1               5                   10                  15

Ser Val Lys Met Ser Cys Lys Ala Ser Gly Asp Ser Phe Thr Arg Tyr
            20                  25                  30

Trp Met His Trp Val Lys Gln Arg Pro Gly Gln Gly Leu Glu Trp Ile
        35                  40                  45

Gly Gly Ile Tyr Pro Gly Asn Ser Asp Thr Arg Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Gly Tyr Gly Pro Tyr Trp Gly Gln Gly Thr Thr Leu Thr
            100                 105                 110

Val Ser Ser
        115


<210> SEQ ID NO 146
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Leu Trp Ser Tyr Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 147
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Tyr Tyr Thr Tyr Glu Val Leu Asp Ile Trp Gly Gln Gly
            100                 105                 110

Thr Phe Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 148
<211> LENGTH: 451

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Met His Trp Val Arg Gln Ala Pro Gly Gln Gly Leu Glu Trp Met
        35                  40                  45

Gly Arg Ile Ser Pro Gly Gly Gly Gly Thr Ile Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gln Ser Glu Gly Leu Ser Tyr Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 149
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Met Ser Trp Val Arg Gln Ala Pro Gly Lys Gly Leu Glu Trp Val
35 40 45

Ser Arg Ile Ser Ser Ser Gly Ser Ser Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Trp Gly Ser Tyr Gly Tyr Gly Leu Val Tyr Tyr Phe Asp Val
100 105 110

Trp Gly Gln Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val

```
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 150
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Arg Ile Ser Gly Ser Gly Gly Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gln Val Tyr Trp Ala Leu Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 151
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Gly Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys His Gly Tyr Gly Gln Glu Tyr Tyr Tyr Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 152
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Arg Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Thr Tyr Thr Arg Gly Phe Ala Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 153
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Arg Lys His Leu Ser Trp Trp Trp Leu Ala Thr Val Cys Met Leu
1               5                   10                  15

Leu Phe Ser His Leu Ser Ala Val Gln Thr Arg Gly Ile Lys His Arg
            20                  25                  30

Ile Lys Trp Asn Arg Lys Ala Leu Pro Ser Thr Ala Gln Ile Thr Glu
        35                  40                  45

Ala Gln Val Ala Glu Asn Arg Pro Gly Ala Phe Ile Lys Gln Gly Arg
    50                  55                  60

Lys Leu Asp Ile Asp Phe Gly Ala Glu Gly Asn Arg Tyr Tyr Glu Ala
65                  70                  75                  80

Asn Tyr Trp Gln Glu Pro Asp Gly Ile His Tyr Asn Gly Cys Ser Glu
                85                  90                  95

Ala Asn Val Thr Lys Glu Ala Pro Val Thr Gly Cys Ile Asn Ala Thr
            100                 105                 110

Gln Ala Ala Asn Gln Glu Phe Gln Lys Pro Asp Lys Leu His Gln Gln
        115                 120                 125

Val Leu Trp Arg Leu Val Gln Glu Leu Cys Ser Leu Lys His Cys Glu
    130                 135                 140

Phe Trp Leu Glu Arg Gly His His His His His His
145                 150                 155


<210> SEQ ID NO 154
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Lys Asn Arg Leu Gly Thr Trp Trp Val Ala Ile Leu Cys Met Leu
1               5                   10                  15

Leu Ala Ser His Leu Ser Thr Val Lys Ala Arg Gly Ile Lys His Arg
            20                  25                  30

Phe Lys Trp Asn Arg Lys Val Leu Pro Ser Ser Gly Gly Gln Ile Thr
        35                  40                  45

Glu Ala Arg Val Ala Glu Asn Arg Pro Gly Ala Phe Ile Lys Gln Gly
    50                  55                  60

Arg Lys Leu Asp Ile Asp Phe Gly Ala Glu Gly Asn Arg Tyr Tyr Ala
65                  70                  75                  80

Ala Asn Tyr Trp Gln Phe Pro Asp Gly Ile Tyr Tyr Glu Gly Cys Ser
                85                  90                  95
```

```
Glu Ala Asn Val Thr Lys Glu Met Leu Val Thr Ser Cys Val Asn Ala
            100                 105                 110

Thr Gln Ala Ala Asn Gln Ala Glu Phe Ser Arg Glu Lys Gln Asp Ser
        115                 120                 125

Lys Leu His Gln Arg Val Leu Trp Arg Leu Ile Lys Glu Ile Cys Ser
    130                 135                 140

Ala Lys His Cys Asp Phe Trp Leu Glu Arg Gly His His His His His
145                 150                 155                 160

His


<210> SEQ ID NO 155
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Thr Ala Thr Tyr Tyr Cys His Gln Tyr His Arg Ser Pro
                85                  90                  95

Leu Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 156
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
```

```
caaattgttc tcacccagtc tccagcaatc atgtctgcat ctctagggga acgggtcacc     60

atgacctgca ctgccagctc aagtgtaagt tccagttact tgcactggta ccagcagaag    120

ccaggatcct cccccaaact ctggatttat agcacatcca acctggcttc tggagtccca    180

gctcgcttca gtggcagtgg gtctgggacc tcttactctc tcacaatcag cagcatggag    240

gctgaagata ctgccactta ttactgccac cagtatcatc gttccccact cacgttcggt    300

gctgggacca agctggagct gaaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttag                 648
```

```
<210> SEQ ID NO 157
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Leu Trp Val Lys Gln Ser His Gly Lys Ser Leu Glu Trp Ile
        35                  40                  45

Gly Asn Ile Asn Pro Tyr Tyr Gly Ser Thr Ser Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asn Tyr Tyr Gly Asn Tyr Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 158
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158

gagatccagc tgcagcagac tggacctgag ctggtgaagc ctggggcttc agtgaagata     60

tcctgcaagg cttctggtta ttcattcact gactacatca tgctctgggt gaagcagagc    120

catggaaaga gccttgagtg gattggaaat attaatcctt actatggtag tactagctac    180

aatctgaagt tcaagggcaa ggccacattg actgtagaca aatcttccag cacagcctac    240

atgcagctca acagtctgac atctgaggac tctgcagtct attactgtgc aagaaggaac    300

tactatggta actacgatgc tatggactac tggggtcaag gaacctcagt caccgtctcc    360

tcagctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagcct gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840
```

```
tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggac   1080

gagctgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaatga                             1356
```

```
<210> SEQ ID NO 159
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Ala Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Tyr Arg Phe Thr Gly
    50                  55                  60

Ser Gly Ser Gly Thr Asp Phe Thr Leu Thr Ile Ser Asn Val Gln Ser
65                  70                  75                  80

Ala Asp Leu Ala Glu Tyr Phe Cys Gln Gln Tyr Asn Ser Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 160
<211> LENGTH: 645
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 160

```
gacattgtga tgacccagtc tcaaaaattc atgtccacat cagtaggaga cagggtcagc     60

gtcacctgca aggccagtca gaatgtggat gctaatgtag cctggtatca acagaaacca    120

ggacaatctc ctaaagcact gatttactcg gcatcctacc ggtacagtgg agtcccttat    180

cgcttcacag gcagtggatc tgggacagat ttcactctca ccatcagcaa tgtgcagtct    240

gcagacttgg cagagtattt ctgtcagcaa tataacagct atccattcac gttcggctcg    300

gggacaaagt tggaaataaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 161
<211> LENGTH: 447
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 161

```
Gln Val Gln Leu Gln Gln Ser Gly Ala Glu Leu Val Arg Pro Gly Val
1               5                   10                  15

Ser Val Lys Leu Ser Cys Lys Phe Ser Gly Phe Thr Phe Thr Asp Tyr
            20                  25                  30

Ala Met His Trp Val Arg Gln Ser His Ala Lys Ser Leu Ala Trp Ile
        35                  40                  45

Gly Val Ile Ser Ser Tyr Tyr Gly Asp Ala Ser Tyr Asn Gln Lys Phe
    50                  55                  60

Thr Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Arg Leu Arg Gly Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 162
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162

```
caggtccagc tgcagcagtc tggggctgag ctggtgaggc ctggggtctc agtgaaactt     60

tcctgcaagt tttctggctt cacattcact gattatgcta tgcactgggt gaggcagagt    120

catgcaaaga gtctagcgtg gattggagtt attagttctt actatggtga tgctagctac    180

aaccagaagt tcacgggcaa ggccacaatg actgtagata aatcctccag cacagcctat    240

atggaacttg ccagactgac atctgaggat tctgccatct attactgtgc aagacgatta    300

cgaggggcta tggactactg gggtcaagga acctcagtca ccgtctcctc agctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcctgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780
```

```
tgcgtggtgg tggacgtgag ccacgaagac cctgaggtca agttcaactg gtacgtggac     840

ggcgtggagg tgcataatgc caagacaaag ccgcgggagg agcagtacaa cagcacgtac     900

cgtgtggtca gcgtcctcac cgtcctgcac caggactggc tgaatggcaa ggagtacaag     960

tgcaaggtct ccaacaaagc cctcccagcc cccatcgaga aaaccatctc caaagccaaa    1020

gggcagcccc gagaaccaca ggtgtacacc ctgcccccat cccgggacga gctgaccaag    1080

aaccaggtca gcctgacctg cctggtcaaa ggcttctatc ccagcgacat cgccgtggag    1140

tgggagagca atgggcagcc ggagaacaac tacaagacca cgcctcccgt gctggactcc    1200

gacggctcct tcttcctcta cagcaagctc accgtggaca agagcaggtg gcagcagggg    1260

aacgtcttct catgctccgt gatgcatgag gctctgcaca accactacac gcagaagagc    1320

ctctccctgt ctccgggtaa atga                                           1344


<210> SEQ ID NO 163
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Ile Val Met Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Gln Lys Pro Gly Gln Ala Pro Arg Leu Trp
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 164
<211> LENGTH: 648
<212> TYPE: DNA
<213> ORGANISM: Artificial Sequence
<220> FEATURE:
```

<223> OTHER INFORMATION: Description of Artificial Sequence: Synthetic polynucleotide

<400> SEQUENCE: 164

```
gagatcgtga tgacccagtc cccagccaca ctgtctctgt ccccaggaga gagagccacc     60

ctgagctgca cagcctcctc ctccgtgtcc tcctcctacc tgcactggta tcagcagaag    120

cccggccagg ctcctaggct gtggatctac agcacctcta acctggcctc tggcatcccc    180

gctcggttct ccggcagcgg ctctggcaca gactttaccc tgacaatctc cagcctgcag    240

cctgaggatt tcgccgtgta ctattgtcac cagtatcatc gctccccact gacctttggc    300

cagggcacaa aggtggagat caagcgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttag                 648
```

<210> SEQ ID NO 165
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Met Leu Trp Val Arg Gln Ala Pro Gly Gln Gly Leu Glu Trp Met
        35                  40                  45

Gly Asn Ile Asn Pro Tyr Tyr Gly Ser Thr Ser Tyr Asn Leu Lys Phe
    50                  55                  60

Lys Gly Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asn Tyr Tyr Gly Asn Tyr Asp Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 166
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
caggtgcagc tggtgcagtc cggagctgag gtgaagaagc caggagcctc cgtgaaggtg     60

tcttgcaagg cctctggcta ctccttcacc gactatatca tgctgtgggt gaggcaggct    120

ccaggacagg gactggagtg gatgggaaac atcaatcctt actatggcag cacatcttac    180

aacctgaagt ttaagggcag agtgaccatg acagtggaca agtccaccag cacagcctat    240

atggagctgt ccagcctgcg cagcgaggat accgccgtgt actattgtgc taggcggaac    300

tactatggca attacgacgc tatggattat tggggccagg gcaccctggt gacagtgtct    360

tccgctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagcct gggcacccag    600

acctacatct gcaacgtgaa tcacaagccc agcaacacca aggtggacaa gaaagttgag    660
```

```
cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggac   1080

gagctgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaatga                             1356
```

<210> SEQ ID NO 167
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ala Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 168

<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168

```
gacatccaga tgacccagag cccttccagc ctgagcgcct ctgtgggcga cagggtgacc     60

atcacatgca aggcttctca gaacgtggat gccaatgtgg cttggtacca gcagaagccc    120

ggcaaggccc ctaaggcgct gatctattcc gcctcctaca ggtattctgg agtgccatac    180

cggttctctg gctccggcag cggaaccgac tttaccctga caatctcttc cctgcagcca    240

gaggatttcg ccacatacta ttgtcagcag tacaactcct atcccttcac ctttggccag    300

ggcacaaagg tggagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 169
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Ala Met His Trp Val Arg Gln Ala Pro Gly Lys Gly Leu Ala Trp Val
        35                  40                  45

Ala Val Ile Ser Ser Tyr Tyr Gly Asp Ala Ser Tyr Asn Gln Lys Phe
    50                  55                  60

Thr Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Arg Gly Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 170
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

gaggtgcagc tggtggagtc tggaggagga ctggtgcagc caggaggcag cctgaggctg     60

tcttgcgccg cttccggctt cacctttaca gactacgcca tgcactgggt gagacaggct    120

cctggcaagg gactggcgtg ggtggccgtg atctccagct actatggcga cgcttcctac    180

aaccagaagt tcaccggcag gtttacaatc agcgtggata agtctaagaa caccctgtat    240

ctgcagatga atagcctgag agccgaggac acagccgtgt actattgtgc caggcggctg    300

cgcggcgcta tggattattg gggccagggc accctggtga cagtgtcttc cgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcctgg gcacccagac ctacatctgc    600

aacgtgaatc acaagcccag caacaccaag gtggacaaga aagttgagcc caaatcttgt    660
```

-continued

```
gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggacga gctgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atga                                          1344
```